US009234218B2

(12) United States Patent
Marx et al.

(10) Patent No.: US 9,234,218 B2
(45) Date of Patent: Jan. 12, 2016

(54) PROCESS FOR PREPARING METHACRYLIC ACID OR METHACRYLIC ESTERS

(75) Inventors: Achim Marx, Gelnhausen (DE); Markus Poetter, Muenster (DE); Stefan Buchholz, Hanau (DE); Alexander May, Seeheim (DE); Hermann Siegert, Seeheim-Jugenheim (DE); Birgit Alber, Stuttgart (DE); Georg Fuchs, Heitersheim (DE); Lothar Eggeling, Juelich (DE)

(73) Assignee: EVONIK ROEHM GmbH, Darmstadt (DE)

( * ) Notice: Subject to any disclaimer, the term of this patent is extended or adjusted under 35 U.S.C. 154(b) by 819 days.

(21) Appl. No.: 12/602,593

(22) PCT Filed: May 30, 2008

(86) PCT No.: PCT/EP2008/056707

§ 371 (c)(1), (2), (4) Date: Mar. 19, 2010

(87) PCT Pub. No.: WO2008/145737

PCT Pub. Date: Dec. 4, 2008

(65) Prior Publication Data

US 2010/0291644 A1 Nov. 18, 2010

(30) Foreign Application Priority Data

Jun. 1, 2007 (EP) .................. PCT/EP2007/055394

(51) Int. Cl.

| | |
|---|---|
| ***C12P 7/42*** | (2006.01) |
| ***C12P 7/52*** | (2006.01) |
| ***C12N 9/02*** | (2006.01) |
| ***C12P 7/40*** | (2006.01) |
| ***C12P 7/62*** | (2006.01) |
| ***C08F 120/06*** | (2006.01) |
| ***C08F 120/10*** | (2006.01) |
| ***C12N 9/10*** | (2006.01) |
| ***C12N 9/16*** | (2006.01) |
| ***C12N 9/88*** | (2006.01) |

(52) U.S. Cl.

CPC ................ *C12P 7/42* (2013.01); *C08F 120/06* (2013.01); *C08F 120/10* (2013.01); *C12N 9/001* (2013.01); *C12N 9/0008* (2013.01); *C12N 9/1096* (2013.01); *C12N 9/16* (2013.01); *C12N 9/88* (2013.01); *C12P 7/40* (2013.01); *C12P 7/52* (2013.01); *C12P 7/625* (2013.01); *C12Y 102/04004* (2013.01); *C12Y 103/99012* (2013.01); *C12Y 206/01042* (2013.01); *C12Y 301/02004* (2013.01); *C12Y 402/01017* (2013.01)

(58) Field of Classification Search

CPC .................................... C12P 7/42; C12P 7/52

IPC ................................................ C12P 7/42, 7/52

See application file for complete search history.

(56) References Cited

U.S. PATENT DOCUMENTS

| | | | |
|---|---|---|---|
| 3,562,320 | A | 2/1971 | Woodward et al. |
| 6,348,339 | B1 | 2/2002 | Cahoon et al. |
| 6,620,970 | B2 | 9/2003 | Schiffer et al. |
| 6,639,108 | B2 | 10/2003 | Schiffer et al. |
| 6,861,540 | B2 | 3/2005 | Herwig et al. |
| 6,878,836 | B2 | 4/2005 | Haas et al. |
| 7,030,052 | B2 | 4/2006 | Stochniol et al. |
| 7,049,450 | B2 | 5/2006 | Hofen et al. |
| 7,091,384 | B2 | 8/2006 | Jaeger et al. |
| 7,507,862 | B2 | 3/2009 | Stochniol et al. |
| 7,879,938 | B2 | 2/2011 | Haeger et al. |

(Continued)

FOREIGN PATENT DOCUMENTS

| | | |
|---|---|---|
| EP | 0 722 929 A1 | 7/1996 |
| EP | 1 186 592 | 3/2002 |

(Continued)

OTHER PUBLICATIONS

E.K. Chowdhury et al. "Cloning and Overexpression of the 3-Hydroxyisobutyrate Dehydrogenase Gene from Pseudomonas putida E23", Biosci. Biotechnol. Biochem. 67(2):438-441. (2003).*

Russian Office Action Issued Apr. 17, 2012 in Patent Application No. 2009148592/10(071762) (with English translation).

I.L. Knunyants et al., "Soviet Encyclopaedia", Chemical Encyclopaedic Dictionary, 1983, p. 325 and cover pages.

Korotkova, Natalia et al., "Glyoxylate Regeneration Pathway in the Methylotroph Methylobacterium extorquens AM1", Journal of Bacteriology, vol. 184, No. 6, pp. 1750-1758, (Mar. 2002).

Lee, I.Y. et al., "High production of D-Beta-hydroxyisobutyric acid from methacrylic acid by Candida rugosa and its mutant", Bioprocess Engineering, vol. 16, No. 5, pp. 247-252, (1997).

(Continued)

*Primary Examiner* — Rebecca Prouty

(74) *Attorney, Agent, or Firm* — Oblon, McClelland, Maier & Neustadt, L.L.P.

(57) ABSTRACT

The present invention relates to a process for the preparation of methacrylic acid or methacrylic esters, comprising the process steps of IA) preparation of 3-hydroxyisobutyric acid by a process comprising the process step of bringing a cell which has been genetically modified in comparison with its wild type in such a way that it is capable of forming more 3-hydroxyisobutyric acid, or polyhydroxyalkanoates based on 3-hydroxyisobutyric acid in comparison with its wild type, into contact with a nutrient medium comprising, as carbon source, carbohydrates, glycerol, carbon dioxide, methanol, L-valine or L-glutamate under conditions under which 3-hydroxyisobutyric acid or polyhydroxyalkanoates based on 3-hydroxyisobutyric acid are formed from the carbon source, if appropriate, isolation of the 3-hydroxyisobutyric acid from the nutrient medium and also, if appropriate, neutralization of the 3-hydroxyisobutyric acid, IB) dehydration of the 3-hydroxyisobutyric acid with formation of methacrylic acid and also, where appropriate, esterification methacrylic acid.

The invention also relates to a process for the preparation of polymethacrylic acid or polymethacrylic esters.

6 Claims, 27 Drawing Sheets

(56) References Cited

U.S. PATENT DOCUMENTS

| | | | | |
|---|---|---|---|---|
| 8,216,813 | B2 | 7/2012 | Thum et al. | |
| 8,241,877 | B2 * | 8/2012 | Burgard et al. | 435/136 |
| 8,372,595 | B2 | 2/2013 | Schaffer et al. | |
| 8,399,658 | B2 | 3/2013 | Hengstermann et al. | |
| 8,445,720 | B2 | 5/2013 | Hannen et al. | |
| 8,604,227 | B2 | 12/2013 | Petrat et al. | |
| 9,000,223 | B2 | 4/2015 | Micoine et al. | |
| 2002/0055650 | A1 | 5/2002 | Hidaka et al. | |
| 2002/0087036 | A1 | 7/2002 | Haas et al. | |
| 2004/0076982 | A1 | 4/2004 | Gokarn et al. | |
| 2005/0222458 | A1 * | 10/2005 | Craciun et al. | 562/599 |
| 2008/0194875 | A1 | 8/2008 | Ackermann et al. | |
| 2009/0182167 | A1 | 7/2009 | May et al. | |
| 2009/0209781 | A1 | 8/2009 | Ackermann et al. | |
| 2010/0035314 | A1 | 2/2010 | Mueller et al. | |
| 2010/0167360 | A1 | 7/2010 | Thum et al. | |
| 2010/0261237 | A1 | 10/2010 | Verseck et al. | |
| 2010/0266518 | A1 | 10/2010 | Springer et al. | |
| 2010/0324257 | A1 | 12/2010 | Karau et al. | |
| 2011/0039313 | A1 | 2/2011 | Verseck et al. | |
| 2011/0118433 | A1 | 5/2011 | Poetter et al. | |
| 2011/0251399 | A1 | 10/2011 | Dingerdissen et al. | |
| 2011/0257429 | A1 | 10/2011 | Schraven et al. | |
| 2012/0034665 | A1 | 2/2012 | Haas et al. | |
| 2012/0041216 | A1 | 2/2012 | Sieber et al. | |
| 2012/0245375 | A1 | 9/2012 | Hannen et al. | |
| 2012/0315366 | A1 | 12/2012 | Zehnacker et al. | |
| 2013/0035403 | A1 | 2/2013 | Schaffer et al. | |
| 2013/0052700 | A1 | 2/2013 | Poetter et al. | |
| 2013/0092233 | A1 | 4/2013 | Pawlik et al. | |
| 2013/0130319 | A1 | 5/2013 | Schaffer et al. | |
| 2013/0164797 | A1 | 6/2013 | Gielen et al. | |
| 2013/0165672 | A1 | 6/2013 | Klasovsky et al. | |
| 2013/0165685 | A1 | 6/2013 | Hannen et al. | |
| 2013/0183725 | A1 | 7/2013 | Poetter et al. | |
| 2013/0245276 | A1 | 9/2013 | Klasovsky et al. | |
| 2013/0331580 | A1 | 12/2013 | Klasovsky et al. | |
| 2014/0141478 | A1 | 5/2014 | Schaffer et al. | |
| 2014/0178948 | A1 | 6/2014 | Schaffer et al. | |
| 2014/0199736 | A1 | 7/2014 | Köhler et al. | |

FOREIGN PATENT DOCUMENTS

| | | | |
|---|---|---|---|
| JP | 2002/155025 | | 5/2002 |
| WO | WO 2005/095320 | A1 | 10/2005 |
| WO | WO 2009/135074 | A2 | 11/2009 |

OTHER PUBLICATIONS

U.S. Appl. No. 12/441,145, filed Mar. 13, 2009, May, et al.
U.S. Appl. No. 12/442,145, filed Mar. 23, 2009, Vogel, et al.
U.S. Appl. No. 12/593,090, filed Sep. 25, 2009, Marx, et al.
U.S. Appl. No. 12/303,161, filed Dec. 2, 2008, Marx, et al.
Chinese Office Action issued Aug. 29, 2011, in Patent Application No. 200880010552.3 (with English-language translation).
Copeland, A., et al., Genbank database, CP000577, XP002487016, Feb. 23, 2007.
Copeland, A., et al., Genbank database, ABN77722, Feb. 23, 2007.
U.S. Appl. No. 13/001,204, filed Dec. 23, 2010, Reinecke, et al.
U.S. Appl. No. 13/002,519, filed Jan. 4, 2011, Haas, et al.
U.S. Appl. No. 12/950,752, filed Nov. 19, 2010, Mueller, et al.
U.S. Appl. No. 13/500,041, filed Apr. 3, 2012, Reinecke, et al.
Andreas Abend, et al., "Further Insights into the Mechanism of Action of Methylmalonyl-CoA Mutase by Electron Paramagnetic Resonance Studies" Eur. J. Biochem, 249, (pp. 180-186), 1997.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/000,067, filed Aug. 16, 2013, Erhardt, et al.
U.S. Appl. No. 14/000,028, filed Aug. 16, 2013, Erhardt, et al.
U.S. Appl. No. 14/126,607, filed Dec. 16, 2013, Haas, et al.
U.S. Appl. No. 14/363,178, filed Jun. 5, 2014, Haas, et al.
U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.
U.S. Appl. No. 14/384,301, filed Sep. 10, 2014, Schaffer, et al.
U.S. Appl. No. 14/390,133, filed Oct. 2, 2014, Hennemann, et al.
U.S. Appl. No. 14/395,666, filed Oct. 20, 2014, Haas, et al.
U.S. Appl. No. 14/435,339, filed Apr. 13, 2015, Engel, et al.
U.S. Appl. No. 14/419,580, filed Feb. 4, 2015, Erhardt, et al.
Notice of opposition to a European patent issued Jan. 24, 2014 in Patent Application No. EP08760294.2.
Birgit Alber, et al., "Malonyl-Coenzyme A Reductase in the Modified 3-Hydroxypropionate Cycle for Autotrophic Carbon Fixation in Archaeal Metallosphaera and Sulfolobus spp.", Journal of Bacteriology, vol. 188, No. 24, Dec. 2006, pp. 8551-8559.
Fang-Jong Ko, et al., "3-Hydroxyisobutyric Aciduria: An Inborn Error of Valine Metabolism", Pediatric Research, vol. 30, No. 4, (1991), pp. 322-326.
Notice of Opposition dated Sep. 23, 2015, in European patent application No. 08760294.2.
Notice of Opposition dated Oct. 8, 2015, in European patent application No. 08760294.2.
Declaration of Archer (Sep. 16, 2015), submitted in opposition proceesings filed in European patent application No. 08760294.2.
Declaration of Baxter (Sep. 15, 2015), submitted in opposition proceedsings filed in European patent application No. 08760294.2.
Demmer et al, "Structural Basis for a Bispecific $NADP^+$ and CoA Binding Site in an Archaeal Malonyl-Coenzyme A Reductase", Journal of Biological Chemistry, 2013, vol. 288, No. 9, pp. 6363-6370.
Gande et al, "The Two Carboxylases of *Corynebacterium glutamicum* Essential for Fatty Acid and Mycolic Acid Synthesis", Journal of Bacteriology, 2007, vol. 189, No. 14, pp. 5257-5264.
Reinscheid et al, "Cloning, sequence analysis, expression and inactivation of the *Corynebacterium glutamicum pta-ack* operon encoding phosphotransacetylase and acetate kinase", 1999, Microbiology, vol. 145, pp. 503-513.
Sprecher et al, "The Absolute Configuration of Methylmalonyl Coenzyme A and Stereochemistry of the Methylmalonyl. Coenzyme A Mutase Reaction", 1966, The Journal of Biological Chemistry, vol. 241, No. 4, pp. 872-877.

* cited by examiner

Succinyl-coenzyme A $E_1$

Methylmalonyl-coenzyme A

Methylmalonyl-coenzyme A $E_2$

Methyl malonate $E_3$

Methylmalonate semialdehyde $E_4$

3-Hydroxyisobutyric acid (R)-Methylmalonyl-coenzyme A (S)-Methymalonyl-coenzyme A 3-Hydroxyisobutyric acid Propionyl-coenzyme A Methylmalonate semialdehyde Methylmalonyl-coenzyme A Propionyl-coenzyme A Methylmalonate semialdehyde 3-Hydroxyisobutyric acid 3-Hydroxyisobutyric acid 3-Hydroxyisobutyryl-coenzyme A Polyhydroxyalkanoate Phosphoenolpyruvate Pyruvate Oxaloacetate Oxaloacetate Malate Fumarate Succinate Succinyl-coenzyme A Oxaloacetate Citrate Isocitrate Glyoxylate Malate Fumarate Succinate Succinyl-coenzyme A Oxaloacetate Citrate Isocitrate 2-Oxoglutarate Succinyl-coenzyme A L-Glutamate 2-Oxoglutarate Succinyl-coenzyme A Acetyl-coenzyme A Malonyl-coenzyme A Acryloyl-coenzyme A Malonate semialdehyde 3-Hydroxypropionate 3-Hydroxypropionyl-coenzyme A Propionyl-coenzyme A (S)-Methymalonyl-coenzyme A (R)-Methylmalonyl-coenzyme A 3-
3-Hydroxyisobutyric acid Methylmalonate semialdehyde Methyl malonate Acetyl-coenzyme A Malonyl-coenzyme A Malonate semialdehyde 3-Hydroxypropionate 3-Hydroxypropionyl-coenzyme A Acryloyl-coenzyme A Propionyl-coenzyme A 3-Hydroxyisobutyric acid Methylmalonate semialdehyde Methyl malonate Methylmalonyl-coenzyme A Acetyl-CoA + Acetyl-CoA Acetoacetyl-CoA (R)-3-Hydroxybutyrate Crotonyl-CoA Ethylmalonyl-CoA Methylsuccinyl-CoA Mesaconyl-CoA β-Methylmalyl-CoA Glyoxylate Propionyl-CoA beta-Alanine beta-Alanyl-CoA Acryloyl-CoA Methylmalonyl-CoA Methyl malonate Methylmalonate semialdehyde 3-Hydroxyisobutyric acid (S)-2-Acetolactate Pyruvate 2,3-Dihydroxyisovalerate 2-Oxoisovalerate Isobutyryl-coenzyme A 3-Hydroxyisobutyric acid 3-Hydroxyisobutyryl-coenzyme A Methacrylyl-coenzyme A 3-Hydroxyisobutyric acid 3-Hydroxyisobutyryl-coenzyme A L-Valine 2-Oxoisovalerate Methacrylyl-coenzyme A Isobutyryl-coenzyme A

PROCESS FOR PREPARING METHACRYLIC ACID OR METHACRYLIC ESTERS

CROSS-REFERENCE TO RELATED APPLICATIONS

The present application is a 35 U.S.C. §371 National Stage patent application of International patent application PCT/EP2008/056707, filed on May 30, 2008, which claims priority to International patent application PCT/EP2007/055394, filed on Jun. 1, 2007.

The present invention relates to a process for the preparation of methacrylic acid or methacrylic esters, and to a process for the preparation of polymethacrylic acid or polymethacrylic esters.

Methacrylic acid is an important intermediate which is employed for the preparation of polymers, in particular in the form of its alkyl esters. An example of a well-known methacrylic acid derivative is the methyl ester of methacrylic acid. The current global annual production of methyl methacrylate amounts to approximately 1.5 million tonnes. The polymethacrylic esters are raw materials in the plastics sector with a multiplicity of uses.

Methacrylic acid is usually produced commercially by means of the heterogeneous gas-phase oxidation of $C_4$-carbon compounds such as butylene, isobutylene, butane, isobutane, t-butyl alcohol or methacrolein by two-step catalysis on solid multi-metal oxide compositions as the catalyst. The resulting product gas mixture, which, besides methacrylic acid, also comprises a large number of secondary products, is subsequently either subjected to a total condensation reaction, generating aqueous methacrylic acid solution, or absorbed in a suitable solvent mixture. This is usually followed by further purification of the resulting liquid phases by means of distillation, crystallization, extraction, or a combination of these measures. Besides the catalytic gas-phase oxidation of $C_4$-carbon compounds, methacrylic acid can also be formed from isobutyric acid by catalytic oxidative dehydrogenation, as is described for example in EP-A-0 356 315. A further possibility for preparing methacrylic acid is what is known as the "ACH process", in which acetone cyanohydrin and sulfuric acid are reacted with the formation of methacrylamide as intermediate, which then reacts further with water to give methacrylic acid. The resulting methacrylic acid is subsequently purified by distillation. This process is described for example in EP-A-1 359 137.

The disadvantage of these conventional processes for the preparation of methacrylic acid is, inter alia, that during both the preparation of the methacrylic acid itself and during the subsequent steps, which involve purification by distillation, the process steps, which cause thermal stress, result, owing to the pronounced susceptibility of methacrylic acid to polymerization, in the formation of dimers or oligomers; this not only entails additional purification efforts, but also yield losses.

It was an object of the present invention to overcome the disadvantages of the prior art.

In particular, it was an object of the present invention to provide a process for the preparation of methacrylic acid which generates methacrylic acid with a minimum of steps which involve thermal stress.

Furthermore, it is intended that this process makes possible the preparation of methacrylic acid from renewable resources, in particular from carbohydrates and/or glycerol.

A contribution to achieving the abovementioned aims is provided by a process for the preparation of methacrylic acid or methacrylic esters, comprising the process steps of IA) preparation of 3-hydroxyisobutyric acid by a process comprising the process step of bringing a cell which has been genetically modified in comparison with its wild type in such a way that it is capable of forming more 3-hydroxyisobutyric acid, or polyhydroxyalkanoates based on 3-hydroxyisobutyric acid in comparison with its wild type, into contact with a nutrient medium comprising, as carbon source, carbohydrates, glycerol, carbon dioxide, methane, methanol, L-valine or L-glutamate under conditions under which 3-hydroxyisobutyric acid or polyhydroxy-alkanoates based on 3-hydroxyisobutyric acid are formed from the carbon source, if appropriate, isolation of the 3-hydroxyisobutyric acid from the nutrient medium and also, if appropriate, neutralization of the 3-hydroxyisobutyric acid. The formation of the 3-hydroxyisobutyric acid or of the polyhydroxyalkanoates based on 3-hydroxyisobutyric acid preferably taking place via methylmalonate semialdehyde or via 3-hydroxyisobutyryl-coenzyme A as precursor;

IB) dehydration of the 3-hydroxyisobutyric acid with formation of methacrylic acid and also, where appropriate, esterification methacrylic acid.

In the event that the formation of 3-hydroxyisobutyric acid or of polyhydroxyalkanoates based on 3-hydroxy-isobutyric acid takes place via methylmalonate semialdehyde as precursor, it is furthermore preferred that the formation takes place via succinyl-coenzyme A, propionyl-coenzyme A or acryloyl-coenzyme A, especially preferably via succinyl-coenzyme A, as further intermediate. In the event that the formation of 3-hydroxyisobutyric acid or of polyhydroxyalkanoates based on 3-hydroxyisobutyric acid takes place via 3-hydroxyisobutyryl-coenzyme A as precursor, it is furthermore preferred that the formation takes place via isobutyryl-coenzyme A or via 3-hydroxybutyryl-coenzyme A, preferably via 3-hydroxybutyryl-coenzyme A, as further intermediate.

The term "precursor" as used in the present context defines a chemical compound which can be converted enzymatically into 3-hydroxyisobutyric acid in just one reaction step, while the term "intermediate" defines a chemical compound which cannot be converted enzymatically into 3-hydroxyisobutyric acid in just one reaction step.

The term "3-hydroxyisobutyric acid" as used in the present context always describes the corresponding $C_4$-carboxylic acid in the form in which it is present as a function of the pH, after having been formed by the microorganisms in question. As a consequence, the term always comprises the pure acid form (3-hydroxyisobutyric acid), the pure base form (3-hydroxyisobutyrate) and mixtures of protonated and deprotonated forms of the acid. Furthermore, the term "3-hydroxyisobutyric acid" comprises, in principle, both the (R) and the (S) stereoisomer, the (S) stereoisomer being especially preferred.

The wording "that it is capable of forming more 3-hydroxyisobutyric acid or polyhydroxyalkanoates based on 3-hydroxyisobutyric acid in comparison with its wild type" also applies in the event that the wild type of the genetically modified cell is not capable of forming any 3-hydroxyisobutyric acid or polyhydroxyalkanoates based on 3-hydroxyisobutyric acid, but at least no detectable amounts of these compounds, and that detectable amounts of these components are only capable of being formed after the genetic modification.

A "wild type" of a cell preferably refers to a cell whose genome is present in a state as generated naturally as the result of evolution. The term is used both for the entire cell and for individual genes. As a consequence, the term "wild type"

does not cover in particular those cells, or those genes, whose gene sequences have at least in part been modified by man by means of recombinant methods.

The 3-hydroxyisobutyric acid subsequently gives rise to methacrylic acid by subjecting it to a dehydration reaction under mild conditions. In the case of polyhydroxyalkanoates based on 3-hydroxyisobutyric acid, the vesicles present in the cells, which are filled with these polyhydroxyalkanoates, can be isolated and the polymers can subsequently be cleaved to give 3-hydroxyisobutyric acid, which can then be dehydrated to give methacrylic acid.

In this context, it is preferred according to the invention that the genetically modified cell used in the process according to the invention has been genetically modified in such a way that it forms at least twice, especially preferably at least 10 times, more preferably at least 100 times, even more preferably at least 1000 times and most preferably at least 10 000 times more 3-hydroxyisobutyric acid or polyhydroxyalkanoates based on 3-hydroxyisobutyric acid than the wild type of the cell within a defined time interval, preferably within 2 hours, even more preferably within 8 hours and most preferably within 24 hours. The increase in the formation of product can be determined in this context for example by growing the cell used in the process according to the invention and the wild-type cell in each case separately, but under identical conditions (identical cell density, identical nutrient medium, identical culture conditions) for a particular time interval in a suitable nutrient medium and subsequently determining the amount of target product (3-hydroxyisobutyric acid or polyhydroxy-alkanoates based on 3-hydroxyisobutyric acid) in the nutrient medium.

The cells used in the process according to the invention may be prokaryotic or eukaryotic cells. They may take the form of mammalian cells (such as, for example, human cells), of plant cells or of microorganisms such as yeasts, fungi or bacteria, with microorganisms being especially preferred and bacteria and yeasts being most preferred.

Suitable bacteria, yeasts or fungi are in particular those bacteria, yeasts or fungi which have been deposited at the Deutsche Sammlung von Mikroorganismen and Zellkulturen GmbH (DSMZ), Brunswick, Germany, as bacterial, yeast or fungal strains.

Bacteria which are suitable according to the invention belong to the genera detailed under http://www.dsmz.de/species/bacteria.htm, yeasts which are suitable according to the invention belong to those genera which are detailed under http://www.dsmz.de/species/yeasts.htm, and fungi which are suitable according to the invention are those which are detailed under http://www.dsmz.de/species/fungi.htm.

Cells which are especially preferably used according to the invention are those of the genera *Corynebacterium, Brevibacterium, Bacillus, Acinetobacter, Lactobacillus, Lactococcus, Candida, Pichia, Kluveromyces, Saccharomyces, Escherichia, Zymomonas, Yarrowia, Methylobacterium, Ralstonia, Pseudomonas, Burkholderia* and *Clostridium*, with *Brevibacterium flavum, Brevibacterium lactofermentum, Escherichia coli, Saccharomyces cerevisiae, Kluveromyces lactis, Candida blankii, Candida rugosa, Corynebacterium glutamicum, Corynebacterium efficiens, Zymonomas mobilis, Yarrowia lipolytica, Methylobacterium extroquens, Ralstonia eutropha*, especially *Ralstonia eutropha* H16, *Rhodospirillum rubrum, Rhodobacter sphaeroides, Paracoccus versutus, Pseudomonas aeroginosa, Acinetobacter calcoaceticus* and *Pichia pastoris* being especially preferred.

In accordance with a first variant of the process according to the invention, a cell is used, in which the formation of 3-hydroxyisobutyric acid or of polyhydroxyalkanoates based on 3-hydroxyisobutyric acid takes place via methylmalonate semialdehyde as precursor.

In accordance with a first special embodiment of this first variant of the process according to the invention, it is preferred that the formation of 3-hydroxyisobutyric acid or of the polyhydroxyalkanoate based on 3-hydroxyisobutyric acid preferentially takes place via succinyl-coenzyme A as intermediate, where the genetically modified cell used in this embodiment of the process according to the invention preferentially is capable of utilizing carbohydrates, glycerol or glutamate as the carbon source.

Here, it may be advantageous in the context of the first special embodiment of the first variant of the process according to the invention that the genetically modified cell used in this embodiment of the process according to the invention features an increased activity of an enzyme $E_1$, which catalyzes the conversion of succinyl-coenzyme A into methylmalonyl-coenzyme A, in comparison with its wild type (see FIG. 1).

The term "increased activity of an enzyme" as used above in connection with the enzyme $E_1$ and in what follows in the context of the enzymes $E_2$ etc. is preferably to be understood as increased intracellular activity.

What now follows on increasing the enzymatic activity in cells applies both to increasing the activity of the enzyme $E_1$ and to all enzymes mentioned thereafter, whose activity can, if appropriate, be increased.

In principle, an increase in the enzymatic activity can be achieved by increasing the copy number of the gene sequence(s) which code for the enzyme, by using a strong promoter or by using a gene or allele which codes for a corresponding enzyme with an increased activity, and, if appropriate, combining these measures. Cells which have been genetically modified in accordance with the invention are generated for example by transformation, transduction, conjugation or a combination of these methods with a vector which comprises the desired gene, an allele of this gene or parts thereof, and a vector which makes possible the expression of the gene. The heterologous expression is achieved in particular by integration of the gene, or of the alleles, into the chromosome of the cell or into an extrachromosomally replicating vector.

An overview over the possibilities for increasing the enzymatic activity in cells with pyruvate carboxylase by way of example is found in DE-A-100 31 999, which is hereby incorporated by reference and whose disclosure content regarding the possibilities for increasing the enzymatic activity in cells forms part of the disclosure of the present invention.

The expression of the enzymes or genes mentioned hereinabove and in each case hereinbelow can be detected in the gel with the aid of 1- and 2-dimensional protein gel separation and subsequent visual identification of the protein concentration using suitable evaluation software. When the increase in an enzymatic activity is based exclusively on an increase in the expression of the gene in question, the quantification of the increase in the enzymatic activity can be determined in a simple manner by comparing the 1- or 2-dimensional protein separations between the wild type and the genetically modified cell. A conventional method of preparing the protein gels in coryneform bacteria, and of identifying the proteins, is the procedure described by Hermann et al. (*Electrophoresis,* 22: 1712.23 (2001)). The protein concentration can also be analyzed by Western blot hybridization using an antibody which is specific for the protein to be detected (Sambrook et al., *Molecular Cloning: a laboratory manual,* $2^{nd}$ Ed. Cold Spring Harbor Laboratory Press, Cold Spring Harbor, N.Y. USA, 1989) followed by visual evaluation with suitable software for determining the concentration (Lohaus and Meyer (1989) *Biospektrum,* 5: 32-39; Lottspeich (1999), *Angewandte Chemie* 111: 2630-2647). The activity of DNA-binding proteins can be measured by means of DNA band shift assays (also referred to as gel retardation) (Wilson et al. (2001) *Journal of Bacteriology,* 183: 2151-2155). The effect of DNA-binding proteins on the expression of other genes can be detected by various, extensively described methods of the reporter gene assay (Sambrook et al., *Molecular Cloning: a laboratory manual,* $2^{nd}$ Ed. Cold Spring Harbor Laboratory Press, Cold Spring Harbor, N.Y. USA, 1989). The intracellular enzymatic activities can be detected by various methods which have been described (Donahue et al. (2000) *Journal of Bacteriology* 182 (19): 5624-5627; Ray et al. (2000) *Journal of Bacteriology* 182 (8): 2277-2284; Freedberg et al. (1973) *Journal of Bacteriology* 115 (3): 816-823). In the event that no specific methods for determining the activity of a particular enzyme are detailed in what follows, the determination of the increase in the enzymatic activity, and also the determination of the reduction in an enzymatic activity, is preferably carried out by means of the methods described in Hermann et al., Electrophoresis, 22: 1712-23 (2001), Lohaus et al., Biospektrum 5 32-39 (1998), Lottspeich, *Angewandte Chemie* 111: 2630-2647 (1999) and Wilson et al. *Journal of Bacteriology,* 183: 2151-2155 (2001).

If increasing the enzymatic activity is brought about by mutating the endogenous gene, such mutations can be generated either undirected, using traditional methods such as for example by UV irradiation or by mutagenic chemicals, or directed by means of recombinant methods such as deletion(s), insertion(s) and/or nucleotide substitution(s). These mutations give rise to genetically modified cells. Especially preferred mutants of enzymes are in particular also those enzymes which are no longer capable of being feedback-inhibited, or which are at least less capable of being feedback-inhibited, in comparison with the wild-type enzyme.

If increasing the enzymatic activity is brought about by increasing the expression of an enzyme, then, for example, the copy number of the respective genes are increased, or the promoter and regulatory regions or the ribosomal binding site, which is located upstream of the structural gene, are mutated. Expression cassettes which are incorporated upstream of the structural gene act in the same manner. By means of inducible promoters it is additionally possible to increase the expression at any desired point in time. Furthermore, the enzyme gene may also have assigned to it what are known as enhancer sequences as regulatory sequences; these also bring about an increased gene expression via an improved interaction between RNA polymerase and DNA. Measures for extending the life of the mRNA also improves expression. Furthermore, preventing the degradation of the enzyme protein also enhances the enzymatic activity. Here, the genes or gene constructs are either present in plasmids in different copy numbers, or else they are integrated and amplified in the chromosome. As an alternative, overexpression of the genes in question may also be achieved by modifying the media composition and the control of the culture.

Instructions for doing so can be found by the skilled worker in Martin et al. (*Bio/Technology* 5, 137-146 (1987)) in Guerrero et al. (*Gene* 138, 35-41 (1994)), Tsuchiya and Morinaga (*Bio/Technology* 6, 428-430 (1988)), in Eikmanns et al. (*Gene* 102, 93-98 (1991)), in EP-A-0 472 869, in U.S. Pat. No. 4,601,893, in Schwarzer and Pühler ((*Bio/Technology* 9, 84-87 (1991), in Reinscheid et al. (*Applied and Environmental Microbiology* 60, 126-132 (1994)), in LaBarre et al. (Journal of Bacteriology 175, 1001-1007 (1993)), in WO-A-96/15246, in Malumbres et al. (Gene 134, 15-24 (1993), in JP-A-10-229891, in Jensen and Hammer (*Biotechnology and Bioengineering* 58, 191-195 (1998)), inter alia, and in known textbooks of genetics and molecular biology. The above-described measures give rise to genetically modified cells, as do the mutations.

Plasmids, for example episomal plasmids, are employed for increasing the expression of the genes in question. Suitable plasmids are in particular those which are replicated in coryneform bacteria. A large number of known plasmid vectors such as, for example, pZ1 (Menkel et al., *Applied and Environmental Microbiology* 64: 549-554 (1989)), pEKEx1 (Eikmanns et al., *Gene* 107: 69-74 (1991)) or pHS2-1 (Sonnen et al., *Gene* 107: 69-74 (1991)) are based on the cryptic plasmids pHM1519, pBL1 or pGA1. Other plasmid vectors such as, for example, those based on pCG4 (U.S. Pat. No. 4,489,160) or pNG2 {Serwold-Davis et al., *FEMS Microbiology Letters* 66: 119-124 (1990)} or pAG1 (U.S. Pat. No. 5,158,891), may be employed in the same manner.

Others which are suitable are those plasmid vectors with the aid of which the method of amplifying genes by integration into the chromosome can be applied, as has been described for example by Reinscheid et al. (*Applied and Environmental Microbiology* 60: 126-132 (1994)) for duplicating or amplifying the hom-thrB operon. In this method, the entire gene is cloned into a plasmid vector which is capable of replication in a host (typically *Escherichia coli*), but not in *Corynebacterium glutamicum*. Suitable vectors are, for example, pSUP301 (Simon et al, *Bio/Technology* 1: 784-791 (1983)), pK18mob or pK19mob (Schäfer et al., *Gene* 145: 69-73 (1994)), pGEM-T (Promega Corporation, Madison, Wis., USA), pCR2.1-TOPO (Shuman, *Journal of Biological Chemistry* 269: 32678-84 (1994)), pCR®Blunt (Invitrogen, Groningen, the Netherlands), pEM1 (Schrumpf et al., *Journal of Bacteriology* 173: 4510-4516)) or pBGS8 (Spratt et al., *Gene* 41: 337-342 (1986)). The plasmid vector, which contains the gene to be amplified, is subsequently transferred into the desired *Corynebacterium glutamicum* strain by means of conjugation or transformation. The conjugation method is described for example in Schäfer et al., *Applied and Environmental Microbiology* 60: 756-759 (1994). Transformation methods are described for example in Thierbach et al., *Applied Microbiology and Biotechnology* 29: 356-362 (1988), Dunican and Shivnan, *Bio/Technology* 7: 1067-1070 (1989) and Tauch et al., *FEMS Microbiology Letters* 123: 343-347 (1994). Following homologous recombination by means of a cross-over event, the resulting strain comprises at least two copies of the gene in question.

The wording "an activity of an enzyme $E_x$ which is increased in comparison with its wild type" used hereinabove and in what follows is preferably always understood as meaning an activity of the respective enzyme $E_x$ which is increased by a factor of at least 2, especially preferably of at least 10, more preferably of at least 100, even more preferably of at least 1000 and most preferably of at least 10 000. Furthermore, the genetically modified cell used in the process according to the invention which features "an activity of an enzyme $E_x$ which is increased in comparison with its wild type", in particular also a cell whose wild type features no, or at least no detectable, activity of this enzyme $E_x$ and which only shows a detectable activity of this enzyme $E_x$ after increasing the enzymatic activity, for example by means of overexpression. In this context, the term "overexpression", or the wording "increase in the expression" used in what follows also comprises the case that a starting cell, for example a wild-type cell, features no, or at least no detectable, expression and detectable expression of the enzyme $E_x$ is only induced by recombinant methods.

Accordingly, the wording "reduced activity of an enzyme $E_x$" used hereinbelow is understood as meaning an activity which is preferably reduced by a factor of at least 0.5, especially preferably of at least 0.1, more preferably of at least 0.01, even more preferably of at least 0.001 and most preferably of at least 0.0001. The reduction in the activity of a specific enzyme can be obtained for example by directed mutation, by the addition of competitive or non-competitive inhibitors or by other measures for reducing the expression of a specific enzyme which are known to the skilled worker.

In the case of the enzyme $E_1$, which catalyzes the conversion of succinyl-coenzyme A into methylmalonyl-coenzyme A, this preferably takes the form of a methylmalonyl-coenzyme A mutase (EC 5.4.99.2). This enzyme is preferably encoded by the gene selected from the group consisting of mut, mutA, mutB, sbm, sbmA, sbmB, sbm5, bhbA, mcmA, mcmA1, mcmA2, mcmB, mcm1, mcm2, mcm3, icmA, meaA1 and meaA2. The nucleotide sequence of these genes can be found for example in the "*Kyoto Encyclopedia of Genes and Genomes*" (KEGG database), the databases of the National Center for Biotechnology Information (NCBI) of the National Library of Medicine (Bethesda, Md., USA) or from the nucleotide sequence database of the European Molecular Biologies Laboratories (EMBL, Heidelberg, Germany and Cambridge, UK).

In accordance with an especially preferred embodiment of the first variant of the process according to the invention, the enzyme $E_1$ takes the form of the methylmalonyl-coenzyme A mutase from *Corynebacterium glutamicum* ATCC 13032, which is encoded by a gene with the DNA sequence as shown in SEQ ID No 01 and which has the amino acid as shown in SEQ ID No 02.

Furthermore, it is preferred in accordance with a first alternative of the process according to the invention, where a genetically modified cell is used, in which succinyl-coenzyme A is formed as intermediate and methylmalonate semialdehyde as precursor in the preparation of 3-hydroxyisobutyric acid or of polyhydroxyalkanoates based on 3-hydroxyisobutyric acid, that the genetically modified cell used in accordance with this alternative of the process according to the invention, if appropriate in addition to the increased activity of the enzyme $E_1$, features an activity of at least one of the following enzymes $E_2$ to $E_4$ which is increased in comparison with its wild type (see FIG. 2):

of an enzyme $E_2$, which catalyzes the conversion of methylmalonyl-coenzyme A into methyl malonate;

of an enzyme $E_3$, which catalyzes the conversion of methyl malonate into methylmalonate semialdehyde;

of an enzyme $E_4$ which catalyzes the conversion of methylmalonate semialdehyde into 3-hydroxyisobutyric acid.

In accordance with the invention cells which are especially used are those in which the activity of the following enzymes or enzyme combinations is increased: $E_2$, $E_3$, $E_4$, $E_2E_3$, $E_2E_4$, $E_3E_4$, $E_2E_3E_4$, where $E_2E_3E_4$ is most preferred. Furthermore, it is possible that an enzyme is also capable of catalyzing at least two of the above-described reaction steps. Thus, for example, it is possible to employ an enzyme which features both the activity of enzyme $E_2$ and that of enzyme $E_3$ (and which therefore catalyzes the conversion of methylmalonyl-coenzyme A directly into methylmalonate semialdehyde) such as, for example, the malonyl coenzyme A reductase from *Sulfolobus tokodaii*, which is encoded by the DNA sequence with the SEQ ID No 03 and which has the amino acid sequence as shown in SEQ ID No 04, or else an enzyme which features all three enzymatic activities $E_2$, $E_3$ and $E_4$, such as the malonyl coenzyme A reductase from *Chloroflexus aurantiacus* (Hügler et al., Journal of Bacteriology 184, pages 2404-2410, 2002).

In this context, it is especially preferred that the enzyme $E_2$ is a methylmalonyl-coenzyme A hydrolase (EC 3.1.2.17), $E_3$ is an aldehyde dehydrogenase (EC 1.2.1.3) or an aldehyde oxidase (EC 1.2.3.1) and $E_4$ is a 3-hydroxyisobutyrate dehydrogenase (EC 1.1.1.31) or a 3-hydroxyacyl-coenzyme A dehydrogenase (EC 1.1.1.35).

The enzyme $E_2$ is preferably encoded by the aox1 gene. The methylmalonyl-coenzyme A hydrolase from rat liver is described for example in Kovachy et al., "Recognition, isolation, and characterization of rat liver D-methylmalonyl coenzyme A hydrolase", *J. Biol. Chem.* 258 (1983), pages 11415-11421.

The enzyme $E_3$ is preferably encoded by genes selected from the group consisting of aldh2, aldh3a1, aldh3a2, aldh1b1, aldh1a1, aldh7a1, aldh1a4, aldh1a1, aldh1a2, mgc80785, mgc83352, mgc89020, dmel-CG31075, cg3752, cg9629, alh-9, alh-1, alh-2, f5O8.35, t7O23.15, f15I1.19, tT17F15.130, ald1, ald2, ald4, ald5, ald6, ac1044Wp, adr417wp, msc7, tb06.5F5.780, aldH, puuC, putA, aldA, badH, alkH, pcD, rsp1591, rs01031, exaC, acoD, dhaL, pchA, aldB, dhaS, betB, ywdH, ycbD, aldX, aldY, aldA1, aldA2, aldC, pcd, cg10546, cg12668, cg12796, scg11A.05, sci30A.27c, sce9.27c, sck13.05c, sc5H4.03, thcA, gabD2, alkH, aldH, aldH1, aldY1, aldY2, aldY3, aldY4, aldY5, aldY6, aldY7 and aldhT.

Suitable genes for the enzyme $E_4$ are selected from the group consisting of hibadh, cg15093, cg15093, cg4747, mwL2.23, t13k14.90, f19b15.150, hibA, ygbJ, mmsB, mmsB, garR, tsar, mmsB-1, mmsB-2, yfjR, ykwC, ywjF, hibD, glxR, SCM1.40c, hibD, ehhand, hadh2, hadhsc, hsd17B4, loc488110, had, mgC81885, hadh2-prov, cg3415, cg7113, ech-1, ech-8, ech-9, ard-1, yfcX, fadB, faoA, fadB2x, hbd-1, hbd-2, hbd-3, hbd-4, hbd-5, hbd-6, hbd-7, hbd-8, hbd-9, hbd-10, fadJ, rs04421, rs02946, rs05766, bbsD, bbsC, fadB1, fadB2, fadB5, hbdA, pimF, fabJ-1, fabJ, scbac19f3.11, sci35.13, scbac8d1.10c, sc5f2a.15, sc6a5.38, fadC2, fadC4, fadC5, fadC6, had and paaH. Further suitable 3-hydroxyisobutyrate dehydrogenases are described for example in Bannerjee et al. (1970), *J. Biol. Chem*, 245, pages 1828 to 1835, Steele et al. (1992), *J. Biol. Chem.*, 267, pages 13585 to 13592, Harris et al. (1988), *J. Biol. Chem.*, 263, pages 327 to 331, Harris et al., *Biochim. Biophys. Acta*, 1645 (1), pages 89 to 95, Hawes et al. (2000), *Methods Enzymol.*, 324, pages 218 to 228, Harris et al., *J. Biol. Chem.*, 275 (49), pages 38780 to 38786, Rougraff et al. (1988), *J. Biol. Chem.*, 263(1), pages 327 to 331, Robinson et al., *J. Biol. Chem.*, 225, pages 511 to 521, Hawes et al. (1995), *Biochemistry*, 34, pages 4231 to 4237, Hasegawa J. (1981), *Agric. Biol. Chem.*, 45, pages 2805 to 2814, Hawes et al. (1996), *FEES Lett.*, 389, pages 263 to 267, Hawes et al. (1996), *Enzymology and Molecular Biology of Carbonyl Metabolism*, Plenum Press, New York, pages 395 to 402, Adams et al. (1994), *Structure*, 2, pages 651 to 668, Zhang et et. (1999), *Biochemistry*, 38, pages 11231 to 11238, Mirny et al., (1999), *J. Mol. Biol.*, 291, pages 177 to 196 and Lokanath et al. (2005), *J Mol Biol*. The disclosure of these publications is hereby incorporated by reference and forms part of the disclosure of the present invention.

The nucleotide sequences of the abovementioned genes and of further genes for the enzymes $E_2$ to $E_4$ can also be found in the KEGG database, the NCBI database or the EMBL database, inter alia.

In accordance with an especially preferred embodiment of this alternative of the process according to the invention, in which a genetically modified cell is used, where succinyl-coenzyme A is formed as intermediate and methylmalonate semialdehyde as precursor in the preparation of 3-hydroxy-isobutyric acid or of polyhydroxyalkanoates based on 3-hydroxyisobutyric acid, it is preferred that the malonyl coenzyme A reductase from *Sulfolobus tokodaii*, which is encoded by the DNA sequence with the SEQ ID No 03 and which has the amino acid sequence as shown in SEQ ID No 04, is employed for the conversion of methylmalonyl-coenzyme A into methylmalonate semialdehyde. In accordance with another especially preferred embodiment of this variant, the malonyl coenzyme A reductase from *Chloroflexus aurantiacus* (Hügler et al., Journal of Bacteriology 184, pages 2404-2410, 2002) is employed for the conversion of methylmalonyl-coenzyme A into 3-hydroxyisobutyric acid.

Furthermore, it is preferred in the context of this first alternative of the first special embodiment of the process according to the invention that the genetically modified cell used in accordance with this embodiment features an activity of an enzyme $E_5$, which features the conversion of methylmalonate semialdehyde into propionyl-coenzyme A, which is reduced in comparison with its wild type, this enzyme preferably taking the form of a methylmalonate-semialdehyde dehydrogenase (EC 1.2.1.27).

In accordance with a second alternative of the process according to the invention, in which a genetically modified cell is used where succinyl-coenzyme A is formed as intermediate and methylmalonate semialdehyde as precursor in the preparation of 3-hydroxyisobutyric acid or of polyhydroxyalkanoates based on 3-hydroxyisobutyric acid, it is preferred that the cell, if appropriate in addition to the increased activity of the enzyme $E_1$, features an activity of at least one of the following enzymes $E_4$ to $E_7$ which is increased in comparison with its wild type (see FIG. 3):

of an enzyme $E_6$, which catalyzes the conversion of (R) methylmalonyl-coenzyme A into (S) methylmalonyl-coenzyme A;

of an enzyme $E_7$, which catalyzes the conversion of (S) methylmalonyl-coenzyme A into propionyl-coenzyme A;

of an enzyme $E_5$, which catalyzes the conversion of propionyl-coenzyme A into methylmalonate semialdehyde;

of an enzyme $E_4$, which catalyzes the conversion of methylmalonate semialdehyde into 3-hydroxyisobutyric acid.

Cells which are especially preferably used in accordance with the invention are those in which the activity of the following enzymes or enzyme combinations is increased: $E_4$, $E_5$, $E_6$, $E_7$, $E_7$, $E_4E_5$, $E_4E_6$, $E_4E_7$, $E_5E_6$, $E_5E_7$, $E_6E_7$, $E_4E_5E_6$, $E_4E_5E_7$, $E_4E_6E_7$, $E_5E_6E_7$ and $E_4E_5E_6E_7$, with $E_4E_5E_6E_7$ being most preferred.

In this context, it is especially preferred that the enzyme $E_6$ is a methylmalonyl-coenzyme A epimerase (EC 5.1.99.1)

$E_7$ is a methylmalonyl-coenzyme A decarboxylase (EC 4.1.1.41), $E_5$ is a methylmalonate-semialdehyde dehydrogenase (EC 1.2.1.27), and $E_4$ is a 3-hydroxyisobutyrate dehydrogenase (EC 1.1.1.31) or a 3-hydroxyacyl-coenzyme A dehydrogenase (EC 1.1.1.35).

In this context, preferred enzymes $E_4$ are those which have already been mentioned above in the context of the first variant of the first preferred embodiment of the process according to the invention.

The enzyme $E_6$ is preferably encoded by the mcee gene. A suitable methylmalonyl-coenzyme A decarboxylase (enzyme $E_7$) is described, for example, by Benning et al. in Biochemistry, Vol. 39 (2000), pages 4630-4639.

Suitable genes for the enzyme $E_5$ are preferably selected from the group consisting of aldh6a1, cg17896, t22c12.10, ald6, putA1, mmsA, mmsA-1, mmsA-2, mmsA-3, mmsA-4, msdA, iolA and iolAB.

Suitable genes for the enzyme $E_7$ are preferably selected from the group consisting of mmdA, bcc, oadB, oadB2, oadB3, SC1C2.16, SC1G7.10, pccB1, accA2, mmdB, mmdC and ppcB.

The nucleotide sequences of the abovementioned genes for the enzymes $E_5$, $E_6$ and $E_7$ may, inter alia, also be found in the KEGG database.

In accordance with a third alternative of the process according to the invention, in which a genetically modified cell is used, where succinyl-coenzyme A is formed as intermediate and methylmalonate semialdehyde as precursor in the preparation of 3-hydroxyisobutyric acid or of polyhydroxyalkanoates based on 3-hydroxyisobutyric acid, it is preferred that the cell, if appropriate in addition to the increased activity of the enzyme $E_1$, features an activity of at least one of the following enzymes $E_4$, $E_5$ and $E_7$ which is increased in comparison with its wild type (see FIG. 4):

of an enzyme $E_7$, which catalyzes the conversion of methylmalonyl-coenzyme A into propionyl-coenzyme A;

of an enzyme $E_5$, which catalyzes the conversion of propionyl-coenzyme A into methylmalonate-semialdehyde;

of an enzyme $E_4$, which catalyzes the conversion of methylmalonate-semialdehyde into 3-hydroxyisobutyric acid.

This pathway corresponds essentially to the second variant of the first preferred embodiment of the process according to the invention, but, as opposed to the second variant, propionyl-CoA is prepared directly from methylmalonyl-coenzyme A. Preferred enzymes and genes for the enzymes $E_4$, $E_5$ and $E_7$ are those genes or enzymes which have already been mentioned above in connection with the second variant.

Furthermore, it may in accordance with the first special embodiment of the process according to the invention (and also in accordance with all embodiments which are still to be described hereinbelow) also be preferred to use a genetically modified cell which is capable of converting the formed 3-hydroxyisobutyric acid into a polyhydroxy-alkanoate. Such polyhydroxyalkanoates are deposited intracellularly by many microorganisms in the form of highly refractive granula. In this context, it is especially preferred that the genetically modified cell used in the process according to the invention features an activity of at least one of, preferably of the two, the following enzymes $E_8$ and $E_9$ which is increased in comparison with its wild type (see FIG. 5):

of an enzyme $E_8$, which catalyzes the conversion of 3-hydroxyisobutyric acid into 3-hydroxyisobutyryl-coenzyme A;

of an enzyme $E_9$, which catalyzes the conversion of 3-hydroxyisobutyryl-coenzyme A to a polyhydroxy-alkanoate based on 3-hydroxyisobutyric acid.

In this context, it is especially preferred that the enzyme $E_8$ is a 3-hydroxyisobutyryl CoA hydrolase (EC 3.1.2.4) and $E_9$ is a polyhydroxyalkanoate synthase.

As has already been explained above, the first preferred embodiment of the process according to the invention generates 3-hydroxyisobutyric acid or the polyhydroxyalkanoates based on 3-hydroxyisobutyric acid from succinyl coenzyme A as intermediate and from methylmalonate semialdehyde as precursor. Here, it may make sense in principle to influence not only one or more of the abovementioned enzyme activities $E_1$ to $E_9$, but also those enzyme activities which lead to an increased formation of succinyl-coenzyme A in the cell.

In the event that, according to the first special embodiment of the first variant of the process according to the invention, the formation of 3-hydroxyisobutyric acid or of the polyhydroxyalkanoates based on 3-hydroxy-isobutyric acid takes place from carbohydrates or glycerol via succinyl-coenzyme A as intermediate and methylmalonate semialdehyde as precursor, it is, according to a special embodiment of the above-described first, second or third alternative of the process according to the invention, preferred that the genetically modified cell used features an activity of at least one of the, preferably of the two, following enzymes $E_{10}$ and $E_{11}$ which is increased in comparison with its wild type (see FIG. 6):

of an enzyme $E_{10}$, which catalyzes the conversion of phosphoenolpyruvate into oxaloacetate;

of an enzyme $E_{11}$, which catalyzes the conversion of pyruvate into oxaloacetate.

In this context, it is especially preferred that the enzyme $E_{10}$ is a phosphoenolpyruvate carboxylase (EC 4.1.1.31) and $E_{11}$ is a pyruvate carboxylase (EC 6.4.1.1).

The enzyme $E_{10}$ is preferably encoded by the genes selected from the group consisting of f12 m16.21, f14n22.13, k15 m2.8, ppc, clpA, pepC, capP, cgl1585, pepC, pck ppc and pccA, where the ppc gene is especially preferred. Phosphoenolpyruvate carboxylases which are preferred according to the invention are also described in particular in U.S. Pat. No. 4,757,009, U.S. Pat. No. 4,980,285, U.S. Pat. No. 5,573,945, U.S. Pat. No. 6,872,553 and U.S. Pat. No. 6,599,732. As regards phosphoenol-pyruvate carboxylases, the disclosure content of these publications is hereby incorporated by reference and forms part of the disclosure of the present invention.

The enzyme $E_{11}$ is preferably encoded by the genes selected from the group consisting of pc, pcx, cg1516, cgl1516, pyc-1, pyc-2, aar162 Cp, pyr1, accC-2, pycA, pycA2, pca, cgl0689, pyc, pycB, accC, oadA, acc and accC1, where the pyc gene is especially preferred. Pyruvate carboxylases which are preferred according to the invention are also described in particular in U.S. Pat. No. 6,455,284, U.S. Pat. No. 6,171,833, U.S. Pat. No. 6,884,606, U.S. Pat. No. 6,403, 351, U.S. Pat. No. 6,852,516 and U.S. Pat. No. 6,861,246. A further pyruvate carboxylase which is especially preferred according to the invention is that mutant which is described in "*A novel methodology employing Corynebacterium glutamicum genome information to generate a new L-lysine-producing mutant*", Ohnishi J et al., Applied Microbiology and Biotechnology, Vol. 58 (2), pages 217-223 (2002).

The nucleotide sequences of suitable genes of the enzymes $E_{10}$ and $E_{11}$ can be found in the KEGG database, the NCBI database or the EMBL database.

Starting from the oxaloacetate intermediate stage, there are several possibilities for arriving at succinyl-coenzyme A, which can then be converted into 3-hydroxyisobutyric acid via methylmalonyl-coenzyme A by means of the three variants mentioned at the outset.

A first pathway leads via fumarate as intermediate. In this case it is preferred in accordance with a first special embodiment of the above-described first, second or third alternative of the process according to the invention, where a genetically modified cell is used in which methylmalonate-semialdehyde is formed as precursor and succinyl-coenzyme A as intermediate, that the cell, if appropriate additionally to an increased activity of the enzyme $E_{10}$ or $E_{11}$, features an activity of at least one of the following enzymes $E_{12}$ to $E_{15}$ which is increased in comparison with its wild type (see FIG. 7):

of an enzyme $E_{12}$, which catalyzes the conversion of oxaloacetate into malate;

of an enzyme $E_{13}$, which catalyzes the conversion of malate into fumarate;

of an enzyme $E_{14}$, which catalyzes the conversion of fumarate into succinate;

of an enzyme $E_{15}$, which catalyzes the conversion of succinate into succinyl-coenzyme A.

In accordance with the invention, cells which are especially used are those in which the activity of the following enzymes or enzyme combinations is increased: $E_{12}$, $E_{13}$, $E_{14}$, $E_{15}$, $E_{12}E_{13}$, $E_{12}E_{14}$, $E_{12}E_{15}$, $E_{13}E_{14}$, $E_{13}E_{15}$, $E_{14}E_{15}$, $E_{12}E_{13}E_{14}$, $E_{12}E_{13}E_{15}$, $E_{12}E_{14}E_{15}$, $E_{13}E_{14}E_{15}$, $E_{12}E_{13}E_{14}E_{15}$, with $E_{12}E_{13}E_{14}E_{15}$ being most preferred.

In this context, it is especially preferred that the enzyme $E_{12}$ is a malate dehydrogenase (EC 1.1.1.37) or a malate quinone oxidoreductase (1.1.99.16), $E_{13}$ is a fumarate hydratase (EC 4.2.1.2), $E_{14}$ is a succinate dehydrogenase (EC 1.3.99.1 or EC 1.3.5.1) or a succinate quinone oxidoreductase (1.3.5.1), and $E_{15}$ is a succinate coenzyme A ligase (EC 6.2.1.4 or EC 6.2.1.5).

The enzyme $E_{12}$ is preferably encoded by genes selected from the group consisting of mdh1, mdh2, mor1, cg10748, cg10749, cg5362, mdh-1, f46e10.10, f19p19.13, f12 m16.14, t30120.4, k15m2.16, f1p2.70, f17i14.150, mnl12.18, mik19.17, mdh3, adl164 cp, adr152 cp, adr252wp, mdhA, mdhC, mdhB, ybiC, mdh, yiaK, ybiC, allD, citH, yjmC, citH, cg12380, ldh, sqdB, mqo, yojH, mqoA, mqoB, mqo1, mqo2, mqo3, mqo4 and cgl2001, where the mqo gene and the mdh gene are especially preferred.

The enzyme $E_{13}$ is preferably encoded by genes selected from the group consisting of fh, fh1, sc4094, sc4095, t30b22.19, k3k7.11, acr013/cp, fum1, fum2, fum3, fum4, fumH, fumA, fumB, fumC, fumC1, fumC2, fum, ttdA, ttdB, fumB-alpha, fumB-beta, citG, citB, fumX, fum-1 and fum-2, where the fum gene is especially preferred.

The enzyme $E_{14}$ is preferably encoded by genes selected from the group consisting of sdh1, sdh2, sdh3, sdh4, sdh5, sdh6, osm1, osm2, sdhA, sdhB, sdhC, sdhD, frdA, frdB, frdC, frdD, ifcA-1, ifcA-2, sdhB-1, sdhB-2, frdC2, cgl0370, cgl0371, cgl0372, scm10.10c, scm10.11c, scm10.12c, sc5g8.25c, sc5g8.26c, scbac-31e11.02c, scbac31e11.02c, sc4b10.10c, sdhA2, sdhB2, sdhA1, sdhB1, qcrB2, sdhA3, sdhB3, frdB1 and frdB2, where the genes sdhA, sdhB and sdhC are especially preferred.

The enzyme $E_{15}$ is preferably encoded by genes selected from the group consisting of suclg1, suclg2, loc434885, cg10622, dmel-CG6255, f11a3.3, f8l15.30, mkd15.11, lsc1, lsc2, ael211wp, afr134 cp, scsA, scsB, sucC and sucD.

Again, the nucleotide sequences of suitable genes of the enzymes $E_{12}$ to $E_{15}$, can also be found in the KEGG database, the NCBI database or the EMBL database.

In the event that the activity of one or more of the enzymes $E_{12}$ to $E_{15}$ is increased, it may also prove advantageous that the cell features an activity of one of the following enzymes $E_{16}$ to $E_{23}$ which is reduced in comparison with its wild type:

of an enzyme $E_{16}$, which catalyzes the conversion of oxaloacetate into citrate;

of an enzyme $E_{17}$, which catalyzes the conversion of malate into oxaloacetate;

of an enzyme $E_{18}$, which catalyzes the conversion of succinyl-coenzyme A into succinate, of an enzyme $E_{19}$, which catalyzes the conversion of oxaloacetate into phosphoenolpyruvate, of an enzyme $E_{20}$, which catalyzes the conversion of oxaloacetate into pyruvate, of an enzyme $E_{21}$, which catalyzes the conversion of oxaloacetate into aspartate, of an enzyme $E_{22}$, which catalyzes the conversion of malate into pyruvate, of an enzyme $E_{23}$, which catalyzes the conversion of pyruvate into acetate.

Cells which are especially preferred in accordance with the invention are those in which the activity of the following enzymes or enzyme combinations is reduced: $E_{16}$, $E_{17}$, $E_{18}$/$E_{19}$, $E_{20}$, $E_{21}$, and $E_{16}E_{17}E_{18}E_{19}E_{20}E_{21}E_{22}E_{23}$.

In this context, it is especially preferred that the enzyme $E_{16}$ is a citrate synthase (EC 2.3.3.1 or EC 2.3.3.8), $E_{17}$ is a malate oxidase (EC 1.1.3.3), $E_{18}$ is a succinyl CoA hydrolase (EC 3.1.2.3), $E_{19}$ is a phosphoenolpyruvate carboxykinase (EC 4.1.1.49 or 4.1.1.32), $E_{20}$ is an oxaloacetate decarboxylase (EC 4.1.1.3), $E_{21}$ is an aspartate transaminase (EC 2.6.1.1), $E_{22}$ is a malate dehydrogenase (EC 1.1.1.38, EC 1.1.1.39 or EC 1.1.1.40), $E_{23}$ is a pyruvate dehydrogenase (EC 1.2.1.51).

The enzyme $E_{16}$ is preferably encoded by genes selected from the group consisting of glt, cs, csl, cg3861, cts-1, f7f19.21, f4i1.16, t20n10.90, t20n10.100, t2O9.80, cit1, cit2, cit3, aar004 cp, agr002wp, cshA, gltA, citZ, cit, prpC, cisY, cis, mmgD, citA, gltA1, gltA2, gltA3, cg10829, prpC1, scd10.20, citA1, citA2, citA3, acly, cg8322, f5e6.2, k7jJ8.14 and citE, where gltA is most preferred.

The enzyme $E_{19}$ is preferably encoded by genes selected from the group consisting of pckA, pck1, pck2, cg10924, cg17725, cg17725, pckG, ppcK, cgl2863, pck and 2sck36.02.

The enzyme $E_{20}$ is preferably encoded by genes selected from the group consisting of oadA, oadB, oadC, oadG, oag3, eda, dcoA, oadA1, oadA2, pycB and mmdB.

The enzyme $E_{21}$ is preferably encoded by genes selected from the group consisting of myn8.7, glt1, adr290wp, gltB, gltD, glt1, gls1, gltA, glt, glxD, gltD1, gltD2, gdh2, agl040 Cp, gdhA1, gdhA, gdhA2, gluD, gluD1, gluD2, rocG, ypcA, gudB, t11i18.2, t2i1.150, mrg7.13, f19c24.7, gdh, gdh1, gdh2, gdh3, got1, got2, cg4233, cg8430, f23n19.17, f13j11.16, t26c19.9, f7f1.18, F10N7.200, t16l1.170, f15n18.110, t20d1.70, aat1, aat2, abl038wp, afr211 cp, agx1, bna4, aatA, aatB, ybdL, aspC, yfbQ, aat, avtA1, avtA2, tyrB, avtA, avtB, argD1, argD2, aspB1, aspB2, aspB3, aspB, aspC1, aspC2, aspC3, aspC4, RS05143, aspAT, ywfG, yhdR, argD, mtnV, alaT, hisC, avtA1, avtA2, avtA3, cgl0240, cgl1103, cgl2599, cgl2844, 2sck36.07c, sc9e12.21, sc2h4.04c, tyrB, gtp, gtp1, gtp2, cg1640, f20d23.34, f26f24.16, f24j13.15, t10d10.20 and agr085wp, where aspC, aatA, gdh, gudB, gdhA, gltB and gltD are especially preferred.

The enzyme $E_{21}$ is preferably by genes selected from the group consisting of myn8.7, glt1, adr290wp, gltB, gltD, glt1, gls1, gltA, glt, glxD, gltD1, gltD2, gdh2, agl040 Cp, gdhA1, gdhA, gdhA2, gluD, gluD1, gluD2, rocG, ypcA, The enzyme $E_{22}$ is preferably encoded by genes selected from the group consisting of me, me1, me2, me3, mae, mae1, mae2, sfcA, sfcA1, maeA, maeB, tme, yqkJ, ywkA, yqkJ, malS, ytsJ, mleA, mleS, mez, sce59.10c, 2sc7g11.23, malS1, malS2, dme, maeB1, maeB2, mdh, mdh1, mdh2, dmel_cgl0120, dmel_cg10120, dmel-cg5889, f19k16.27, f6f22.7, t22p22.60, f18a17.1, mod1, tme, mao, cgl3007, malS and malE.

The enzyme $E_{23}$ is preferably encoded by genes selected from the group consisting of me, me1, me2, me3, mae, mae1, mae2, sfcA, sfcA1, maeA, maeB, tme, yqkJ, ywkA, yqkJ, malS, ytsJ, mleA, mleS, mez, sce59.10c, 2sc7g11.23, malS1, malS2, dme, maeB1, maeB2, mdh, mdh1, mdh2, dmel_cg10120, dmel_cg10120, dmel-cg5889, f19k16.27, f6f22.7, t22p22.60, f18a17.1, mod1, tme, mao, cgl3007, malS and malE.

Furthermore, it is preferred in accordance with the invention that, in the event where the increased provision of succinyl-coenzyme A in the cell takes place by means of the above-described pathway (oxaloacetate→malate→fumarate→succinyl-coenzyme A), the provision of reduction equivalents in the cell is also increased in a targeted manner.

One possibility of increasing the reduction equivalents consists in increasing the oxidative pentose phosphate pathway. In this context, it is especially preferred that the activity of glucose 6-phosphate dehydrogenase (EC 1.1.1.49) and/or of 6-phosphogluconate dehydrogenase (EC 1.1.1.44), which is preferably encoded by the gnd gene, is increased while, if appropriate, simultaneously inhibiting glycolysis, for example by lowering the activity of glucose 6-phosphate isomerase, as described in WO-A-01/07626. In addition to, or instead of, the directed promotion of the pentose phosphate pathway, it may furthermore be preferred to provide reduction equivalents by supplying, to the cells, ethanol as the carbon source and by promoting, in the cells, the conversion of the ethanol into acetaldehyde by means of alcohol dehydrogenases (EC 1.1.1.1, EC 1.1.1.2, EC 1.1.1.71 or EC 1.1.99.8) and the further conversion of the acetaldehyde into acetyl coenzyme A by means of acetaldehyde dehydrogenases (EC 1.2.1.10). Again, suitable genes for alcohol dehydrogenases and acetaldehyde dehydrogenases, can be found in gene databases which are known to the skilled worker, such as, for example, the KEGG database, the NCBI database or the EMBL database.

A second pathway from oxaloacetate to succinyl-coenzyme A leads via citrate as intermediate. In this case, it is preferred in accordance with a second special embodiment of the above-described first, second or third alternative of the process according to the invention to use a genetically modified cell, if appropriate in addition to an increased activity of the enzyme $E_{10}$ or $E_{11}$, features an activity of at least one of the following enzymes $E_{13}$ to $E_{16}$ and $E_{24}$ to $E_{26}$ which is increased in comparison with its wild type (see FIG. 8):

of an enzyme $E_{16}$, which catalyzes the conversion of oxaloacetate into citrate;

of an enzyme $E_{24}$, which catalyzes the conversion of citrate into isocitrate;

of an enzyme $E_{25}$, which catalyzes the conversion of isocitrate into glyoxalate and succinate;

of an enzyme $E_{26}$, which catalyzes the conversion of glyoxalate into malate;

of an enzyme $E_{13}$, which catalyzes the conversion of malate into fumarate;

of an enzyme $E_{14}$, which catalyzes the conversion of fumarate into succinate;

of an enzyme $E_{15}$, which catalyzes the conversion of succinate into succinyl-coenzyme A.

In this context, cells which are especially preferred in accordance with the invention are those in which the activity of the following enzymes or enzyme combinations is increased: $E_{13}$, $E_{14}$, $E_{15}$, $E_{16}$, $E_{24}$, $E_{25}$, $E_{26}$, $E_{13}E_{14}$, $E_{13}E_{15}$, $E_{13}E_{16}$, $E_{13}E_{24}$, $E_{13}E_{25}$, $E_{13}E_{26}$, $E_{14}E_{15}$, $E_{14}E_{16}$, $E_{14}E_{24}$, $E_{14}E_{25}$, $E_{14}E_{26}$, $E_{15}E_{16}$, $E_{15}E_{24}$, $E_{15}E_{25}$, $E_{15}E_{26}$ and $E_{13}E_{14}E_{15}E_{16}E_{24}E_{25}E_{26}$, where $E_{13}E_{14}E_{15}E_{16}E_{24}E_{25}E_{26}$ is most preferred.

In this context, it is especially preferred that the enzyme $E_{13}$ is a fumarate hydratase (EC 4.2.1.2), $E_{14}$ is a succinate dehydrogenase (EC 1.3.99.1 or EC 1.3.5.1) or a succinate quinone oxidoreductase (1.3.5.1), $E_{15}$ is a succinate coenzyme A ligase (EC 6.2.1.4 or EC 6.2.1.5), $E_{16}$ is a citrate synthase (EC 2.3.3.1 or EC 2.3.3.8), $E_{24}$ is an aconitate hydratase (EC 4.2.1.3), $E_{25}$ is an isocitrate lyase (EC 4.1.3.1) and $E_{26}$ is a malate synthase (EC 2.3.3.9).

Preferred genes for the enzymes $E_{13}$ to $E_{16}$ are those which have already been described above in connection with the first pathway from oxaloacetate to succinyl-coenzyme A.

The enzyme $E_{24}$ is preferably encoded by genes selected from the group consisting of aco1, aco2, ratireb, dmel-CG4706, dmel-CG4900, dmel-cg6342, cg9244, t3p4.5, f10m23.310, f4b14.100, adl032Wp, afr629wp, acnA, acnB, acnC, acnD, rpfA, acnA1, acnA2, acnM, citB, leuC, cgl1540, sacA, can and aco, where acnA and acnB are especially preferred.

The enzyme $E_{25}$ is preferably encoded by genes selected from the group consisting of msd21.4, icl1, icl2, adl066 cp, agl057wp, aceA, icl, aceAa, aceAb, cgl0097 and cgl2331, where aceA is especially preferred. In accordance with a particular embodiment, genes which are preferred are those which code for an isocitrate lyase which is deregulated at the gene level or protein level.

The enzyme $E_{26}$ is preferably encoded by genes selected from the group consisting of med24.5, mlsS1, acr268 cp, masA, glcB, aceB, mls, glcB-1, glcB-2, cgl2329, masZ, aceB1, aceB2 and mas, where the aceB gene is especially preferred.

Again, the nucleotide sequences of suitable genes of the enzymes $E_{24}$ to $E_{26}$ can be found in the KEGG database, the NCBI database or the EMBL database.

When the provision of oxaloacetate from phosphoenolpyruvate or from pyruvate is promoted by increasing the activity of the enzyme $E_{10}$ or $E_{11}$, the succinate which is formed, besides glyoxalate, upon cleavage of the isocitrate by the isocitrate lyase may also be utilized for the formation of succinyl-coenzyme A. Furthermore, it may be advantageous in this second pathway from the oxaloacetate to the succinate to reduce the activity of an enzyme $E_{27}$, which catalyzes the conversion of isocitrate into 2-oxoglutarate and which preferably takes the form of an isocitrate dehydrogenase (EC 1.1.1.41 or EC 1.1.1.42). Preferably, the isocitrate dehydrogenase takes the form of an enzyme which is encoded by a gene selected from the group consisting of idh1, idh2, cg7176, cg7176, cg7176, f20d21.16, f12p19.10, t15n1.80, idp1, idp2, idp3, aal022Wp, aer061Cp, idhC, idhM, icdA, icd, idh, icd1, icd2, leuB, citC, citC, cgl0664, leuB2, idh3A, idg3B, idh3G, cg12233, dmel-CG5028, dmel-CG6439, f6p23.14, f23e12.180, f8d20.160, f12e4.20, adl223wp and afr137 cp, where icdA and citC are especially preferred.

A third pathway from the oxaloacetate to the succinyl-coenzyme A leads via 2-oxoglutarate as intermediate. In this case, it is preferred in accordance with a third special embodiment of the above-described first, second or third alternative of the process according to the invention to use a genetically modified cell featuring an activity of at least one of the following enzymes $E_{16}$, $E_{24}$, $E_{27}$ and $E_{28}$ which is increased in comparison with its wild type, if appropriate in addition to an increased activity of the enzyme $E_{10}$ or $E_{11}$ (see FIG. 9):

of an enzyme $E_{16}$, which catalyzes the conversion of oxaloacetate into citrate;

of an enzyme $E_{24}$, which catalyzes the conversion of citrate into isocitrate;

of an enzyme $E_{27}$, which catalyzes the conversion of isocitrate into 2-oxoglutarate;

of an enzyme $E_{28}$, which catalyzes the conversion of 2-oxoglutarate into succinyl-coenzyme A.

In this context, cells which are especially preferred in accordance with the invention are those in which the activity of the following enzymes or enzyme combinations is increased: $E_{16}$, $E_{24}$, $E_{27}$, $E_{28}$, $E_{16}E_{24}$, $E_{16}E_{27}$, $E_{16}E_{28}$, $E_{24}E_{27}$, $E_{24}E_{28}$, $E_{27}E_{28}$, $E_{16}E_{24}E_{27}$, $E_{16}E_{24}E_{28}$, $E_{24}E_{27}E_{28}$ and $E_{16}E_{24}E_{27}E_{28}$, where $E_{16}E_{24}E_{27}E_{28}$ is most preferred.

In this context, it is especially preferred that the enzyme $E_{16}$ is a citrate synthase (EC 2.3.3.1 or EC 2.3.3.8), $E_{24}$ is an aconitate hydratase (EC 4.2.1.3), $E_{27}$ is an isocitrate dehydrogenase (EC 1.1.1.41 or EC 1.1.1.42) and $E_{28}$ is a 2-oxoglutarate synthase (EC 1.2.7.3).

Preferred genes for the enzymes $E_{16}$, $E_{24}$ and $E_{27}$ are those which have already been described above in connection with the first and second pathway from the oxaloacetate to the succinyl-coenzyme A.

The enzyme $E_{28}$ is preferably encoded by genes selected from the group consisting of korA, korB, kor D, korA1, korA2, korB1, korB2, oorA, oorB, oorC, oorD, oforA, oforB, porA, porB, porA1, porA2, porA3, porA4, porG, porG1, porG2, porB1, porB2, porB3, SCD20.12c, SCD20.13c, SCAH10.34c, SCAH10.35c, korG, or A, or B, korG1 and korG2. Furthermore, $E_{28}$ may also take the form of a dehydrogenase complex consisting of a plurality of subunits which have different enzymatic activities. In particular, it may take the form of a dehydrogenase complex comprising an oxoglutarate dehydrogenase (EC 1.2.4.2), a dihydrolipoyl dehydrogenase (EC 1.8.1.4) and a dihydrolipoyllysine-residue succinyl transferase (EC 2.3.1.61). In this context, the oxoglutarate dehydrogenase (EC 1.2.4.2) is preferably encoded by genes selected from the group consisting of ogdh, ghdhl, loc239017, mgc68800, mgc80496, cgl1661, t22e16.70, mpA24.10, kgd1, aer374 cp, sucA, odhA, kgdA and cgl1129, where sucA and odhA are especially preferred. The dihydrolipoyl dehydrogenase (EC 1.8.1.4) is preferably encoded by genes selected from the group consisting of dld, dld-prov, dldh, cg7430, t2j15.6, k14a17.6, at3g17240, mgd8.71pd1, afr512wp, dld1, lpd, tb03.26j7.650, tb04.3 m17.450, tb927.8.7380, tb08.10 k10.200, lpdA, lpdG, lpdV, lpd3, acoD, lpdA1, lpdA2, lpdA3, odhL, pdhD, pdhD1, pdhD2, pdhD3, pdhD42, lpdAch1, lpdAch2, lpdAc, acoL, bfmbC, bkdD, cgl0366, cgl0688, scm1.17c, pdhL, sck13.11, lpdB2 and dld1, where lpd is especially preferred. In this context, the dihydrolipoyllysine-residue succinyl transferase (EC 2.3.1.61) is preferably encoded by genes selected from the group consisting of dlst, dlst-prov, mgc89125, dmel_CG5214, f10m23.250, k13p22.8, kgd2agl200wp, kgd2, odhB, sucB, aceF, kgdB, sucB1, sucB2, pdhC, dlaT, kgd, sc5F7.20 and sc4B10.24c, where sucB and odhB are especially preferred.

The nucleotide sequences of suitable genes of the enzyme $E_{28}$ or of the abovementioned subunits of the enzyme $E_{28}$, can, again, be found in the KEGG database, the NCBI database or the EMBL database.

The above-described pathways from the oxaloacetate to the succinyl-coenzyme A depart from phosphoenolpyruvate or from pyruvate as substrate precursors. In this context, it may furthermore be preferred to genetically modify the cells in such a way that they are capable of providing especially large amounts of pyruvate or phosphoenolpyruvate starting from carbohydrates and/or from glycerol.

In the event that the cells are capable of utilizing glycerol as nutrient source, it is preferred that the genetically modified cell used in the process according to the invention displays an activity of at least one, preferably all, of the following enzymes $E_{29}$ to $E_{42}$ which is increased in comparison with its wild type:

- of an enzyme $E_{29}$, which facilitates the diffusion of glycerol into the cell,
- of an enzyme $E_{30}$, which catalyzes the conversion of glycerol into glycerol 3-phosphate,
- of an enzyme $E_{31}$, which catalyzes the conversion of glycerol 3-phosphate into dihydroxyacetone phosphate,
- of an enzyme $E_{32}$, which catalyzes the transfer of sulfur to the sulfur acceptor thioredoxin 1,
- of an enzyme $E_{33}$, which catalyzes the hydrolysis of phospholipids with formation of alcohols and glycerol,
- of an enzyme $E_{34}$, which catalyzes the transport of glycerol 3-phosphate into the cell in exchange for phosphate;
- of an enzyme $E_{35}$, which catalyzes the conversion of dihydroxyacetone phosphate into glyceraldehyde 3-phosphate,
- of an enzyme $E_{36}$, which catalyzes the conversion of glyceraldehyde 3-phosphate into 1,3-biphosphoglycerate,
- of an enzyme $E_{37}$, which catalyzes the conversion of 1,3-biphosphoglycerate into 3-phosphoglycerate,
- of an enzyme $E_{38}$, which catalyzes the conversion of 3-phosphoglycerate into 2-phosphoglycerate,
- of an enzyme $E_{39}$, which catalyzes the conversion of 2-phosphoglycerate into phosphoenolpyruvate,
- of an enzyme $E_{40}$, which catalyzes the conversion of phosphoenolpyruvate into pyruvate,
- of an enzyme $E_{41}$, which catalyzes the conversion of glycerol into dihydroxyacetone,
- of an enzyme $E_{42}$, which catalyzes the conversion of dihydroxyacetone into dihydroxyacetone phosphate.

In this context, cells which are especially preferred in accordance with the invention are those in which the activity of the following enzymes or enzyme combinations is reduced: $E_{29}$, $E_{30}$, $E_{31}$, $E_{32}$, $E_{33}$, $E_{34}$, $E_{35}$, $E_{36}$, $E_{37}$, $E_{38}$, $E_{39}$, $E_{40}$, $E_{41}$, $E_{42}$, $E_{29}E_{30}$, $E_{29}E_{31}$, $E_{29}E_{32}$, $E_{29}E_{33}$, $E_{29}E_{34}$, $E_{29}E_{35}$, $E_{29}E_{36}$, $E_{29}E_{37}$, $E_{29}E_{38}$, $E_{29}E_{39}$, $E_{29}E_{40}$, $E_{29}E_{41}$, $E_{29}E_{42}$, $E_{30}E_{31}$, $E_{30}E_{32}$, $E_{30}E_{33}$, $E_{30}E_{34}$, $E_{30}E_{35}$, $E_{30}E_{36}$, $E_{30}E_{37}$, $E_{30}E_{38}$, $E_{30}E_{39}$, $E_{30}E_{40}$, $E_{30}E_{41}$, $E_{30}E_{42}$, $E_{31}E_{32}$, $E_{31}E_{33}$, $E_{31}E_{34}$, $E_{31}E_{35}$, $E_{31}E_{36}$, $E_{31}E_{37}$, $E_{31}E_{38}$, $E_{31}E_{39}$, $E_{31}E_{40}$, $E_{31}E_{41}$, $E_{31}E_{42}$, $E_{32}E_{33}$, $E_{32}E_{34}$, $E_{32}E_{35}$, $E_{32}E_{36}$, $E_{32}E_{37}$, $E_{32}E_{38}$, $E_{32}E_{39}$, $E_{32}E_{40}$, $E_{32}E_{41}$, $E_{32}E_{42}$, $E_{33}E_{34}$, $E_{33}E_{35}$, $E_{33}E_{36}$, $E_{33}E_{37}$, $E_{33}E_{38}$, $E_{33}E_{39}$, $E_{33}E_{40}$, $E_{34}E_{41}$, $E_{33}E_{42}$, $E_{34}E_{35}$, $E_{34}E_{36}$, $E_{34}E_{47}$, $E_{34}E_{38}$, $E_{34}E_{39}$, $E_{34}E_{40}$, $E_{34}E_{41}$, $E_{34}E_{42}$, $E_{35}E_{36}$, $E_{35}E_{37}$, $E_{35}E_{38}$, $E_{35}E_{39}$, $E_{35}E_{40}$, $E_{35}E_{41}$, $E_{35}E_{42}$, $E_{36}E_{37}$, $E_{36}E_{38}$, $E_{36}E_{39}$, $E_{36}E_{40}$, $E_{36}E_{41}$, $E_{36}E_{42}$, $E_{37}E_{38}$, $E_{37}E_{39}$, $E_{37}E_{40}$, $E_{37}E_{41}$, $E_{37}E_{42}$, $E_{38}E_{39}$, $E_{39}E_{40}$, $E_{39}E_{41}$, $E_{39}E_{42}$, $E_{40}E_{41}$, $E_{40}E_{42}$, $E_{41}E_{42}$ and $E_{29}E_{30}E_{31}E_{32}E_{33}E_{34}E_{35}E_{36}E_{37}E_{38}E_{39}$-$E_{40}E_{41}E_{42}$.

In this context, it is especially preferred that the enzyme

- $E_{29}$ is an aquaglyceroporin (glycerol facilitator) which is preferably encoded by the glpF gene,
- $E_{30}$ is a glycerol kinase (EC 2.7.1.30) which is preferably encoded by the glpK gene,
- $E_{31}$ is a glycerol 3-phosphate dehydrogenase (EC 1.1.99.5), preferably an FAD-dependent glycerol 3-phosphate dehydrogenase, where the glycerol 3-phosphate dehydrogenase is preferably encoded by the glpA gene, the glpB gene, the glpC gene or the glpD gene, especially preferably by the glpD gene,
- $E_{32}$ is a sulfur transferase which is encoded by the glpE gene,
- $E_{33}$ is a glycerol phosphodiesterase (EC 3.1.4.46) which is preferably encoded by the glpQ gene,
- $E_{34}$ is a glycerol 3-phosphate permease which is preferably encoded by the glpT gene,
- $E_{35}$ is a triose phosphate isomerase (EC 5.3.1.1),
- $E_{36}$ is a glyceraldehyde 3-phosphate dehydrogenase (EC 1.2.1.12),
- $E_{37}$ is a phosphoglycerate kinase (EC 2.7.2.3),
- $E_{38}$ is a phosphoglycerate mutase (EC 5.4.2.1),
- $E_{39}$ is an enolase (EC 4.2.1.11),
- $E_{40}$ is a pyruvate kinase (EC 2.7.1.40),
- $E_{41}$ is a glycerol dehydrogenase (EC 1.1.1.6) which is preferably encoded by the gldA gene, and
- $E_{42}$ is a dihydroxyacetone kinase (EC 2.7.1.29) which is preferably encoded by the dhaK gene.

The gene sequences of the abovementioned enzymes can, again, be found in the gene databases which are known to the skilled worker, in particular the KEGG database, the NCBI database or the EMBL database.

Furthermore, the gap gene, which codes for glyceraldehyde 3-phosphate dehydrogenase (Eikmanns (1992), Journal of Bacteriology 174: 6076-6086), the tpi gene, which codes for triose phosphate isomerase (Eikmanns (1992), Journal of Bacteriology 174: 6076-6086), and the pgk gene, which codes for 3-phosphoglycerate kinase (Eikmanns (1992), Journal of Bacteriology 174: 6076-6086), are also known from other sources.

Using the known genes of the enzymes $E_{29}$ to $E_{42}$, it is possible to prepare genetically modified cells in which at least one, preferably at least two, more preferably at least three and most preferably all activities of the enzymes $E_{29}$ to $E_{42}$ has been increased by means of the techniques (mutation of the enzyme or increase in the expression of the enzyme) described at the outset in connection with the enzyme $E_1$. These cells are capable of being cultured in the presence of glycerol as the only carbon source (or else together with carbohydrates as further carbon source).

In addition to increasing one or more of the enzymatic activities $E_{29}$ to $E_{42}$, it may, in the event that the cell is capable of utilizing glycerol as carbon source, also be advantageous when the following genes are expressed, preferably heterologously expressed, in the cells used in the process according to the invention:

- the glpG gene or the 3925 gene,
- the glpX gene,
- the dhaR gene, the ycgU gene or the b1201 gene,
- the fsa gene, the mipB gene, the ybiZ gene or the B0825 gene,
- the talC gene, the fsaB gene, the yijG gene or the b3946 gene.

Again, the nucleotide sequences of these genes can be found in the KEGG database, the NCBI database or the EMBL database.

In the event that the cells are capable of utilizing carbohydrates as nutrient source, it is preferred that the cell used in the process according to the invention features an activity of at least one, preferably of all, of the following enzymes $E_{43}$ to $E_{45}$ and $E_{36}$ to $E_{40}$ which is increased in comparison with its wild type:

- of an enzyme $E_{43}$, which catalyzes the conversion of α-D-glucose 6-phosphate into β-D-fructose 6-phosphate,
- of an enzyme $E_{44}$, which catalyzes the conversion of β-D-fructose 6-phosphate into β-D-fructose 1,6-biphosphate,
- of an enzyme $E_{45}$, which catalyzes the conversion of β-D-fructose 1,6-biphosphate to glyceraldehyde 3-phosphate and dihydroxyacetone phosphate,
- of an enzyme $E_{36}$, which catalyzes the conversion of glyceraldehyde 3-phosphate into 1,3-biphosphoglycerate,
- of an enzyme $E_{37}$, which catalyzes the conversion of 1,3-biphosphoglycerate into 3-phosphoglycerate, of an enzyme $E_{38}$, which catalyzes the conversion of 3-phosphoglycerate into 2-phosphoglycerate, of an enzyme $E_{39}$, which catalyzes the conversion of 2-phosphoglycerate into phosphoenolpyruvate, and of an enzyme $E_{40}$, which catalyzes the conversion of phosphoenolpyruvate into pyruvate.

In this context genetically modified cells which are especially preferred in accordance with the invention are those in which the activity of the following enzymes or enzyme combinations is increased:

$E_{36}$, $E_{37}$, $E_{38}$, $E_{39}$, $E_{40}$, $E_{43}$, $E_{44}$, $E_{45}$, $E_{36}E_{37}$, $E_{36}E_{38}$, $E_{36}E_{39}$, $E_{36}E_{40}$, $E_{36}E_{43}$, $E_{36}E_{44}$, $E_{36}E_{45}$, $E_{37}E_{38}$, $E_{37}E_{39}$, $E_{37}E_{40}$, $E_{37}E_{43}$, $E_{37}E_{44}$, $E_{37}E_{45}$, $E_{38}E_{39}$, $E_{38}E_{40}$, $E_{38}E_{43}$, $E_{38}E_{44}$, $E_{38}E_{45}$, $E_{39}E_{40}$, $E_{39}E_{43}$, $E_{39}E_{44}$, $E_{39}E_{45}$, $E_{40}E_{43}$, $E_{40}E_{44}$, $E_{40}E_{45}$, $E_{43}E_{44}$, $E_{43}E_{45}$, $E_{44}E_{45}$, and $E_{36}E_{37}E_{38}E_{39}$-$E_{40}E_{43}E_{44}E_{45}$.

In this context, it is especially preferred that the enzyme $E_{43}$ is a glucose 6-phosphate isomerase (EC 5.3.1.9), $E_{44}$ is a 6-phosphofructo kinase (EC 2.7.1.11), $E_{45}$ is a fructose bisphosphate aldolase (EC 4.1.2.13), $E_{36}$ is a glyceraldehyde 3-phosphate dehydrogenase (EC 1.2.1.12), $E_{37}$ is a phosphoglycerate kinase (EC 2.7.2.3), $E_{38}$ is a phosphoglycerate mutase (EC 5.4.2.1), $E_{39}$ is an enolase (EC 4.2.1.11) and $E_{40}$ is a pyruvate kinase (EC 2.7.1.40).

Again, the nucleotide sequences of these genes can be found be found in the KEGG database, the NCBI database or the EMBL database.

In the event that the cell is capable of utilizing carbohydrates as carbon source, it is furthermore preferred to increase not only the activity of the abovementioned enzymes $E_{43}$ to $E_{45}$ and $E_{36}$ to $E_{40}$, but also the uptake of glucose into the cells, for example by increasing the activity of enzymes of the phosphotransferase system, in particular those enzymes which are encoded by ptsI, ptsH and ptsM genes, or by enhancing glucokinase (EC 2.7.1.2), which is preferably encoded by the glk gene. In this context, reference is made in particular to U.S. Pat. No. 6,680,187, U.S. Pat. No. 6,818,432, U.S. Pat. No. 6,913,910 and U.S. Pat. No. 6,884,614, whose disclosure content with regard to the possibilities for overexpressing the ptsI, ptsH, ptsM and glk genes is hereby incorporated by reference and forms part of the disclosure of the present invention. In the event that carbohydrates act as carbon source, it may also be advantageous to promote the pentose phosphate pathway in a targeted manner, for example by increasing the activity of glucose 6-phosphate dehydrogenase (EC 1.1.1.49) and of 6-phosphogluconate dehydrogenase (EC 1.1.1.44), which is preferably encoded by the gnd gene, while, if appropriate, simultaneously inhibiting glycolysis, for example by weakening the activity of glucose 6-phosphate isomerase, as is described in WO-A-01/07626.

In the event that, according to the special embodiment of the process according to the invention where a genetically modified cell is used, in which methylmalonate semialdehyde is formed as precursor and succinyl-coenzyme A as intermediate, the cells form 3-hydroxyisobutyric acid or polyhydroxyalkanoates based on 3-hydroxyisobutyric acid via oxaloacetate and pyruvate as intermediates, it may furthermore be preferred to reduce the activity of at least one, preferably of all, of the following enzymatic activities in the cell:

of an enzyme which catalyzes the conversion of oxaloacetate into phosphoenolpyruvate, such as, for example, phosphoenylpyruvate carboxykinase (EC 4.1.1.49) (see also DE-A-199 50 409), of an enzyme which catalyzes the conversion of pyruvate into acetate such as, for example, pyruvate oxidase (EC 1.2.2.2) (see also DE-A-199 51 975), of an enzyme which catalyzes the conversion of α-D-glucose 6-phosphate into β-D-fructose 6-phosphate (see also U.S. Ser. No. 09/396,478), of an enzyme which catalyzes the conversion of pyruvate into lactate such as, for example, l-lactate dehydrogenase (EC 1.1.1.27) or lactate-malate transhydrogenase (EC 1.1.99.7), of an enzyme which catalyzes the conversion of pyruvate into acetyl-coenzyme A such as, for example, pyruvate dehydrogenase (EC 1.2.1.51), of an enzyme which catalyzes the conversion of pyruvate into acetyl phosphate such as, for example, pyruvate oxidase (EC 1.2.3.3), of an enzyme which catalyzes the conversion of pyruvate into acetate, such as, for example, pyruvate dehydrogenase (EC 1.2.2.2), of an enzyme which catalyzes the conversion of pyruvate into phosphoenolpyruvate such as, for example, phosphoenolpyruvate synthase (EC 2.7.9.2) or pyruvate, phosphate dikinase (EC 2.7.9.1), of an enzyme which catalyzes the conversion of pyruvate into alanine such as, for example, alanine transaminase (2.6.1.2) or alanine-oxo-acid transaminase (EC 2.6.1.12), and/or of an enzyme which converts pyruvate into acetolactate such as, for example, acetohydroxy acid synthase (EC 2.2.1.6).

Cells which are especially preferred in accordance with the invention and which are capable of forming 3-hydroxyisobutyric acid or polyhydroxyalkanoates based on 3-hydroxybutyric acid from carbohydrates as carbon source via succinyl-coenzyme A as intermediate and in which one or more of the abovementioned enzymatic activities, in particular one of the enzymatic activities $E_1$ to $E_{45}$, more preferably the enzymatic activities $E_1$, $E_1E_2E_3E_4$, $E_1E_4E_5E_6E_7$ or and $E_1E_4E_5E_7$, can be increased are those microorganisms which have been described by Bennett et al., *Metab. Eng.* (2005), 7 (3), pages 229 to 239, Bennett et al., *Biotechnol. Bioeng.* (2005), 90 (6), pages 775 to 779, Bennett et al., *Biotechnol. Prog.* (2005), 21 (2), pages 358 to 365, Bennett et al. (2005), *Appl. Microbiol. Biotechnol.,* 67 (4), pages 515 to 523, Vemuri et al. (2002), *Applied and Environmental Microbiology* 68 (4), pages 1715 to 1727 and in U.S. Pat. No. 6,455,284.

If, according to the first special embodiment of the process according to the invention, the formation of 3-hydroxyisobutyric acid or of the polyhydroxyalkanoates based on 3-hydroxyisobutyric acid starting from L-glutamate as carbon source takes place via succinyl-coenzyme A as intermediate, it is, in accordance with a further special embodiment of the process according to the invention, where a genetically modified cell is used, in which methylmalonate semialdehyde is formed as precursor and succinyl-coenzyme A as intermediate, furthermore preferred in accordance with the invention that the cell used features an activity of at least one of the, preferably of the two, following enzymes $E_{28}$ and $E_{46}$ which is increased in comparison with its wild type (see FIG. 10):

of an enzyme $E_{46}$, which catalyzes the conversion of L-glutamate into 2-oxoglutarate;

of an enzyme $E_{28}$, which catalyzes the conversion of 2-oxoglutarate into succinyl-coenzyme A.

In this context, it is especially preferred that the enzyme $E_{46}$ is a glutamate synthase (EC 1.4.1.13 or EC 1.4.1.14), a glutamate dehydrogenase (EC 1.4.1.2, EC 1.4.1.3 or EC 1.4.1.4) or an aspartate transaminase (EC 2.6.1.1 or EC 2.6.1.2) and $E_{28}$ is a 2-oxoglutarate synthase (EC 1.2.7.3).

Preferred as enzyme $E_{28}$ are those which have already been mentioned at the outset as preferred enzymes $E_{28}$.

The enzyme $E_{46}$ is preferably encoded by the genes selected from the group consisting of: myn8, glt1, adr290wp, gltB, gltD, yeiT, aegA, ygfT, gltD-1, gltD-2, glt1, glt2, gls1, gltA, glt, glxD, gltA, yerD, cgl0184, cgl0185, sc3c9.12, gdh1, gdh2, agl40 cp, gdhA, gdhA1, gdhA2, gluD, rocG, ypcA, gudB, gluD, gdhA, gdhA2, gdh, gdhA-1, gdhA2-2, gdhA-3, gluD1, gluD2, glud1-prov, glud1a, t11I18.2, t2I1.150, mrg7.13, got1, got2, caspat, got2-prov, xr406-prov, 406-prov, cg4233, cg4233, cg8430, cg8430, f23n19.17, f13j11.16, t26c19.9, f7f1.18, f10n7.200, t16l1.170, f15n18.110, t20d1.70, aat, aat1, aat2, abl038wp, afr211 cp, agx1, bnA4, aatA, aatB, ybdL, aspC, yfbQ, ydcR, avtA2, aspC-1, aspC-2, aspC-3, aspC-4, aspB, aspB-1, aspB-2, aspB-3, aspB-4, argD1, argD2, aatAc, ywfG, mtnV, alaT, avtA1, avtA2, avtA3, cgl0240, cgl1103, cgl2599, cgl2844, dapC, 2sck36.07c, sc9e12.21, sc2h4.04c, aspB1, aspB2, aspB3, tyrB, gpt, gpt1, gpt2, mgc82097, cgl1640, c32f10.8, f20d23.34, f26f24.16, f24j13.15, t10d10.20 and agrwp.

Again, the nucleotide sequences of these genes can be found be found in the KEGG database, the NCBI database or the EMBL database.

In accordance with a second special embodiment of the process according to the invention, where a genetically modified cell is used, in which the formation of 3-hydroxyisobutyric acid or of polyhydroxyalkanoates based on 3-hydroxyisobutyric acid takes place via methylmalonate semialdehyde as precursor, it is preferred that the formation of 3-hydroxyisobutyric acid or of the polyhydroxyalkanoate based on 3-hydroxyisobutyric acid takes place via propionyl-coenzyme A as intermediate, where the cell used is capable of preferentially utilizing carbohydrates, glycerol, methane or methanol as carbon source. In this context, a variety of pathways exist for arriving at 3-hydroxyisobutyric acid or polyhydroxyalkanoates based on 3-hydroxyisobutyric acid, departing from propionyl-coenzyme A.

In accordance with a first alternative of this second special embodiment of the process according to the invention, the formation of intermediate propionyl-coenzyme A takes place via acetyl-coenzyme A as further intermediate. In this context, it is especially preferred that the genetically modified cell used features an activity of at least one of the following enzymes $E_4$, $E_5$ and $E_{47}$ to $E_{52}$ which is increased in comparison with its wild type (see FIGS. 11 and 12):

of an enzyme $E_{47}$, which catalyzes the conversion of acetyl-coenzyme A into malonyl-coenzyme A;

of an enzyme $E_{48}$, which catalyzes the conversion of malonyl-coenzyme A into malonate semialdehyde;

of an enzyme $E_{49}$, which catalyzes the conversion of malonate semialdehyde into 3-hydroxypropionate;

of an enzyme $E_{50}$, which catalyzes the conversion of 3-hydroxypropionate into 3-hydroxypropionyl-coenzyme A;

of an enzyme $E_{51}$, which catalyzes the conversion of 3-hydroxypropionyl-coenzyme A into acryloyl-coenzyme A;

of an enzyme $E_{52}$, which catalyzes the conversion of acryloyl-coenzyme A into propionyl-coenzyme A;

of an enzyme $E_5$, which catalyzes the conversion of propionyl-coenzyme A into methylmalonate semialdehyde;

of an enzyme $E_4$, which catalyzes the conversion of methylmalonate semialdehyde into 3-hydroxy-isobutyrate.

Genetically modified cells are especially preferably used in accordance with the invention, in which the activity of the following enzymes or enzyme combinations is increased: $E_{47}$, $E_{48}$, $E_{49}$, $E_{50}$, $E_{51}$, $E_{52}$, $E_4$, $E_5$ and $E_{47}E_{48}E_{49}E_{50}E_{51}E_{52}E_4E_5$.

Furthermore, it is particularly preferred in this context that the enzyme $E_4$ is a 3-hydroxyisobutyrate dehydrogenase (EC 1.1.1.31) or a 3-hydroxyacyl-coenzyme A dehydrogenase (EC 1.1.1.35), $E_5$ is a methylmalonate-semialdehyde dehydrogenase (EC 1.2.1.27), $E_{47}$ is a malonyl-coenzyme A decarboxylase (EC 4.1.1.9), a malonate-coenzyme A transferase (EC 2.8.3.3), a methylmalonyl-coenzyme A carboxytransferase (EC 2.1.3.1) or an acetyl-coenzyme A carboxylase (EC 6.4.1.2), $E_{48}$ is a malonate-semialdehyde dehydrogenase (EC 1.2.1.18), $E_{49}$ is a 3-hydroxypropionate dehydrogenase (EC 1.1.1.59), $E_{50}$ is a 3-hydroxyisobutyryl-coenzyme A hydrolase (EC 3.1.2.4), $E_{51}$ is an enoyl-coenzyme A hydratase (EC 4.2.1.17) and $E_{52}$ is an acyl-coenzyme A dehydrogenase (EC 1.3.99.3).

Preferred genes for the enzymes $E_4$ and $E_5$ are those which have already been described above in connection with the first special embodiment of the cell according to the invention.

The enzyme $E_{47}$ is preferably encoded by genes selected from the group consisting of mlycd, t19b17.4, tb08.29O4.110, matA, acac, acaca, acacb, f5j5.21, f15c21.2, t8p21.5, acc1, aar071wp, accA, accB, accC, accD, accC1, accC2, mmdA, fabG, accD1, accD2, accD3, cgl0831, accBC, dtsR1, accDA, scc24.16c and cgl1327, where accA, accC and accD are most preferred.

The enzyme $E_{48}$ is preferably encoded by the iolD gene.

The enzyme $E_{51}$ is preferably encoded by genes selected from the group consisting of echS1, ehhadh, hadha, echs1-prov, cg4389, cg4389, cg6543, cg6984, cg8778, ech-1, ech-2, ech-3, ech-4, ech-5, ech-6, ech-7, FCAALL.314, fcaall.21, fox2, eci1, eci2, paaF, paaG, yfcX, fadB, faoA, rpfF, phaA, phaB, echA1, echA2, echA3, echA4, echA5, echA6, echA7, echA8, echA9, echA9, echA10, echA11, echA12, echA13, echA14, echA15, echA16, echA17, echA18, echA19, echA20, echA21, fad-1, fad-2, fad-3, dcaE, hcaA, fadJ, rsp0671, rsp0035, rsp0648, rsp0647, rs03234, rs03271, rs04421, rs04419, rs02820, rs02946, paaG1, paaG2, paaG3, ech, pksH, ydbS, eccH1, ecCH2, pimF, fabJ1, fabJ2, caiD2, ysiB, yngF, yusL, fucA, cgl0919, scf41.23, scd10.16, sck13.22, scp8.07c, stbac16h6.14, sc5f2a.15, sc6a5.38, hbd-1, hbd-2, hdb-3, hdb-4, hdb-5, hdb-6, hdb-7, hdb-8, hdb-9, hdb-10, fad-1, fad-2, fad-3, fad-4, fad-5, paaF-1, paaF-2, paaF-3, paaF-4, paaF-5, paaF-6, paaF-7 and crt.

The enzyme $E_{52}$ is preferably encoded by genes selected from the group consisting of acadl, acadm, acad10, acad11, acadm-prov, acadl-prov, mgc81873, cgl2262, cg4703, cg4860, f3e22.5, afl213wp, acdC, fadE13, acd-1, acd-2, acd-3, acd-4, acd-5, acd-6, acd-7, acd-8, acd-9, acd-10, acd-11, acd-12, acd, fadE1, fadE2, fadE3, fadE4, fadE5, fadE6, fadE7, fadE13, fadE14, fadE15, fadE16, fadE17, fadE18, fadE19, fadE20, fadE21, fadE22, fadE23, fadE26, fadE27, fadE30, fadE31, fadE33, fadE35, fadE38, fadE45, fadE, caiA, aidB, RSp0036, RS03588, mmgC, acdA-3, bcd, acdA, acdH1, acdH2, acdH3, aidB, acdI and acdH.

The nucleotide sequences of suitable genes for the enzymes $E_{47}$ to $E_{52}$, in particular also of the enzymes $E_{49}$ and $E_{50}$, can be found in the KEGG database, the NCBI database or the EMBL database.

According to a second alternative of this second special embodiment of the process according to the invention, the formation of the intermediate propionyl-coenzyme A also takes place via acetyl-coenzyme A as further intermediate, where, according to this alternative, the propionyl-coenzyme A is not converted directly into the methylmalonate semialdehyde, but via methylmalonyl-coenzyme A. In this context, it is especially preferred that the genetically modified cell used features an activity of at least one of the following enzymes $E_2$ to $E_4$, $E_6$, $E_7$ and $E_{47}$ to $E_{52}$ which is increased in comparison with its wild type (see FIGS. 13 and 14):

of an enzyme $E_{47}$, which catalyzes the conversion of acetyl-coenzyme A into malonyl-coenzyme A;

of an enzyme $E_{48}$, which catalyzes the conversion of malonyl-coenzyme A into malonate semialdehyde;

of an enzyme $E_{49}$, which catalyzes the conversion of malonate semialdehyde into 3-hydroxypropionate;

of an enzyme $E_{50}$, which catalyzes the conversion of 3-hydroxypropionate into 3-hydroxypropionyl-coenzyme A;

of an enzyme $E_{51}$, which catalyzes the conversion of 3-hydroxypropionyl-coenzyme A into acryloyl-coenzyme A;

of an enzyme $E_{52}$, which catalyzes the conversion of acryloyl-coenzyme A into propionyl-coenzyme A;

of an enzyme $E_7$, which catalyzes the conversion of propionyl-coenzyme A into (S)-methylmalonyl-coenzyme A;

of an enzyme $E_6$, which catalyzes the conversion of (S)-methylmalonyl-coenzyme A into (R)-methylmalonyl-coenzyme A;

of an enzyme $E_2$, which catalyzes the conversion of (R)-methylmalonyl-coenzyme A into methyl malonate;

of an enzyme $E_3$, which catalyzes the conversion of methyl malonate into methylmalonate semialdehyde;

of an enzyme $E_4$, which catalyzes the conversion of methylmelonate-semialdehyde into 3-hydroxy-isobutyrate.

Genetically modified cells are especially preferably used according to the invention, in which the activity of the following enzymes or enzyme combinations is increased: $E_2$, $E_3$, $E_4$, $E_6$, $E_7$, $E_{47}$, $E_{48}$, $E_{49}$, $E_{50}$, $E_{51}$, $E_{52}$ and $E_2E_3E_4E_6E_7E_{47}E_{48}E_{49}E_{50}E_{51}E_{52}$.

Preferred enzymes and genes of these enzymes are those genes and enzymes which have already been mentioned above in connection with the enzymes $E_2$ to $E_4$, $E_6$, $E_7$ and $E_{47}$ to $E_{52}$.

According to a third alternative of this first alternative of the second special embodiment of the process according to the invention, the formation of the intermediate propionyl-coenzyme A also takes place via acetyl-coenzyme A as further intermediate, where, according to this alternative, the propionyl-coenzyme A is, again, not converted directly into methylmalonate-semialdehyde, but via (R)-methylmalonyl-coenzyme A (and not via (S)-methylmalonyl-coenzyme A). In this context, it is especially preferred that the genetically modified cell used features an activity of at least one of the following enzymes $E_2$ to $E_4$, $E_7$ and $E_{47}$ to $E_{52}$ which is increased in comparison with its wild type (see FIGS. 15 and 16):

of an enzyme $E_{47}$, which catalyzes the conversion of acetyl-coenzyme A into malonyl-coenzyme A;

of an enzyme $E_{48}$, which catalyzes the conversion of malonyl-coenzyme A into malonate semialdehyde;

of an enzyme $E_{49}$, which catalyzes the conversion of malonate semialdehyde into 3-hydroxypropionate;

of an enzyme $E_{50}$, which catalyzes the conversion of 3-hydroxypropionate into 3-hydroxypropionyl-coenzyme A;

of an enzyme $E_{51}$, which catalyzes the conversion of 3-hydroxypropionyl-coenzyme A into acryloyl-coenzyme A;

of an enzyme $E_{52}$, which catalyzes the conversion of acryloyl-coenzyme A into propionyl-coenzyme A;

of an enzyme $E_7$, which catalyzes the conversion of propionyl-coenzyme A into methylmalonyl-coenzyme A;

of an enzyme $E_2$, which catalyzes the conversion of methylmalonyl-coenzyme A into methylmalonate;

of an enzyme $E_3$, which catalyzes the conversion of methyl malonate into methylmalonate-semialdehyde;

of an enzyme $E_4$, which catalyzes the conversion of methylmalonate-semialdehyde into 3-hydroxy-isobutyrate.

Genetically modified cells are especially preferably used according to the invention, in which the activity of the following enzymes or enzyme combinations is increased: $E_2$, $E_3$, $E_4$, $E_7$, $E_{47}$, $E_{48}$, $E_{49}$, $E_{50}$, $E_{51}$, $E_{52}$ and $E_2E_3E_4E_7E_{47}E_{48}E_{49}E_{50}E_{51}E_{52}$.

Preferred enzymes and genes of these enzymes are, again, those genes and enzymes which have already been mentioned above in connection with the enzymes $E_2$ to $E_4$, $E_7$ and $E_{47}$ to $E_{52}$.

According to a fourth alternative of the second special embodiment of the process according to the invention, the formation of the intermediate propionyl-coenzyme A also takes place via acetyl-coenzyme A as further intermediate, where, according to this alternative, acetoacetyl-coenzyme A is formed as intermediate. In this context, it may be preferred that the genetically modified cell used features an activity of at least one of the following enzymes $E_8$ and $E_{53}$ to $E_{61}$ which is increased in comparison with its wild type:

of an enzyme $E_{53}$, which catalyzes the conversion of two acetyl-coenzyme A units into acetoacetyl-coenzyme A;

of an enzyme $E_{54}$, which catalyzes the conversion of acetoacetyl-coenzyme A into 3-hydroxybutanoyl-coenzyme A;

of an enzyme $E_{55}$, which catalyzes the conversion of 3-hydroxybutanoyl-coenzyme A into crotonyl-coenzyme A;

of an enzyme $E_{56}$, which catalyzes the conversion of crotonyl-coenzyme A into butyryl-coenzyme A;

of an enzyme $E_{57}$, which catalyzes the conversion of butyryl-coenzyme A into ethylmalonyl-coenzyme A;

of an enzyme $E_{58}$, which catalyzes the conversion of ethylmalonyl-coenzyme A into methylsuccinyl-coenzyme A;

of an enzyme $E_{59}$, which catalyzes the conversion of methylsuccinyl-coenzyme A isobutyryl-coenzyme A;

of an enzyme $E_{60}$, which catalyzes the conversion of isobutyryl-coenzyme A into methacrylyl-coenzyme A;

of an enzyme $E_{61}$, which catalyzes the conversion of methacrylyl-coenzyme A into 3-hydroxyisobutyryl-coenzyme A;

of an enzyme $E_8$, which catalyzes the conversion of 3-hydroxyisobutyryl-coenzyme A into 3-hydroxy-isobutyrate.

In this context, genetically modified cells which are especially preferred according to the invention are those in which the activity of the following enzymes or enzyme combinations is increased: $E_8$, $E_{53}$, $E_{54}$, $E_{55}$, $E_{56}$, $E_{57}$, $E_{58}$, $E_{59}$, $E_{60}$, $E_{61}$ and $E_8E_{53}E_{54}E_{55}E_{56}E_{57}E_{58}E_{59}E_{60}E_{61}$.

This metabolic pathway and the enzymes which play a role in this metabolic pathway are described, for example, in Korotkova et al., *Journal of Bacteriology* (2002), pages 1750 to 1758.

According to a fifth alternative of the second special embodiment of the process according to the invention, the formation of the intermediate propionyl-coenzyme A takes place via, again, acetyl-coenzyme A as further intermediate, where, according to this alternative, acetoacetyl-coenzyme A is formed as further intermediate but where, in this case, ethylmalonyl-coenzyme A is formed directly from crotonyl-coenzyme A. In this context, it may be preferred that the cell features an activity of at least one of the following enzymes $E_8$, $E_{53}$ to $E_{55}$, $E_{58}$ and $E_{62}$ to $E_{65}$ which is increased in comparison with its wild type (see FIG. 17):

of an enzyme $E_{53}$, which catalyzes the conversion of two acetyl-coenzyme A units into acetoacetyl-coenzyme A;

of an enzyme $E_{54}$, which catalyzes the conversion of acetoacetyl-coenzyme A into 3-hydroxybutyryl-coenzyme A;

of an enzyme $E_{55}$, which catalyzes the conversion of 3-hydroxybutyryl-coenzyme A into crotonyl-coenzyme A;

of an enzyme $E_{62}$, which catalyzes the conversion of crotonyl-coenzyme A into ethylmalonyl-coenzyme A of an enzyme $E_{58}$, which catalyzes the conversion of ethylmalonyl-coenzyme A into methylsuccinyl-coenzyme A;

of an enzyme $E_{63}$, which catalyzes the conversion of methylsuccinyl-coenzyme A into mesaconyl-coenzyme A;

of an enzyme $E_{64}$, which catalyzes the conversion of mesaconyl-coenzyme A into β-methylmalyl-coenzyme A;

of an enzyme $E_{65}$, which catalyzes the conversion of β-methylmalyl-coenzyme A into glyoxylate and propionyl-coenzyme A.

Then, from propionyl-coenzyme A 3-hydroxyisobutyric acid can be formed in the above-described manner (increasing the activity of one or more of the enzymes $E_7$, $E_2$, $E_3$ and $E_4$, increasing the activity of one or more of the enzymes $E_7$, $E_6$, $E_2$, $E_3$ and $E_4$, or increasing the activity of one of the, or of both, enzymes $E_4$ and $E_5$).

In this context, it is especially preferred that the enzyme $E_{53}$ is a β-ketothiolase (EC 2.3.1.9), $E_{54}$ is an acetoacetyl-coenzyme A reductase (an EC 1.1.1.36), $E_{55}$ is an enoyl-coenzyme A hydratase (EC 4.2.1.17), $E_{62}$ is a crotonyl-coenzyme A decarboxylase, $E_{58}$ is an ethylmalonyl-coenzyme A mutase (EC 5.4.99.2), $E_{63}$ is a methylsuccinyl-coenzyme A dehydrogenase, $E_{64}$ is a mesaconyl-coenzyme A hydratase, and $E_{65}$ is a β-methylmalyl/L-malyl-coenzyme A lyase.

The enzyme $E_{53}$ is preferably encoded by genes selected from the group consisting of acat1, acat2, loc484063, loc489421, mgc69098, mgc81403, mgc81256, mgc83664, kat-1, erg10, ygeF, atoB, fadAx, phbA-1, phbA-2, atoB-2, pcaF, pcaF-2, phb-A, bktB, phaA, tioL, thlA, fadA, paaJ, phbAf, pimB, mmgA, yhfS, thl, vraB, thl, mvaC, thiL, paaJ, fadA3, fadA4, fadA5, fadA6, cgl12392, catF, sc8f4.03, thiL1, thiL2, acaB1, acaB2, acaB3 or acaB4, where acat1, acat2, atoB and phbA and the corresponding gene from *Rhodobacter sphaeroides* are especially preferred.

The enzyme $E_{54}$ is preferably encoded by genes selected from the group consisting of phbB, fabG, phbN1, phbB2 or cgl12444, where phbB is especially preferred and the corresponding gene from *Rhodobacter sphaeroides* is especially preferred.

The enzyme $E_{55}$ is preferably encoded by genes selected from the group consisting of echS1, ehhadh, hadha, echA1-prov, cg4389, cg4389, cg6543, cg6984, cg8778, ech-1, ech-2, ech-3, ech-4, ech-5, ech-6, ech-7, FCAALL.314, fcaall.21, fox2, eci1, eci2, paaF, paaG, yfcX, fadB, faoA, rpfF, phaA, phaB, echA1, echA2, echA3, echA4, echA5, echA6, echA7, echA8, echA9, echA9, echA10, echA11, echA12, echA13, echA14, echA15, echA16, echA17, echA18, echA19, echA20, echA21, fad-1, fad-2, fad-3, dcaE, hcaA, fadJ, rsp0671, rsp0035, rsp0648, rsp0647, rs03234, rs03271, rs04421, rs04419, rs02820, rs02946, paaG1, paaG2, paaG3, ech, pksH, ydbS, eccH1, ecCH2, pimF, fabJ1, fabJ2, caiD2, ysiB, yngF, yusL, fucA, cg10919, scf41.23, scd10.16, sck13.22, scp8.07c, stbac16h6.14, sc5f2a.15, sc6a5.38, hbd-1, hbd-2, hdb-3, hdb-4, hdb-5, hdb-6, hdb-7, hdb-8, hdb-9, hdb-10, fad-1, fad-2, fad-3, fad-4, fad-5, paaF-1, paaF-2, paaF-3, paaF-4, paaF-5, paaF-6, paaF-7 and crt where the corresponding gene from *Rhodobacter* sphaeroides is especially preferred.

Suitable genes for the enzyme $E_{58}$ are selected from the group consisting of mut, mutA, mutB, sbm, sbmA, sbmB, sbm5, bhbA, mcmA, mcmA1, mcmA2, mcmB, mcm1, mcm2, mcm3, icmA, meaA1 and meaA2, where, again, the corresponding gene from *Rhodobacter sphaeroides* is especially preferred.

The enzyme which is preferably employed as enzyme $E_{62}$ is an enzyme from *Rhodobacter sphaeroides* which is encoded by the DNA sequence with the SEQ ID No 05 and which has the amino acid sequence as shown in SEQ ID No 06.

Preferred genes for the enzymes $E_{63}$, $E_{64}$ and $E_{65}$ are, in particular, the genes for these enzymes from *Rhodobacter sphaeroides.*

Further examples of nucleotide sequences of the abovementioned genes can also be found in the KEGG database, the NCBI database or the EMBL database, inter alia.

As has already been explained above, the first alternative of the second preferred embodiment of the process according to the invention generates 3-hydroxyisobutyric acid or the polyhydroxyalkanoates based on 3-hydroxyisobutyric acid via propionyl-coenzyme A and acetyl-coenzyme A as intermediates. In this context, it may be meaningful, in principle, to influence not only one or more of the abovementioned enzymatic activities $E_2$ to $E_8$ and $E_{47}$ to $E_{65}$, but also those enzymatic activities which bring about an increase in the formation of acetyl-coenzyme A in the cell.

In the event that 3-hydroxyisobutyric acid is formed from carbohydrates or glycerol as carbon source, it may be preferred that the cell features an increased activity in an enzyme $E_{66}$, which catalyzes the conversion of pyruvate into acetyl-coenzyme A. This enzyme $E_{66}$ preferably takes the form of a pyruvate dehydrogenase (EC 1.2.1.51).

In the event that 3-hydroxyisobutyric acid is formed from $C_1$-carbon sources such as, for example, methane or methanol, it may be preferred that the cell features an activity of at least one of the enzymes $E_{67}$ to $E_{71}$ which is increased in comparison with its wild type:

of an enzyme $E_{67}$, which catalyzes the conversion of methane into methanol;

of an enzyme $E_{68}$, which catalyzes the conversion of methanol into formaldehyde;

of an enzyme $E_{69}$, which catalyzes the conversion of formaldehyde into 5,10-methylenetetrahydrofolate;

of an enzyme $E_{70}$, which catalyzes the conversion of 5,10-methylenetetrahydrofolate into 5-methyltetrahydrofolate;

of an enzyme $E_{71}$, which catalyzes the conversion of 5-methyltetrahydrofolate into acetyl-coenzyme A.

In this context, it is especially preferred that the enzyme $E_{67}$ is a methane monooxygenase (EC 1.14.13.25), $E_{68}$ is a methanol dehydrogenase (EC 1.1.1.244), $E_{69}$ is a methylmalonate-semialdehyde dehydrogenase (EC 1.2.1.27), $E_{70}$ is a methylenetetrahydrofolate reductase (EC 1.5.1.20), $E_{71}$ is a carbon monoxide dehydrogenase (EC 1.2.99.2).

The nucleotide sequences of suitable genes for the enzymes $E_{63}$ to $E_{67}$ can be found in the KEGG database, the NCBI database or the EMBL database.

According to a third special embodiment of the process according to the invention, where a genetically modified cell is used, in which the formation of 3-hydroxyisobutyric acid or of polyhydroxyalkanoates based on 3-hydroxyisobutyric acid takes place via methylmalonate-semialdehyde as precursor, it is preferred that the formation of 3-hydroxyisobutyric acid or of the polyhydroxyalkanoate based on 3-hydroxyisobutyric acid takes place via acryloyl-coenzyme A as intermediate, where the cell used is capable of preferentially utilizing carbohydrates, glycerol or glutamate as carbon source.

In connection with the third special embodiment of the process according to the invention, it is especially preferred when the genetically modified cell used features an activity of at least one of the following enzymes $E_2$ to $E_4$, $E_{62}$, $E_{72}$ and $E_{73}$ which is increased in comparison with its wild type (see FIG. 18):

of an enzyme $E_{72}$, which catalyzes the conversion of beta-alanine to beta-alanyl-coenzyme A, of an enzyme $E_{73}$, which catalyzes the conversion of beta-alanyl-coenzyme A into acrylyl-coenzyme A, of an enzyme $E_{62}$, which catalyzes the conversion of acrylyl-coenzyme A into methylmalonyl-coenzyme A (or the conversion of crotonyl-coenzyme A into ethylmalonyl-coenzyme A), of an enzyme $E_2$, which catalyzes the conversion of methylmalonyl-coenzyme A into methyl malonate;

of an enzyme $E_3$, which catalyzes the conversion of methyl malonate into methylmalonate-semialdehyde;

of an enzyme $E_4$, which catalyzes the conversion of methylmalonate-semialdehyde into 3-hydroxyisobutyric acid.

In this context, cells which are especially preferred according to the invention are those in which the activity of the following enzymes or enzyme combinations is increased: $E_{62}E_2$, $E_{62}E_3$, $E_{62}E_4$, $E_{62}E_2E_3$ and $E_{72}E_{73}E_{62}E_2E_3E_4$. In connection with the fourth special embodiment, too, of the process according to the invention it may be advantageous to use a genetically modified cell in which an enzyme which is capable of catalyzing at least two of the above-described reaction steps is overexpressed. Here too, it is possible for example to employ an enzyme which features both the activity of the enzyme $E_2$ and the activity of the enzyme $E_3$, such as, for example, the malonyl-coenzyme A reductase from *Sulfolobus tokodaii*, which is encoded by the DNA sequence with the SEQ ID No 03 and which features the amino acid sequence as shown in SEQ ID No 04. Furthermore, it is, in principle, also possible in the context of the fourth special embodiment of the cell according to the invention to employ a cell which is already capable of forming especially large amounts of acrylyl-coenzyme A.

In this context, it is especially preferred that the enzyme $E_{72}$ is a coenzyme A transferase (EC 2.8.3.1) or a coenzyme A synthetase, preferably a coenzyme A transferase, $E_{73}$ is a beta-alanyl-coenzyme A ammonia-lyase (EC 4.3.1.6), $E_{62}$ is a crotonyl-coenzyme A decarboxylase $E_2$ is a methylmalonyl-coenzyme A hydrolase (EC 3.1.2.17), $E_3$ is an aldehyde dehydrogenase (EC 1.2.1.3) or an aldehyde oxidase (EC 1.2.3.1) and $E_4$ is a 3-hydroxyisobutyrate dehydrogenase (EC 1.1.1.31) or a 3-hydroxyacyl-coenzyme A dehydrogenase (EC 1.1.1.35).

Preferred enzymes $E_{72}$ with a CoA transferase activity are those from *Megasphaera elsdenii, Clostridium propionicum, Clostridium kluyveri* and also from *Escherichia coli*. Examples which may be mentioned at this point of a DNA sequence coding for a CoA transferase is the sequence from *Megasphaera elsdenii* referred to as SEQ ID No: 24 in WO-A-03/062173. Enzymes which are furthermore preferred are those variants of the CoA transferase which are described in WO-A-03/062173.

Suitable enzymes $E_{73}$ with a beta-alanyl-coenzyme A ammonia-lyase activity are, for example, those from *Clostridium propionicum*. DNA sequences which code for such an enzyme can be obtained for example from *Clostridium propionicum* as described in Example 10 in WO-A-03/062173. The DNA sequence which codes for the beta-alanyl-coenzyme A ammonia-lyase from *Clostridium propionicum* is specified in WO-A-03/062173 as SEQ ID No: 22.

An enzyme $E_{62}$ which is preferably employed is, again, the crotonyl-coenzyme A decarboxylase from *Rhodobacter sphaeroides*, which is encoded by the DNA sequence with the SEQ ID No 05 and which features the amino acid sequence as shown in SEQ ID No 06. This enzyme is not only capable of converting crotonyl-coenzyme A into ethylmalonyl-coenzyme A, but also of converting acrylyl-coenzyme A into methylmalonyl-coenzyme A.

Suitable genes for the enzymes $E_2$ to $E_4$ have already been mentioned in connection with the first variant of the process according to the invention, where it is also preferred in connection with the second variant, the above-described gene from *Sulfolobus tokodaii* is especially preferred as gene for the enzyme $E_3$.

According to an especially preferred variant of the third special embodiment of the process according to the invention, a genetically modified cell is used which features at least one activity of the enzyme $E_2$ and $E_{62}$ or of the enzymes $E_2$, $E_3$ and $E_{62}$ which is increased in comparison with its wild type, where the enzyme $E_2$ or the enzymes $E_2$ and $E_3$ is encoded by a DNA sequence as shown in SEQ ID No 03 and the enzyme $E_{62}$ is encoded by a DNA sequence as shown in SEQ ID No 05. In this context, it is preferred when the increased activity of these two enzymes is achieved by overexpressing, in the cell, the polypeptides with SEQ ID No 04 and SEQ ID No 06 or else that amino acid sequences with at least 50%, preferably at least 55%, more preferably at least 60%, more preferably at least 65% and most preferably at least 70% identity with the amino acid sequence as shown in SEQ ID No 04 and SEQ ID No 06, respectively. In this context, these two DNA sequences may be integrated into the genome of the cell or else be present on a vector inside the cell.

In connection with the above-described third special embodiment of the process according to the invention, it may furthermore be advantageous when the genetically modified cell used features not only an increase in the activity of the enzyme $E_{62}$ and/or of the activity of the enzyme $E_2$ or of the enzymes $E_2$ and $E_3$, but at least one, preferably both, of the following properties:

an activity of an enzyme $E_{11}$, which catalyzes the conversion of pyruvate into oxaloacetate or of an enzyme $E_{74}$, which catalyzes the conversion of phosphoenolpyruvate into oxaloacetate, but preferably of an enzyme $E_{11}$, which catalyzes the conversion of pyruvate into oxaloacetate, which is increased in comparison with its wild type and an increased activity of an enzyme $E_{75}$, which catalyzes the conversion of aspartate into beta-alanine.

The enzyme $E_{11}$ preferably takes the form of a carboxylase, especially preferably of a pyruvate carboxylase (EC number 6.4.1.1), which catalyzes the conversion of pyruvate into oxaloacetate. A pyruvate carboxylase which is especially preferred in this context is the mutant which is described in "*A novel methodology employing Corynebacterium glutamicum genome information to generate a new L-lysine-producing mutant*." Ohnishi J et al., Applied Microbiology and Biotechnology, Vol. 58 (2), pages 217-223 (2002). In this mutation, the amino acid proline at position 458 has been substituted by serine. The disclosure of this publication with regard to the possibilities of preparing pyruvate carboxylate mutants is hereby incorporated by referent and forms part of the disclosure of the present invention.

The enzyme $E_{75}$ preferably takes the form of a decarboxylase, especially preferably of a glutamate decarboxylate or of an aspartate decarboxylase, with a 1-aspartate 1-decarboxylase (EC number 4.1.1.11) which is encoded by the panD gene being most preferred. Aspartate decarboxylase catalyzes the conversion of aspartate into beta-alanine. Genes for aspartate decarboxylase (panD genes) from, inter alia, *Escherichia coli* (FEMS Microbiology Letters, 143, pages 247-252 (1996)), "*Photorhabdus luminescens* subsp. *Laumondii, Mycobacterium bovis* subsp. *Bovis*") and from a large number of other microorganisms have already been cloned and sequenced. DE-A-198 55 313 describes in particular the nucleotide sequence of the panD gene from *Corynebacterium glutamicum*. In principle, it is possible to use panD genes of any feasible origin, no matter whether from bacteria, yeasts or fungi. Furthermore, it is possible to employ all alleles of the panD gene, in particular also those which are the result of the degeneracy of the genetic code or of function-neutral sense mutations. An aspartate decarboxylase which is especially preferred according to the invention, besides the aspartate decarboxylase from *Corynebacterium glutamicum*, is the *Escherichia coli* mutant DV9 (Vallari and Rock, Journal of Bacteriology, 164, pages 136-142 (1985)). The disclosure of this publication with regard to the abovementioned mutant is hereby incorporated by reference and forms part of the disclosure of the present invention. The preparation of recombinant cells in which both the activity of the pyruvate carboxylase and the activity of the aspartate decarboxylase is increased is described in DE-A-10 2005 048 818.

According to a second variant of the process according to the invention, the formation of 3-hydroxyisobutyric acid or of polyhydroxyalkanoates based on 3-hydroxyisobutyric acid takes place via 3-hydroxyisobutyryl-coenzyme A as precursor.

In the event that, in the process according to the invention, a cell is used, in which the formation of 3-hydroxyisobutyric acid or of polyhydroxyalkanoates based on 3-hydroxyisobutyric acid takes place via 3-hydroxyisobutyryl-coenzyme A as precursor, as specified in the second variant, it is preferred according to a first special embodiment that the formation of 3-hydroxyisobutyric acid or of the polyhydroxyalkanoate based on 3-hydroxyisobutyric acid takes place via isobutyryl-coenzyme A as intermediate, where the cell is capable of preferentially utilizing carbohydrates, glycerol or L-valine as carbon source.

In the event that carbohydrates or glycerol act as the carbon source, it is preferred, according to a first alternative of this first special embodiment of the second variant of the process according to the invention to use a genetically modified cell which features an activity of at least one of the following enzymes $E_{76}$ to $E_{79}$, $E_{60}$, $E_{61}$ and $E_8$ which is increased in comparison with its wild type (see FIG. 19):

of an enzyme $E_{76}$, which catalyzes the conversion of pyruvate into 2-acetolactate;

of an enzyme $E_{77}$, which catalyzes the conversion of 2-acetolactate into 2,3-dihydroxyisovalerate;

of an enzyme $E_{78}$, which catalyzes the conversion of 2,3-dihydroxyisovalerate into 2-oxoisovalerate;

of an enzyme $E_{79}$, which catalyzes the conversion of 2-oxoisovalerate into isobutyryl-coenzyme A;

of an enzyme $E_{60}$, which catalyzes the conversion of isobutyryl-coenzyme A into methacrylyl-coenzyme A;

of an enzyme $E_{61}$, which catalyzes the conversion of methacrylyl-coenzyme A into 3-hydroxyisobutyryl-coenzyme A;

of an enzyme $E_8$, which catalyzes the conversion of 3-hydroxyisobutyryl-coenzyme A into 3-hydroxy-isobutyrate.

Genetically modified cells are especially preferably used in accordance with the invention, in which the activity of the following enzymes or enzyme combinations is increased: $E_8$, $E_{60}$, $E_{61}$, $E_{76}$, $E_{77}$, $E_{78}$, $E_{79}$ and $E_8E_{60}E_{61}E_{76}E_{77}E_{78}E_{79}$.

In this context, it is especially preferred that the enzyme $E_8$ is a 3-hydroxyisobutyryl-coenzyme A hydrolase (EC 3.1.2.4), $E_{76}$ is an acetolactate synthase (EC 2.2.1.6), $E_{77}$ is a dihydroxyisovalerate dehydrogenase (EC 1.1.1.86), $E_{78}$ is a 2,3-dihydroxyisovalerate dehydratase (EC 4.2.1.9), $E_{79}$ is a 2-oxoisovalerate dehydrogenase (EC 1.2.1.25 or EC 1.2.4.4), $E_{60}$ is an acyl-coenzyme A dehydrogenase (EC 1.3.99.3), a butyryl-coenzyme A dehydrogenase (EC 1.3.99.2) or a 2-methylacyl-coenzyme A dehydrogenase (EC 1.3.99.12), and $E_{61}$ is an enoyl-coenzyme A hydratase (EC 4.2.1.17).

Preferred enzymes $E_8$, $E_{60}$ and $E_{61}$ are those which have already been described above.

The enzyme $E_{76}$ is preferably encoded by genes selected from the group consisting of ilvbl, t8p19.70, ilv1, ilv2, ilv6, aal021wp, ael305 cp, ilvI, ilvH, ilvN, ilvB, ilvM, ilvG, ilvN, budB, ilvN-1, ilvN-2, atrC, ilvX, iolD, budB, alsS, ilvK, ilvB1, ilvB2, ilvB3, ilvN1, ilvN2, cgl1271, cgl1272, iolD and scc57A.40c.

The enzyme $E_{77}$ is preferably encoded by genes selected from the group consisting of f14p22.200, ilv5, acl198Wp, ilvC, ilvY, ilvC-1, ilvC-2, ilvC-3 and cgl1273, where the ilvC gene is most preferred.

The enzyme $E_{78}$ is preferably encoded by genes selected from the group consisting of f14o13.18, ilv3, acl117wp, ilvD, cgl1268, ilvD1 and ilvD2, where ilvD is most preferred.

In the event that L-valine acts as carbon source, it is preferred according to a second modification of the first special embodiment of the second alternative of the process according to the invention, where a genetically modified cell is used, in which the formation of 3-hydroxyisobutyric acid or of polyhydroxyalkanoates based on 3-hydroxyisobutyric acid takes place via 3-hydroxyisobutyryl-coenzyme A as precursor and isobutyryl-coenzyme A as intermediate, that this used cell features an activity of at least one of the following enzymes $E_{79}$, $E_{80}$, $E_{60}$, $E_{61}$ and $E_8$ which is increased in comparison with its wild type (see FIG. 20):

of an enzyme $E_{80}$, which catalyzes the conversion of L-valine into 2-oxoisovalerate;

of an enzyme $E_{79}$, which catalyzes the conversion of 2-oxoisovalerate into isobutyryl-coenzyme A;

of an enzyme $E_{60}$, which catalyzes the conversion of isobutyryl-coenzyme A into methacrylyl-coenzyme A;

of an enzyme $E_{61}$, which catalyzes the conversion of methacrylyl-coenzyme A into 3-hydroxyisobutyryl-coenzyme A;

of an enzyme $E_8$, which catalyzes the conversion of 3-hydroxyisobutyryl-coenzyme A into 3-hydroxyisobutyrate.

Genetically modified cells are especially preferably used in accordance with the invention, in which the activity of the following enzymes or enzyme combinations is increased: $E_8$, $E_{60}$, $E_{61}$, $E_{79}$, $E_{80}$ and $E_8E_{60}E_{61}E_{79}E_{80}$.

In this context, it is especially preferred that the enzyme $E_8$ is a 3-hydroxyisobutyryl-coenzyme A hydrolase (EC 3.1.2.4), $E_{60}$ is an acyl-coenzyme A dehydrogenase (EC 1.3.99.3), a butyryl-coenzyme A dehydrogenase (EC 1.3.99.2) or a 2-methylacyl-coenzyme A dehydrogenase (EC 1.3.99.12), $E_{61}$ is an enoyl-coenzyme A hydratase (EC 4.2.1.17), $E_{79}$ is a 2-oxoisovalerate dehydrogenase (EC 1.2.1.25 or EC 1.2.4.4), and $E_{80}$ is an amino acid transferase (EC 2.6.1.42).

Preferred enzymes $E_8$, $E_{60}$, $E_{61}$ and $E_{79}$ are those which have already been described above.

The enzyme $E_{80}$ is preferably encoded by genes selected from the group consisting of bcat1, bcat2, t27I1.8, t27i1.9, f2j10.5, f2j10.4, t12h1.16, mmb12.20, t9c5.3, mpa24.13, bat1, bat2, adl384wp, eca39, bcaA, ilvE, ilvE1, ilvE2, ilvE3, ywaA, ybgE, bcaT and cgl2204, where ilvE is especially preferred.

The nucleotide sequences of suitable genes the enzyme $E_{80}$ can, again, be found in the KEGG database, the NCBI database or the EMBL database.

In connection with this second alternative of the first special embodiment of the second variant of the process according to the invention, it may furthermore be advantageous to use a genetically modified cell in which the activity of an enzyme $E_4$ which catalyzes the conversion of methylmalonate-semialdehyde into 3-hydroxyisobutyric acid is reduced, where this enzyme $E_4$ preferably takes the form of a 3-hydroxyisobutyrate dehydrogenase (EC 1.1.1.31) or of a 3-hydroxyacyl-coenzyme A dehydrogenase (EC 1.1.1.35).

According to the second modification of the first special embodiment of the second variant of the process according to the invention, where a genetically modified cell is used, in which the formation of 3-hydroxyisobutyric acid or of polyhydroxyalkanoates based on 3-hydroxyisobutyric acid takes place via 3-hydroxyisobutyryl-coenzyme A as precursor and isobutyryl-coenzyme A as intermediate and starting from L-valine as carbon source, it may furthermore be preferred to employ those cells which are already capable of forming large amounts of L-valine. In this context, suitable cells are in particular those which have been described by Blombach et al. in *Applied Environmental Microbiology*, Vol. 73 (7) (2007), pages 2079-2084.

According to a special embodiment of the process according to the invention, it is furthermore preferred that the genetically modified cell used features an expression of the glb0 gene which is increased in comparison with its wild type. Furthermore, it may under certain circumstances be preferred that the genetically modified cell used features an activity of the citrate transport protein which is encoded by the dctA gene or the citP gene, which activity is reduced in comparison with its wild type.

The genetically modified cell used in the process according to the invention may preferably be obtained by a process comprising the method step of increasing the activity of at least one of the above-described enzymes, preferably of one or more of the enzymes $E_1$ to $E_4$,
$E_1$, $E_4$, $E_5$, $E_6$ and $E_7$,
$E_1$, $E_4$, $E_5$ and $E_7$,
$E_4$, $E_5$ and $E_{47}$ to $E_{52}$,
$E_2$ to $E_4$, $E_6$, $E_7$ and $E_{47}$ to $E_{52}$,
$E_2$ to $E_4$, $E_7$ and $E_{47}$ to $E_{52}$,
$E_8$ and $E_{53}$ to $E_{61}$,
$E_8$, $E_{53}$ to $E_{55}$, $E_{58}$ and $E_{62}$ to $E_{64}$,
$E_2$ to $E_3$, $E_{62}$, $E_{72}$ and $E_{73}$,
$E_8$, $E_{60}$, $E_{61}$ and $E_{76}$ to $E_{79}$ or
$E_8$, $E_{60}$, $E_{61}$, $E_{79}$ and $E_{80}$ in the cell, where increasing the enzymatic activity is preferably carried out by the methods described at the outset.

In the process step IA) of the process according to the invention, the genetically modified cells can be into contact with the nutrient medium, and thus cultured, either continuously or batchwise in the batch method or in the fed-batch method or in the repeated-fed-batch method in order to produce 3-hydroxyisobutyrate or polyhydroxyalkanoates based on 3-hydroxyisobutyrate. A semicontinuous method as described in GB-A-1009370 is also feasible. An overview over known culture methods are described in the textbook by Chmiel ("*Bioprozesstechnik* 1. *Einführung in die Bioverfahrenstechnik*" [Bioprocess technology 1. introduction to bioprocess technology] (Gustav Fischer Verlag, Stuttgart, 1991)) or in the textbook by Storhas ("*Bioreaktoren and periphere Einrichtungen*", [Bioreactors and peripheral equipment] Vieweg Verlag, Braunschweig/Wiesbaden, 1994).

The culture medium to be used must suitably meet the requirements of the strains in question. Descriptions of culture media for various microorganisms can be found in the textbook "*Manual of Methods for General Bacteriology*" of the American Society for Bacteriology (Washington D.C., USA, 1981).

Carbon sources which may be used are carbohydrates such as, for example, glucose, sucrose, lactose, fructose, maltose, molasses, starch and cellulose, oils and fats such as, for example, soy oil, sunflower oil, peanut oil and coconut fat, fatty acids such as, for example, palmitic acid, stearic acid and linolic acid, alcohols such as, for example, glycerol and methanol, hydrocarbons such as methane, amino acids such as L-glutamate or L-valine, or organic acids such as, for example, acetic acid. These substances may be used singularly or as a mixture. It is especially preferred to employ carbohydrates, in particular monosaccharides, oligosaccharides or polysaccharides, as described in U.S. Pat. No. 6,01,494 and U.S. Pat. No. 6,136,576, or $C_5$-sugars, or glycerol.

Nitrogen sources which can be used are organic nitrogen-comprising compounds such as peptones, yeast extract, meat extract, malt extract, cornsteep liquor, soya mill and urea, or inorganic compounds such as ammonium sulfate, ammonium chloride, ammonium phosphate, ammonium carbonate and ammonium nitrate. The nitrogen sources can be used singularly or as a mixture.

Phosphoric acid, potassium dihydrogen phosphate or dipotassium hydrogen phosphate or the corresponding sodium-comprising salts can be used as sources of phosphorus. The culture medium must furthermore comprise salts of metals such as, for example, magnesium sulfate or iron sulfate, which are required for growth. Finally, essential growth factors such as amino acids and vitamins may be employed in addition to the abovementioned substances. Moreover, suitable precursors may be added to the culture medium. The abovementioned input materials may be added to the culture in the form of a single batch or else fed in a suitable manner during culturing.

The pH for the culture can be controlled by employing, in an appropriate manner, basic compounds such as sodium hydroxide, potassium hydroxide, ammonia and aqueous ammonia, or acidic compounds such as phosphoric acid or sulfuric acid. Foaming can be controlled by employing anti-foams such as, for example, fatty acid polyglycol esters. To maintain the stability of plasmids, it is possible to add to the medium suitable substances which have a selective effect, such as, for example, antibiotics. Aerobic conditions are maintained by introducing, into the culture, oxygen or oxygen-containing gas mixtures such as, for example, ambient air. The culture temperature is normally 20° C. to 45° C. and preferably 25° C. to 40° C. It may be preferred to employ, as cells, those cells which are described in U.S. Pat. No. 6,803,218, in particular when using cells which are capable of converting glycerol as the substrate. In this case, the cells can be cultured at temperatures in the range of from 40 to 100° C.

The isolation of 3-hydroxyisobutyric acid from the nutrient solution is preferably carried out continuously, it being furthermore preferred in this context also to produce 3-hydroxyisobutyric acid by fermentation in a continuous manner, so that the entire process from the production of 3-hydroxyisobutyric acid up to its isolation from the fermentation liquor can be carried out continuously. For the continuous isolation of the production of 3-hydroxyisobutyric acid from the fermentation liquor, the former is continuously passed over a device for removing the microorganisms employed during fermentation, preferably through a filter with an exclusion level in the range of from 20 to 200 kDa, where a solid/liquid separation takes place. It is also feasible to employ a centrifuge, a suitable sedimentation device or a combination of these devices, it being especially preferred to first separate at least part of the microorganisms by sedimentation and subsequently to feed the fermentation liquor, which has been freed from part of the microorganisms, to ultrafiltration or to a centrifugation device.

After the microorganisms have been removed, the fermentation product, which is enriched with regard to its 3-hydroxyisobutyric acid fraction, is fed to a separation system, preferably a multistep separation system. This separation system provides a plurality of separation steps which are connected in series, from which steps in each case return lines lead away and back to the fermentation tank. Furthermore, exit pipes lead out of the respective separation steps. The individual separation steps may operate by the electrodialysis, the reverse osmosis, the ultrafiltration or the nanofiltration principle. As a rule, these are membrane separation devices in the individual separation steps. The selection of the individual separation steps is a function of the nature and the extent of the fermentation by-products and substrate residues.

Besides the 3-hydroxyisobutyric acid being separated off by means of electrodialysis, reverse osmosis, ultrafiltration or nanofiltration, in the course of which an aqueous 3-hydroxyisobutyric acid solution is obtained as the end product, the 3-hydroxyisobutyric acid can also be separated off by extractive methods from the fermentation solution which has been freed from microorganisms, in which case, finally, the pure 3-hydroxyisobutyric acid can be obtained. To separate the 3-hydroxyisobutyric acid by extraction, it is possible to add, to the fermentation solution, for example ammonium compounds or amines in order to form an ammonium salt of 3-hydroxyisobutyric acid. This ammonium salt can then be separated from the fermentation solution by adding an organic extractant and subsequently heating the resulting mixture, whereby the ammonium salt is concentrated in the organic phase. Then, the 3-hydroxyisobutyric acid can be isolated from this phase for example by further extraction steps, giving the pure 3-hydroxyisobutyric acid. More details regarding the separation method can be found in WO-A-02/090312, whose disclosure regarding the separation of hydroxycarboxylic acids from fermentation solutions is hereby incorporated by reference and forms part of the disclosure of the present application.

Depending on the way in which the 3-hydroxyisobutyric acid is separated from the fermentation solution, either an aqueous solution of 3-hydroxyisobutyric acid comprising 2 to 90% by weight, preferably 7.5 to 50% by weight and especially preferably 10 to 25% by weight of 3-hydroxyisobutyric acid, or else pure 3-hydroxyisobutyric acid is obtained.

Furthermore, the 3-hydroxyisobutyric acid prepared in step IA) of the process according to the invention can also be neutralized, either before, during or after the purification, for which purpose bases such as, for example, calcium hydroxide or sodium hydroxide can be employed.

In process step IB) of the process according to the invention, the 3-hydroxyisobutyric acid is dehydrated with formation of methacrylic acid, for which purpose it is possible either to employ the pure 3-hydroxyisobutyric acid isolated from the fermentation solution or else the aqueous solution of 3-hydroxyisobutyric acid, which has been isolated when working up the fermentation solution, it also being possible to concentrate the aqueous solution of 3-hydroxyisobutyric acid, if appropriate, before the dehydration step, for example by means of distillation, if appropriate in the presence of a suitable entrainer.

The dehydration reaction can, in principle, be carried out in liquid phase or in the gas phase. Furthermore, it is preferred in accordance with the invention that the dehydration reaction is carried out in the presence of a catalyst, with the nature of the catalyst employed depending on whether a gas-phase or a liquid-phase reaction is carried out.

Suitable dehydration catalysts are both acidic catalysts and alkaline catalysts. Acidic catalysts are preferred, in particular because they show less tendency to form oligomers. The dehydration catalyst may be employed both as a homogeneous and as a heterogeneous catalyst. If the dehydration catalyst is present in the form of a heterogeneous catalyst, it is preferred that the dehydration catalyst is in contact with a support x. Suitable supports x are all solids believed by the skilled worker to be suitable. In the present context, it is preferred that the solids have suitable pore volumes which are suitable for good binding and absorption of the dehydration catalyst. Furthermore, total pore volumes as specified by DIN 66133 in a range of from 0.01 to 3 ml/g are preferred, and total pore volumes in the range of from 0.1 to 1.5 ml/g are especially preferred. Moreover, it is preferred that the solids which are suitable as support x have a surface area in the range of from 0.001 to 1000 $m^2/g$, preferably in the range of from 0.005 to 450 $m^2/g$ and furthermore preferred in the range of from 0.01 to 300 $m^2/g$ as determined by BET test as specified in DIN 66131. A support which may be employed for the dehydration catalyst can firstly be bulk material with a mean particle diameter in the range of from 0.1 to 40 mm, preferably in the range of from 1 to 10 mm, and furthermore preferably in the range from 1.5 to 5 mm. The wall of the dehydration reactor may furthermore act as support. Furthermore, the support may be acidic or alkaline per se, or else an acidic or alkaline dehydration catalyst may be applied to an inert support. Application techniques which may be mentioned in particular are immersion or impregnation or else incorporation into a support matrix.

Suitable supports x, which may also feature dehydration catalyst properties, are, in particular, natural or synthetic silicates such as, in particular, mordenite, montmorillonite, acidic zeolites; supports which are coated with monobasic, dibasic or polybasic inorganic acids, in particular phosphoric acid, or with acidic salts of inorganic acids, such as substances of the oxide or silicate type, for example $Al_2O_3$, $TiO_2$; oxides and mixed oxides such as, for example, $\gamma$-$Al_2O_3$ and $ZnO$—$Al_2O_3$ mixed oxides of the heteropolyacids.

In accordance with an embodiment according to the invention, the support x consists at least in part of a compound of the oxide type. Such compounds of the oxide type should feature at least one of the elements selected from among Si, Ti, Zr, Al, P or a combination of at least two of these. Such supports may also act as dehydration catalyst themselves, owing to their acidic or alkaline properties. A preferred class of compounds, both as support by way of x and by way of dehydration catalyst comprise silicon/aluminum/phosphorus oxides. Preferred alkaline substances which act both as dehydration catalyst and also as support x comprise alkali, alkaline earth, lanthanum, lanthoids or a combination of at least two of these in the form of their oxides. Such acidic or alkaline dehydration catalysts are commercially available both from Degussa AG and from Südchemie AG. A further class are ion exchangers. Again, these may be present both in alkaline and in acidic form.

Suitable homogeneous dehydration catalysts are, in particular, inorganic acids, preferably phosphorus-containing acids and furthermore preferably phosphoric acid. These inorganic acids can be immobilized on the support x by immersion or impregnation.

The use of heterogeneous catalysts has proved particularly advantageous in particular in the case of gas phase dehydration. In the case of liquid-phase dehydration, however, both homogeneous and heterogeneous dehydration catalysts are employed.

Furthermore, it is preferred that the method according to the invention involves the use of a dehydration catalyst with an $H_0$ value in the range of from +1 to −10, preferably in the range of from +2 to −8.2 and furthermore preferably, in the case of liquid-phase dehydration, in the range of from +2 to −3 and in gas-phase dehydration in the range of from −3 to −8.2. The $H_0$ value corresponds to the acid function as defined by Hämmert and can be determined by what is known as amine titration and the use of indicators, or by the absorption of a gaseous base (see "*Studies in Surface Science and Catalytics*", vol. 51, 1989*: "New solid Acids and Bases, their catalytic Properties*", K. Tannabe et al).

According to a special embodiment of the method according to the invention, the acidic solid catalyst employed is a porous support structure which has been brought into contact with an inorganic acid, preferably with phosphoric acid or with superacids such as, for example, sulfated or phosphated zirconium oxide and which is based preferably on at least 90% by weight, furthermore preferably at least 95% by weight and most preferably at least 99% by weight of a silicon oxide, preferably an $SiO_2$. The bringing into contact of the porous support structure with the inorganic acid is preferably carried out by impregnating the support structure with the acid, with the latter preferably being brought into contact with the former in an amount in a range of from 10 to 70% by weight, especially preferably in the range of from 20 to 60% by weight and more preferably in a range of from 30 to 50% by weight, based on the weight of the support structure, followed by drying. After drying, the support structure is heated in order to fix the inorganic acid, preferably at a temperature in a range of from 300 to 600° C., more preferably in a range of from 400 to 500° C.

According to a special embodiment of the method according to the invention, the dehydration reaction is carried out in the gas phase. Here, it is possible to employ conventional apparatuses as are known to the skilled worker in the field of gas phase reaction, for example tubular reactors. It is especially preferred to employ shell-and-tube heat exchangers and reactors which comprise thermoplates as heat exchangers.

According to an embodiment of the gas-phase dehydration reaction, pure 3-hydroxyisobutyric acid is introduced into a reactor comprising one of the abovementioned fixed-bed catalysts. According to another embodiment, the 3-hydroxyisobutyric acid is introduced into the reactor in the form of an aqueous solution comprising 2 to 80% by weight, especially preferably 5 to 50% by weight and more preferably 10 to 25% by weight of 3-hydroxyisobutyric acid, in each case based on the total weight of the aqueous solution. The pressure and temperature conditions inside the reactor are chosen such that the 3-hydroxyisobutyric acid, or the aqueous solution, is present in gaseous form when entering the reactor. The dehydration in the gas phase is preferably carried out in the temperature range of between 200 and 400° C., especially preferably between 250 and 350° C. The pressure inside the reactor during the gas-phase dehydration reaction is preferably in a range of from 0.1 to 50 bar, especially preferably in a range of from 0.2 to 10 bar and most preferably in a range of from 0.5 to 5 bar.

The amount of 3-hydroxyisobutyric acid introduced into the reactor in the gas-phase dehydration reaction is preferably in a range of from 10 to 100% by volume, especially preferably in a range of from 20 to 100% by volume and most preferably in a range of from 30 to 100% by volume.

According to another special embodiment of the method according to the invention, the dehydration reaction is performed in the liquid phase. The liquid-phase dehydration reaction can also be carried out in all apparatuses which are known to the skilled worker and in which a fluid can be heated to a desired reaction temperature, during which process a pressure can be applied to the apparatus which is sufficient for maintaining the reaction components in the liquid state under the desired temperature conditions.

According to a special embodiment of the method according to the invention, the liquid-phase dehydration method comprises a first method step, in which pure 3-hydroxyisobutyric acid or an aqueous solution comprising 5 to 100% by weight, especially preferably 20 to 100% by weight and most preferably 50 to 100% by weight of 3-hydroxyisobutyric acid, based on the total weight of the aqueous solution, is introduced into a reactor. The pressure and temperature conditions inside the reactor are chosen such that the 3-hydroxyisobutyric acid, or the aqueous solution, is present in liquid form when entering the reactor. According to a special embodiment of the method according to the invention in which the dehydration reaction is carried out in the liquid phase, the 3-hydroxyisobutyric acid, or the aqueous solution, is passed in such a way over a fixed catalyst bed inside the dehydration reactor that the liquid phase trickles over the surface of the catalyst particles. Such a procedure may be carried out for example in a trickle-bed reactor.

The dehydration in the liquid phase is preferably carried out in a temperature range of between 200 and 350° C., especially preferably between 250 and 300° C. The pressure inside the reactor in the case of liquid-phase dehydration is preferably in a range of from 1 to 50 bar, especially preferably in a range of from 2 to 25 bar and most preferably in a range of from 3 to 10 bar.

The catalysis of the dehydration reaction may be homogeneous or heterogeneous, both in the case of gas-phase dehydration and in the case of liquid-phase dehydration.

In the case of homogeneous catalysis, the catalyst, which in this case preferably takes the form of an inorganic acid such as, for example, phosphoric acid or sulfuric acid, is first brought into contact with the pure 3-hydroxyisobutyric acid or with the aqueous solution comprising the 3-hydroxyisobutyric acid. Thereafter, the resulting composition is introduced into the reactor and converted into methacrylic acid under the desired pressure and temperature conditions. It is also feasible to introduce the inorganic acid independently of the 3-hydroxyisobutyric acid or the aqueous solution into the reactor. In this case, the reactor features at least two feed lines, one for the 3-hydroxyisobutyric acid, or the aqueous solution comprising 3-hydroxyisobutyric acid, and one for the catalyst. If the dehydration reaction is carried out in liquid phase in a trickle-bed reactor, it is preferred to introduce the catalyst together with the 3-hydroxyisobutyric acid, or the aqueous solution comprising the 3-hydroxyisobutyric acid, at the top of the reactor.

In the case of heterogeneous catalysis, the catalyst is in the form of a solid substrate located in the reaction space, for example in the form of a fixed bed, in the form of catalyst-coated plates, preferably thermoplates, which are arranged inside the reactor, or else in the form of catalyst-coated reactor walls. Reactors which are possible are described for example in DE-A-198 48 208, DE-A-100 19 381 and EP-A-I 234 612. In the case of heterogeneous catalysis, preferred catalysts are support structures which have been brought into contact with inorganic acids, preferably impregnated porous support structures. The 3-hydroxyisobutyric acid, or the aqueous solution comprising the 3-hydroxyisobutyric acid, is then brought into contact with the surface of the solid catalyst material in the form of a vapor, or in liquid form.

According to an especially preferred embodiment of the method according to the invention, the dehydration of the 3-hydroxyisobutyric acid is carried out in liquid phase at a pressure in the range of from 200 to 500 mbar, at a temperature in a range of from 200 to 230° C. and in the presence of alkali metal ions as the catalyst.

The reaction mixture which is obtained after the dehydration reaction is either an aqueous methacrylic acid solution which does not contain any catalyst components (such a solution is obtained in the case of heterogeneously catalyzed dehydration) or else an aqueous methacrylic acid solution which comprises catalysts (such a solution is obtained in the case of homogeneously catalyzed dehydration). Furthermore, the aqueous methacrylic acid solution may be in liquid form (if the dehydration reaction has been effected in the liquid phase) or in gaseous form (if the dehydration reaction has been carried out in the gas phase).

If appropriate, the resulting methacrylic acid solution can, according to a special embodiment of the method according to the invention, be esterified without further processing. In such a case, the methacrylic acid solution is brought into contact with suitable alcohols such as, for example, methanol, ethanol, 1-propanol, 2-propanol or 1-butanol and suitable esterification catalysts known to the skilled worker such as, for example, concentrated acids, with heating, and the methacrylic acid is so converted into the corresponding esters. However, it may be advantageous additionally to purify the methacrylic acid before esterification, it being possible to employ, in principle, any purification method which is known to the skilled worker and which is conventionally employed for the purification of contaminated (meth)acrylic acid obtained by catalytic gas-phase oxidation of propylene.

If the dehydration reaction has been carried out in the gas phase, it is preferred that the methacrylic acid is first condensed, generating an aqueous methacrylic acid solution. Here, any condensation method known to the skilled worker may be employed in principle, for example a fractional condensation as described in WO-A-2004/035514, WO-A-03/014172 or EP-A-EP 1 163 201 or by total condensation as described in EP-A-0 695 736. It is also feasible to add additional solvents, in particular water, during the condensation process in order to absorb the methacrylic acid as completely as possible.

The aqueous methacrylic acid solution obtained after condensation, or else the aqueous methacrylic acid solution obtained in the event of liquid-phase dehydration, can then be freed from water and other contaminants in further purification steps. Here, it is possible first to remove the water by azeotrope distillation in the presence of an entrainer as described, for example, in DE-A-198 53 064. It is also feasible to employ high-boiling organic solvents for absorbing the methacrylic acid, as is disclosed for example in EP-A-0 974 574. In addition to these distillation methods, membranes for dewatering may also be employed, as proposed for example in DE-A-44 01 405. Employing crystallization methods for purifying the aqueous methacrylic acid solution, which has been generated in the case of liquid-phase dehydration or which has been obtained by condensation, is furthermore feasible.

The methacrylic acid obtained after dehydration can be purified even further in further method steps. Thus, high-boiling contaminants which are still present can be removed by further distillation steps. However, it is especially preferred to further purify the methacrylic acid obtained by dehydration using crystallization methods as described for example in DE-A-101 49 353.

The resulting purified methacrylic acid can then be esterified, if appropriate.

A contribution to solving the problems mentioned at the outset is furthermore provided by a method of preparing methacrylic acid or methacrylic esters, comprising the method steps IIA) preparation of polyhydroxyalkanoates based on 3-hydroxyisobutyric acid by the method described above, IB) cleavage of the polyhydroxyalkanoates based on 3-hydroxyisobutyric acid with formation of 3-hydroxyisobutyric acid and, if appropriate, neutralization of the 3-hydroxyisobutyric acid and/or isolation of the 3-hydroxyisobutyric acid, IIC) dehydration of the 3-hydroxyisobutyric acid with formation of methacrylic acid and, if appropriate, esterification of the methacrylate or methacrylic acid.

A contribution to solving the problems mentioned at the outset is also provided by a method of preparing polymethacrylic acid or polymethacrylic esters, comprising the method steps IIIA) preparation of methacrylic acid by the method described above, IIIB) free-radical polymerization of the methacrylic acid, it being possible, if appropriate, to esterify at least in part the carboxyl groups of the methacrylic acid before or after the free-radical polymerization reaction.

The present invention will now be illustrated in greater detail with reference to nonlimiting figures and examples.

FIG. 1 shows the conversion of succinyl-coenzyme A into methylmalonyl-coenzyme A with catalysis by the enzyme $E_1$.

FIG. 2 shows the conversion of methylmalonyl-coenzyme A into 3-hydroxyisobutyric acid with catalysis by the enzymes $E_2$ to $E_4$ in accordance with the first alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 3 shows the conversion of (R)-methylmalonyl-coenzyme A into 3-hydroxyisobutyric acid with catalysis by the enzymes $E_4$, $E_6$ and $E_7$ in accordance with the second alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 4 shows the conversion of methylmalonyl-coenzyme A into 3-hydroxyisobutyric acid with catalysis by the enzymes $E_4$, $E_5$ and $E_7$ in accordance with the third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 5 shows the conversion of 3-hydroxyisobutyric acid into a polyhydroxyalkanoate with catalysis by the enzymes $E_8$ and $E_9$.

FIG. 6 shows the conversion of phosphoenolpyruvate or pyruvate into oxalacetate with catalysis by the enzymes $E_{10}$ or $E_{11}$ according to a special embodiment of the first, second or third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 7 shows the conversion of oxalacetate into succinyl-coenzyme A with catalysis by the enzymes $E_{12}$ to $E_{15}$ according to a first special embodiment of the first, second or third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 8 shows the conversion of oxalacetate into succinyl-coenzyme A with catalysis by the enzymes $E_{13}$ to $E_{16}$ and $E_{24}$ to $E_{25}$ according to a second special embodiment of the first, second or third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 9 shows the conversion of oxalacetate into succinyl-coenzyme A with catalysis by the enzymes $E_{16}$, $E_{24}$, $E_{27}$ and $E_{28}$ according to a third special embodiment of the first, second or third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 10 shows the conversion of L-glutamate into succinyl-coenzyme A with catalysis by the enzymes $E_{46}$ and $E_{28}$ in accordance with a further special embodiment of the first, second or third alternative of the process according to the invention, where a genetically modified cell is used, in which succinyl-coenzyme A is formed as intermediate and methylmalonate semialdehyde as precursor in the production of 3-hydroxyisobutyric acid or of polyhydroxyalkanoates based on 3-hydroxyisobutyric acid.

FIGS. 11 and 12 show the conversion of acetyl-coenzyme A into 3-hydroxyisobutyric acid with catalysis by the enzymes $E_4$, $E_5$ and $E_{47}$ to $E_{52}$ in accordance with a first alternative of the second special embodiment of the process according to the invention, where a genetically modified cell is used, in which propionyl-coenzyme A is formed as intermediate and methylmalonate semialdehyde as precursor in the production of 3-hydroxyisobutyric acid or of polyhydroxyalkanoates based on 3-hydroxyisobutyric acid.

FIGS. 13 and 14 show the conversion of propionyl-coenzyme A into 3-hydroxyisobutyric acid with catalysis by the enzymes $E_2$ to $E_4$, $E_6$, $E_7$ and $E_{47}$ to $E_{52}$ in accordance with a second alternative of the second special embodiment of the process according to the invention, where a genetically modified cell is used, in which propionyl-coenzyme A is formed as intermediate and methylmalonate semialdehyde as precursor in the production of 3-hydroxyisobutyric acid or of polyhydroxyalkanoates based on 3-hydroxyisobutyric acid.

FIGS. 15 and 16 show the conversion of propionyl-coenzyme A into 3-hydroxyisobutyric acid with catalysis by the enzymes $E_2$ to $E_4$, $E_7$ and $E_{47}$ to $E_{52}$ in accordance with a third alternative of the second special embodiment of the process according to the invention, where a genetically modified cell is used, in which propionyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 17 shows the conversion of two units of acetyl-coenzyme A into glyoxylate and propionyl-coenzyme A with catalysis by the enzymes $E_{53}$ to $E_{55}$, $E_{58}$ and $E_{62}$ to $E_{65}$ in accordance with a fifth alternative of the second special embodiment of the process according to the invention, where a genetically modified cell is used, in which propionyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 18 shows the conversion of β-alanine into 3-hydroxyisobutyric acid with catalysis by the enzymes $E_2$ to $E_4$, $E_{62}$, $E_{72}$ and $E_{73}$ according to a third special embodiment of the process according to the invention, where a genetically modified cell is used, in which acrylyl-coenzyme A is formed as intermediate and methylmalonate semialdehyde as precursor in the production of 3-hydroxyisobutyric acid or of polyhydroxyalkanoates based on 3-hydroxyisobutyric acid.

FIG. 19 shows the conversion of pyruvate into 3-hydroxyisobutyric acid with catalysis by the enzymes $E_{76}$ to $E_{79}$, $E_{60}$, $E_{61}$ and $E_8$ according to a first alternative of the first special embodiment of the second variant of the process according to the invention, where a genetically modified cell is used, in which isobutyryl-coenzyme A is formed as intermediate and 3-hydroxyisobutyryl-coenzyme A as precursor in the production of 3-hydroxyisobutyric acid or of polyhydroxyalkanoates based on 3-hydroxyisobutyric acid.

FIG. 20 shows the conversion of L-valine into 3-hydroxyisobutyric acid with catalysis by the enzymes $E_8$, $E_{60}$, $E_{61}$, $E_{79}$ and $E_{80}$ according to a second alternative of the first special embodiment of the second variant of the process according to the invention, where a genetically modified cell is used, in which isobutyryl-coenzyme A is formed as intermediate and 3-hydroxyisobutyryl-coenzyme A as precursor in the production of 3-hydroxyisobutyric acid or of polyhydroxyalkanoates based on 3-hydroxyisobutyric acid.

EXAMPLES

Example 1

Figure 1:
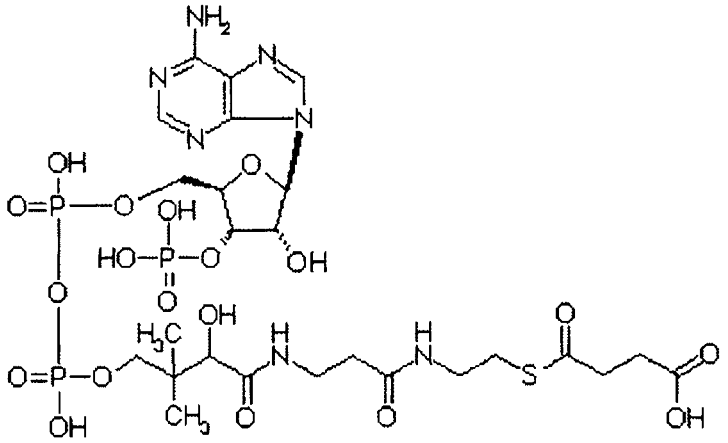
Figure 1:
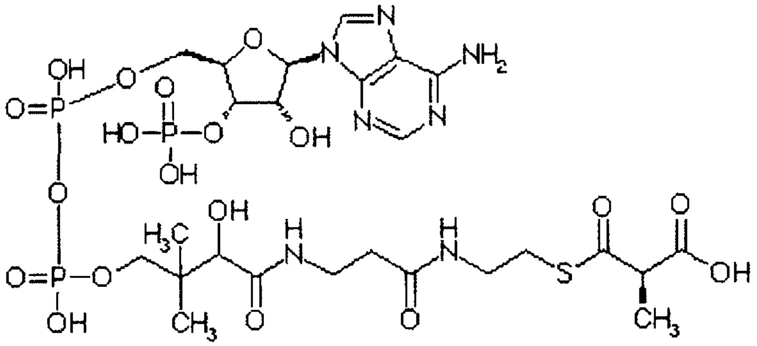
Figure 2:
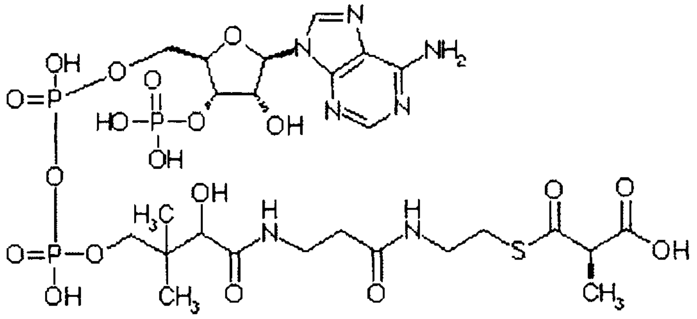
Figure 2:
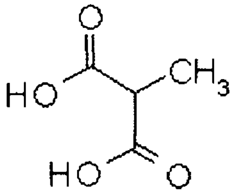
Figure 2:
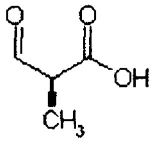
Figure 2:
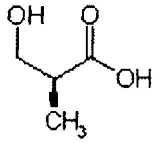
Figure 3:
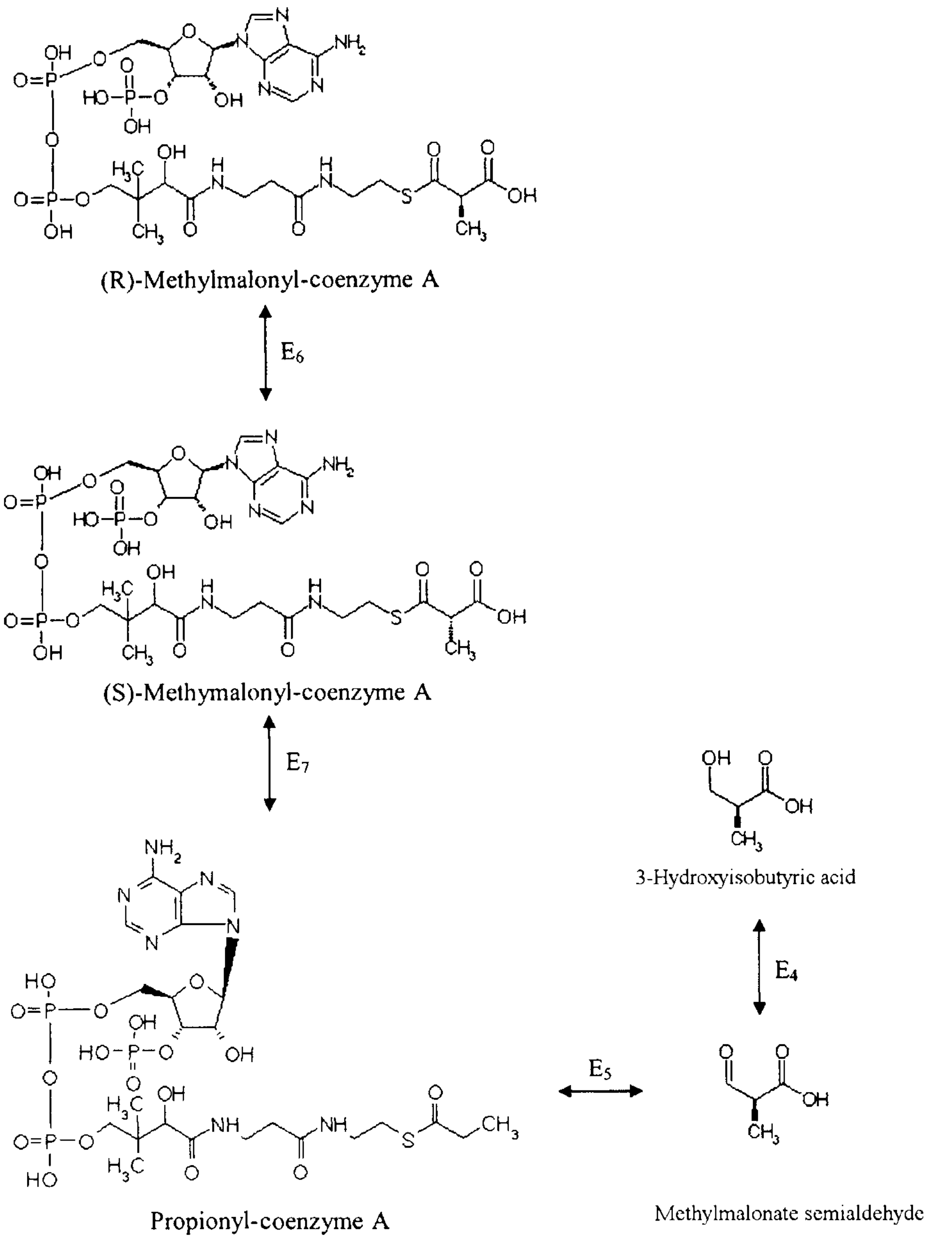
Figure 4:
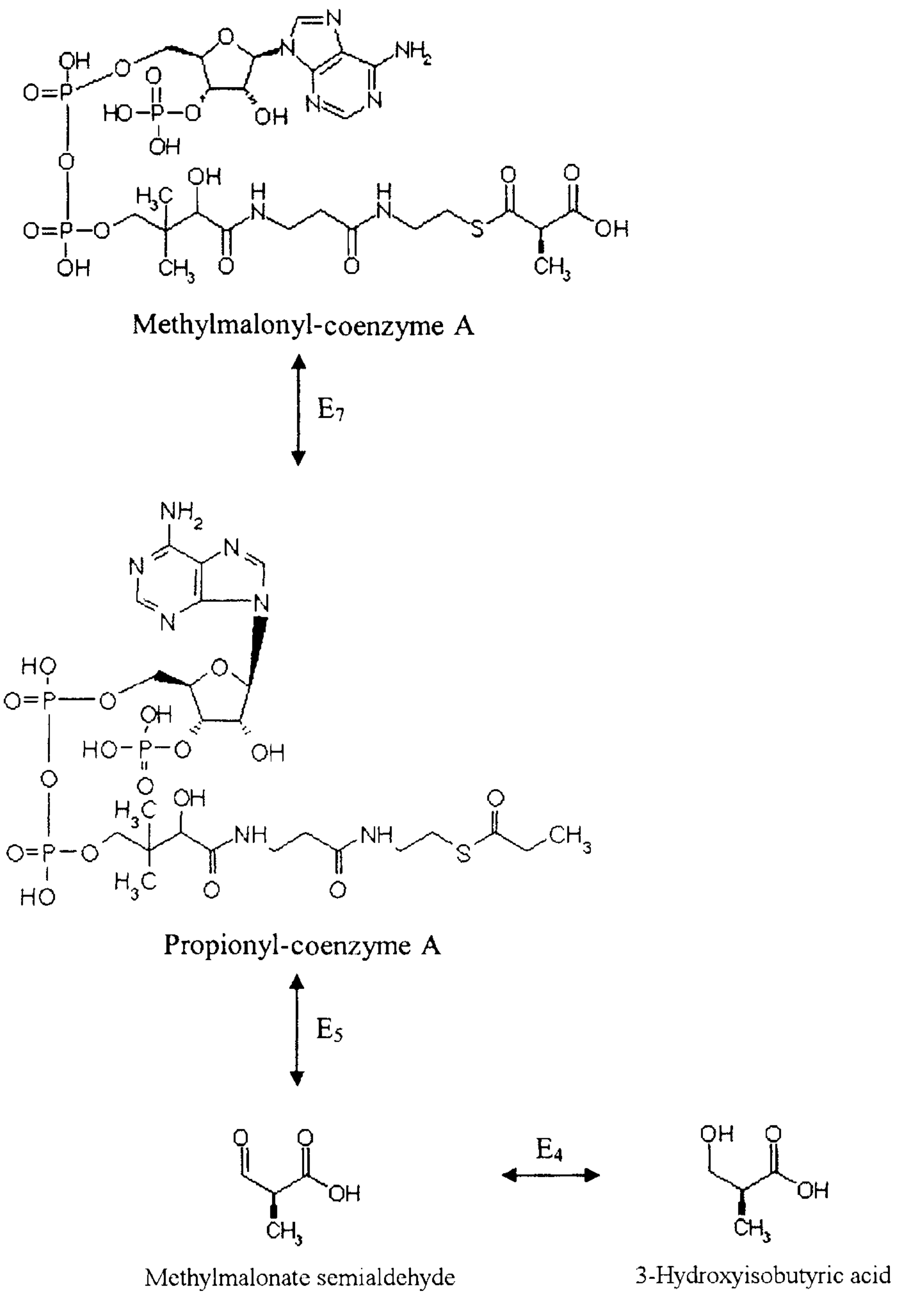
Figure 5:
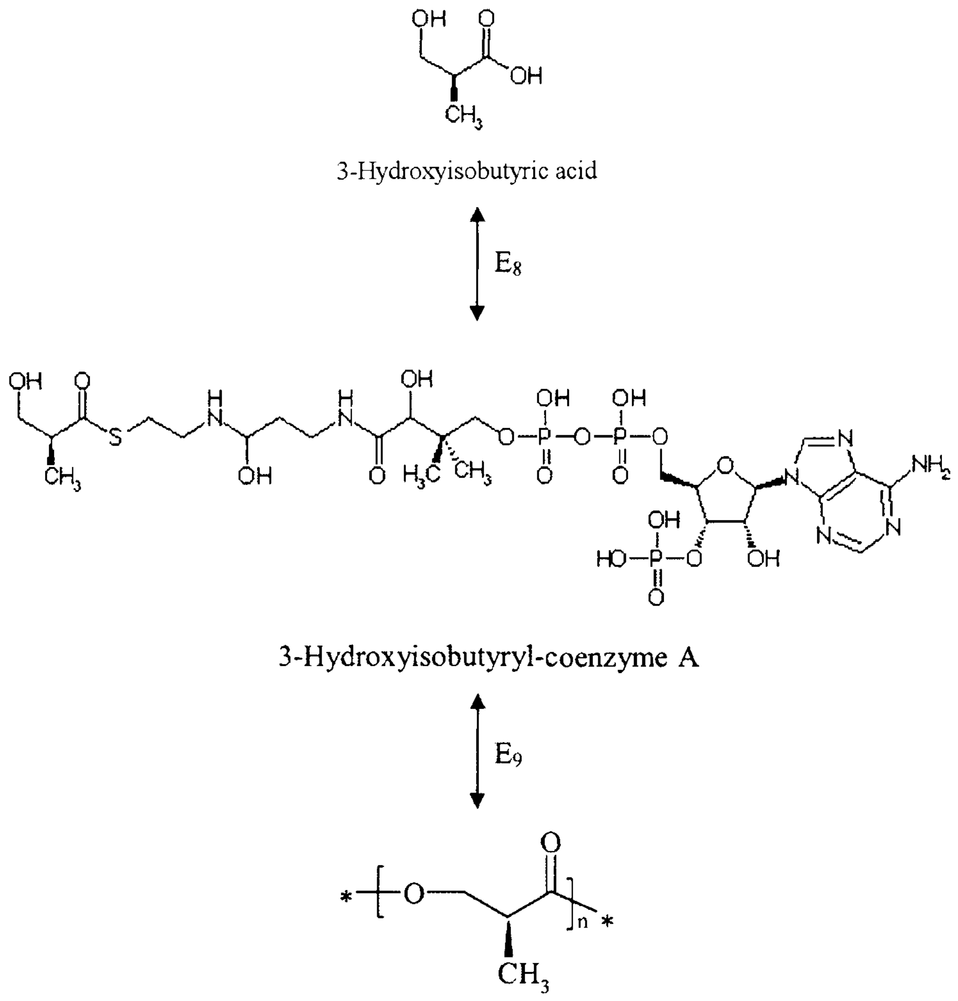
Figure 6:
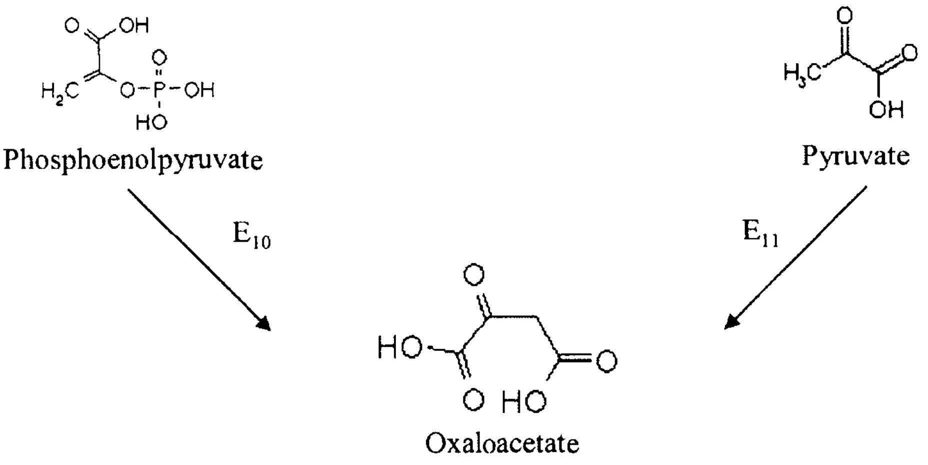
Figure 7:
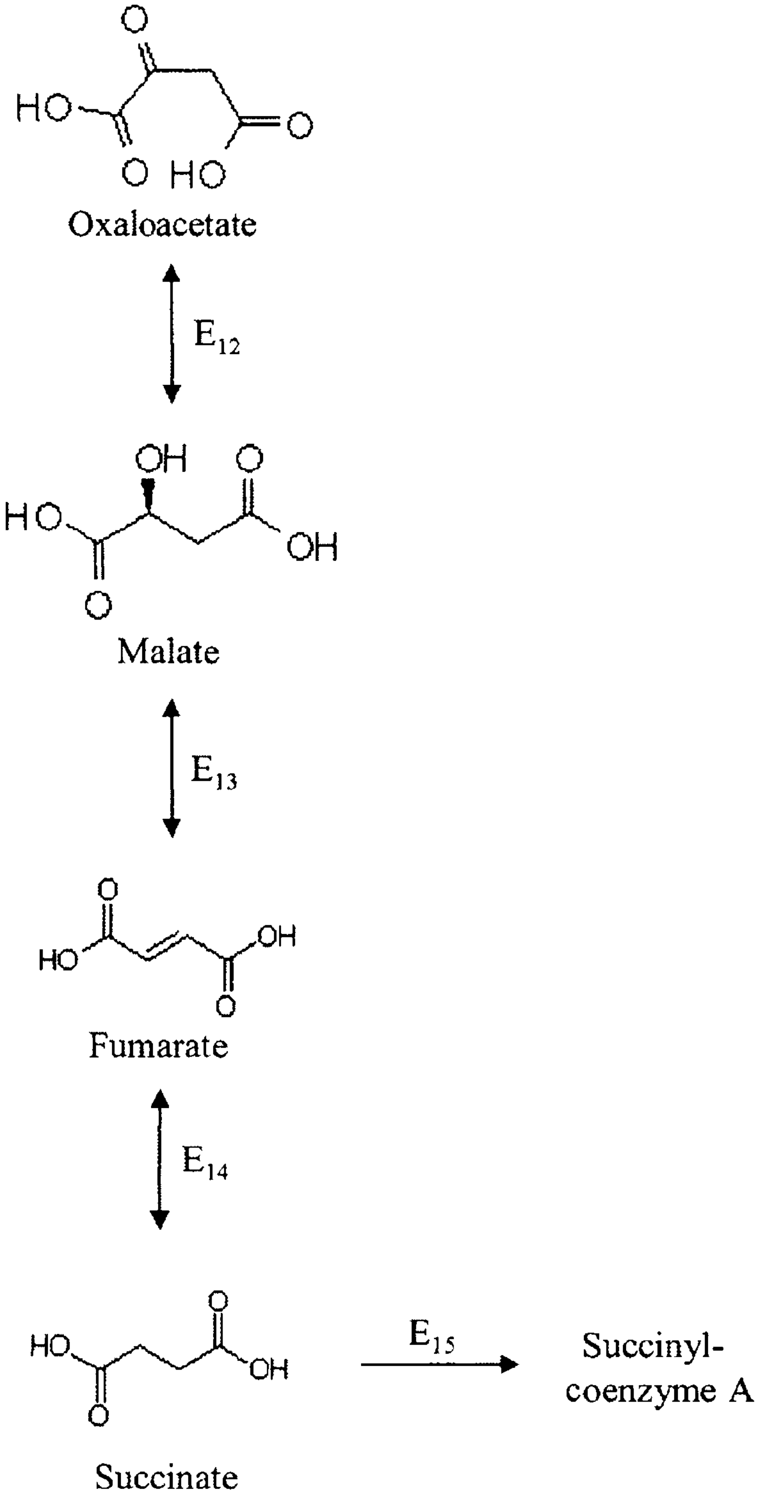
Figure 8:
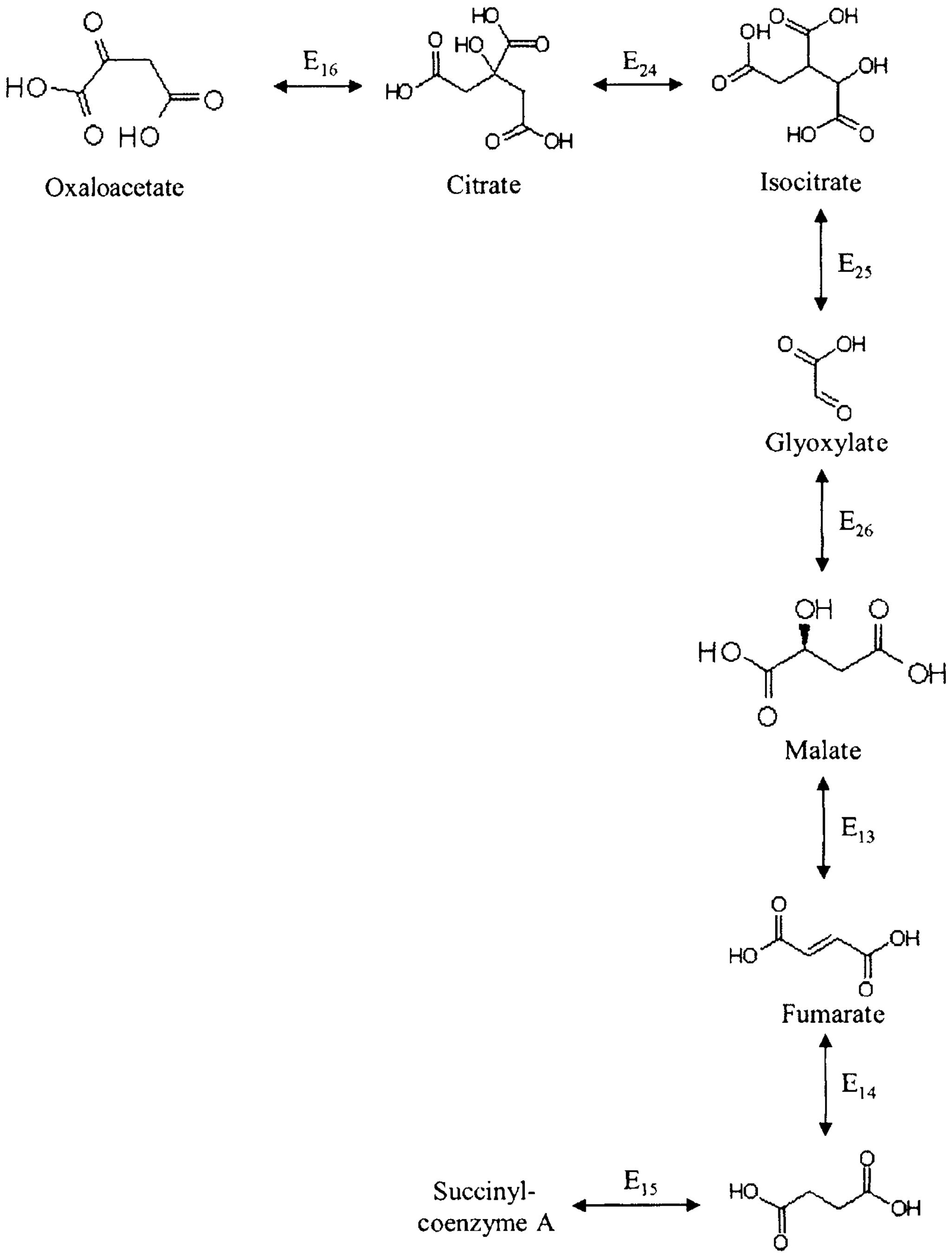
Figure 9:
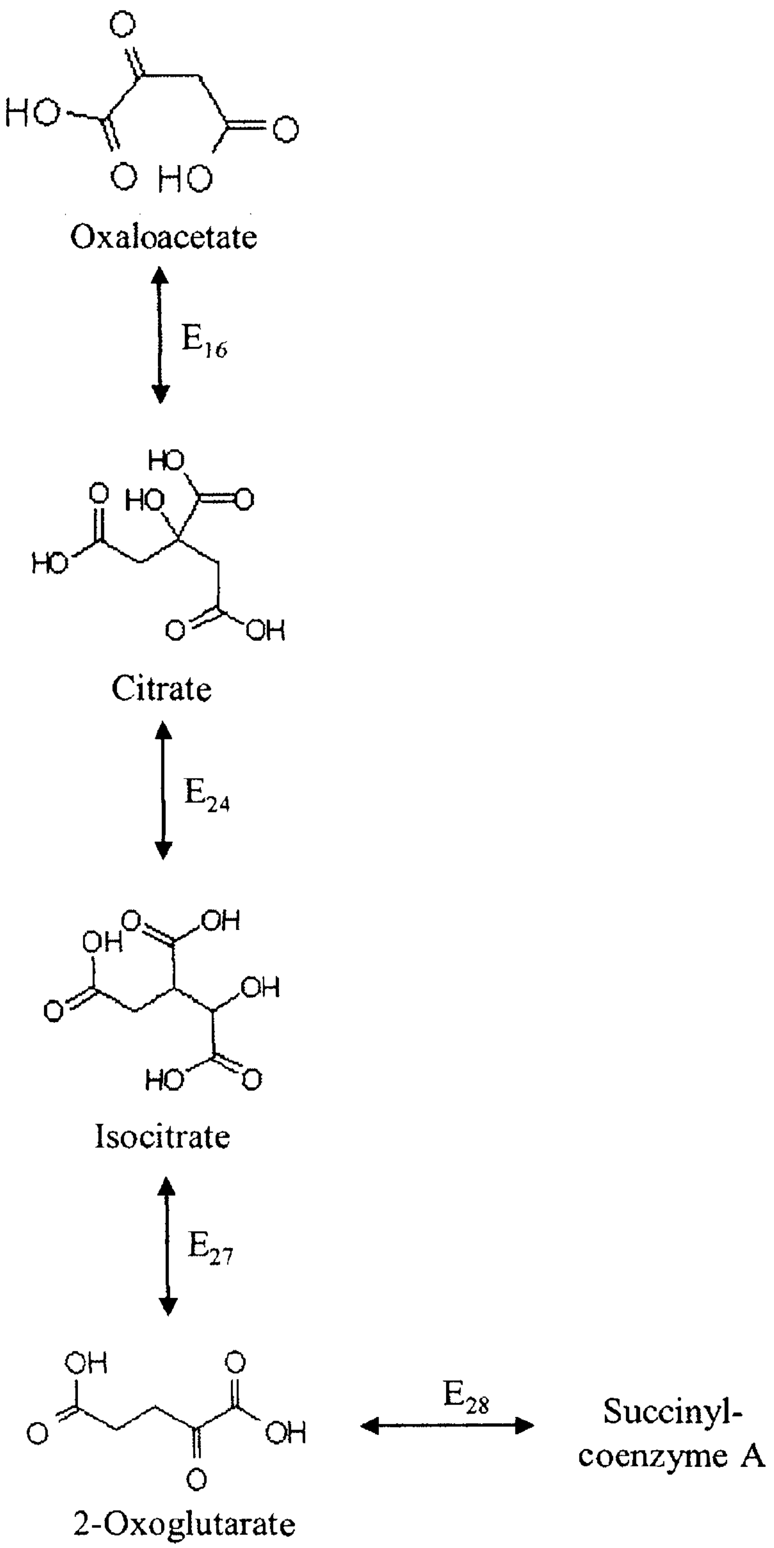
Figure 10:
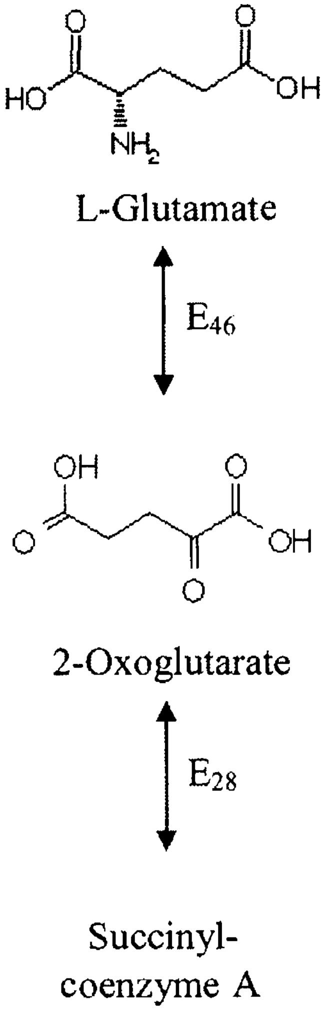
Figure 11:
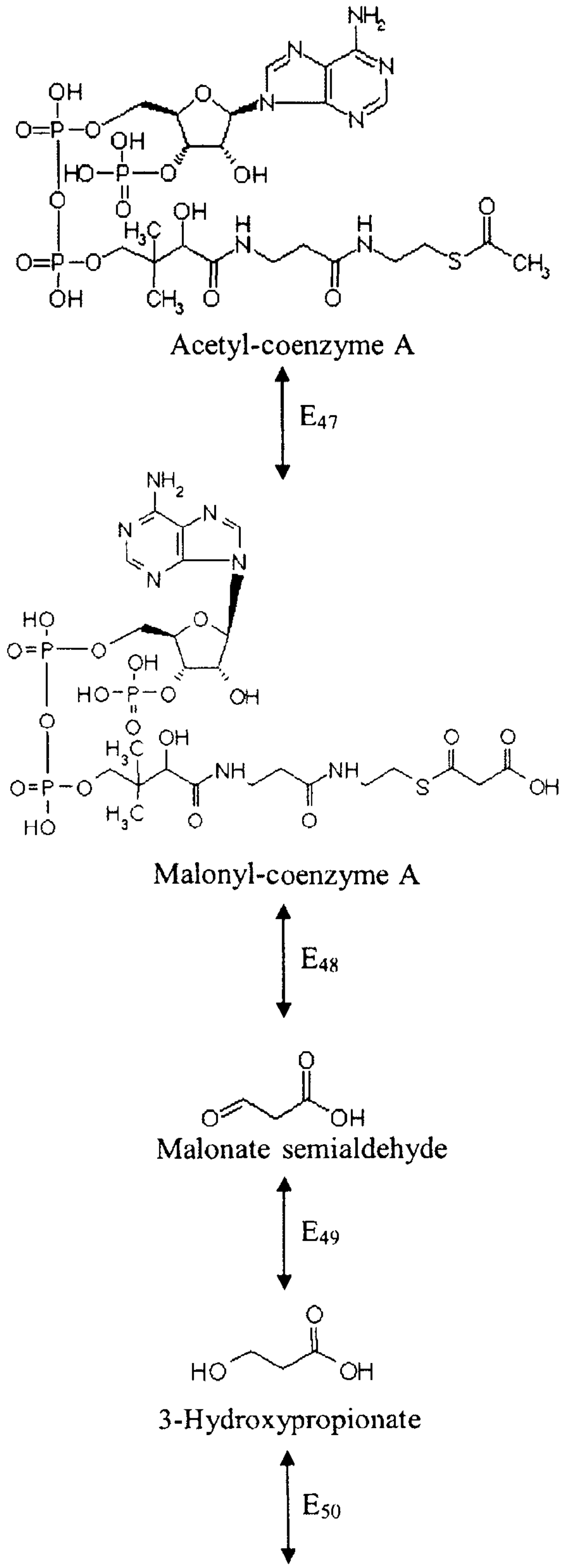
Figure 12:
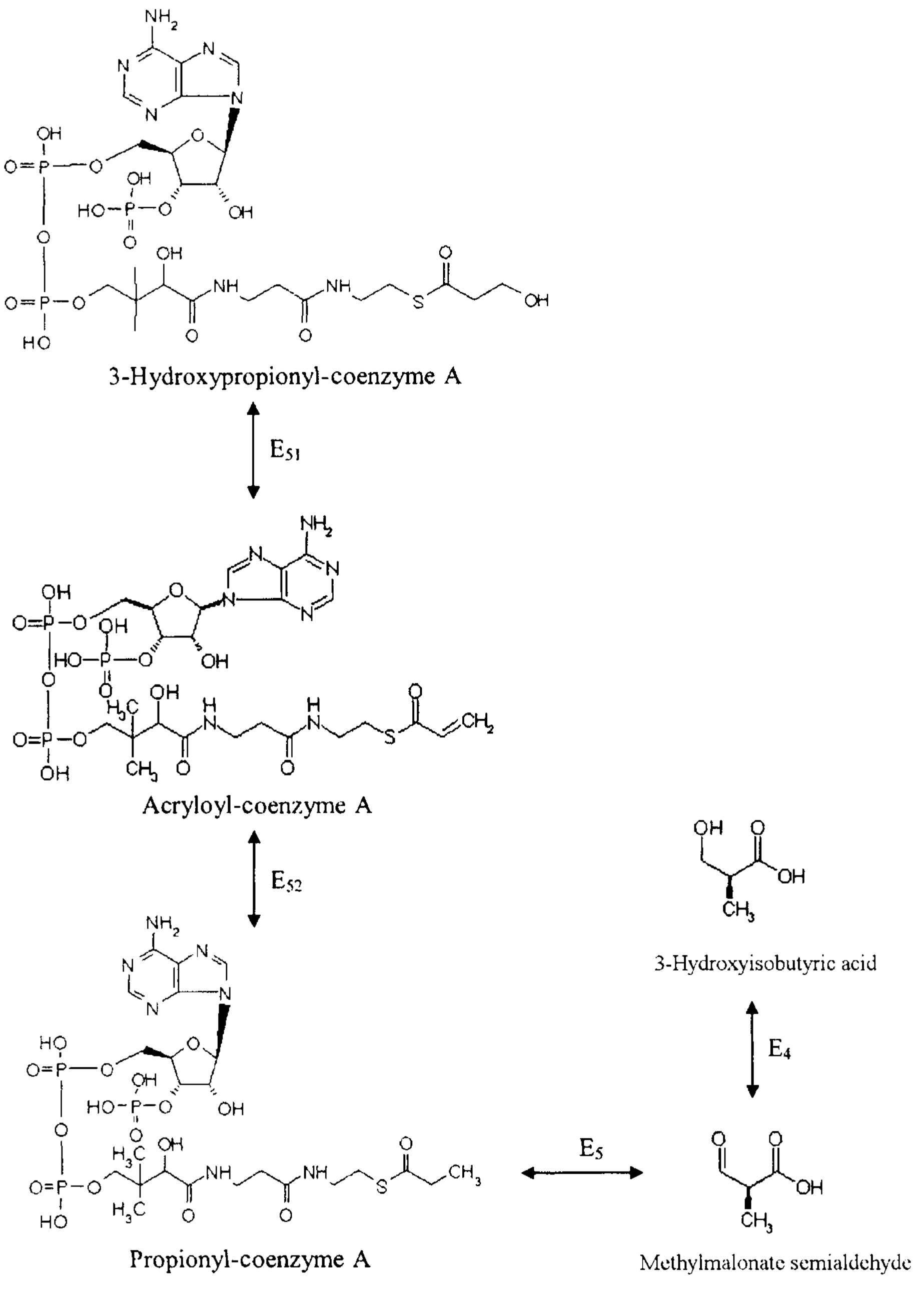
Figure 13:
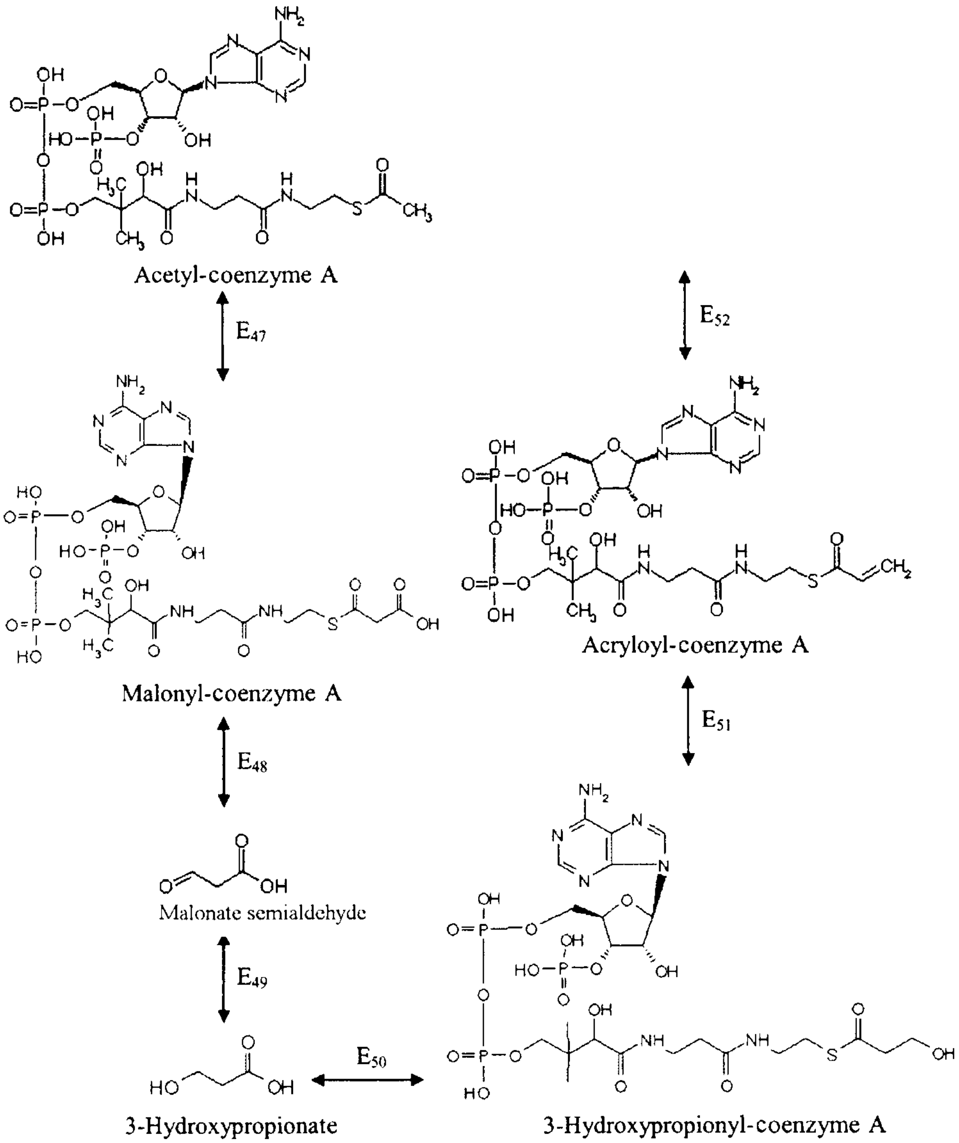
Figure 14:
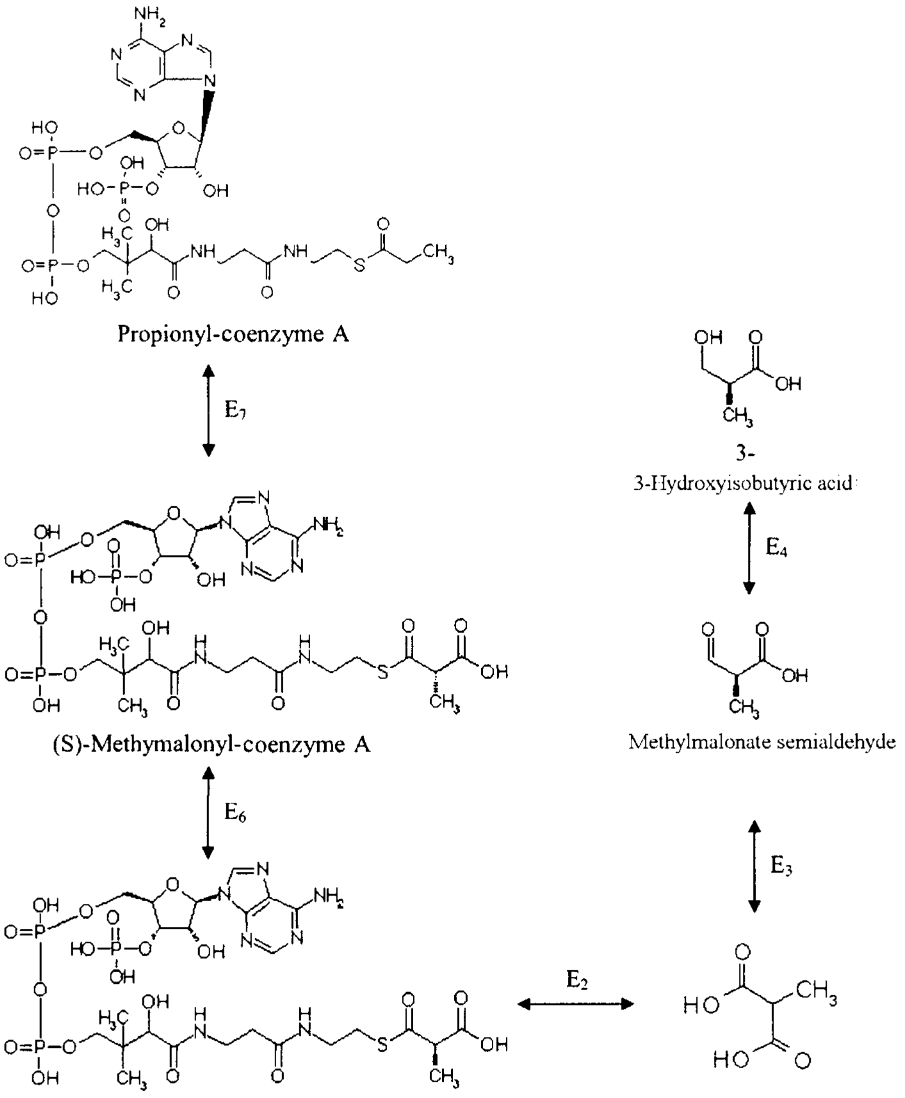
Figure 15:
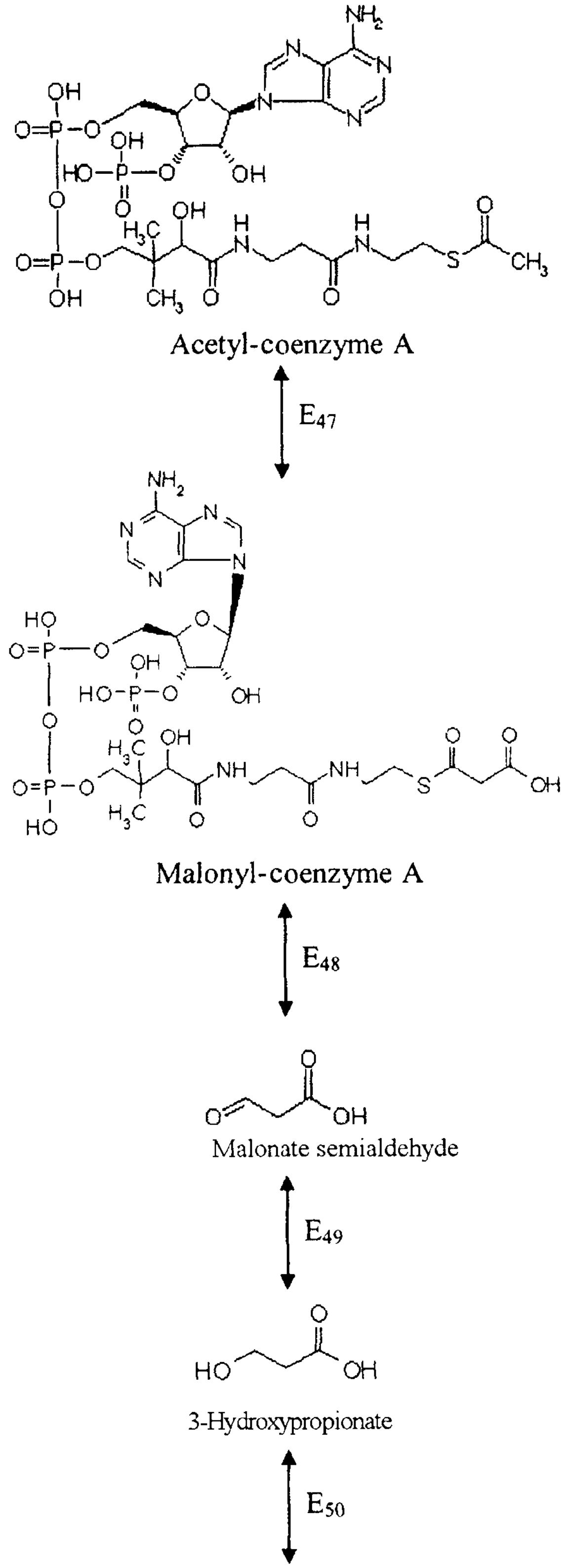
Figure 16:
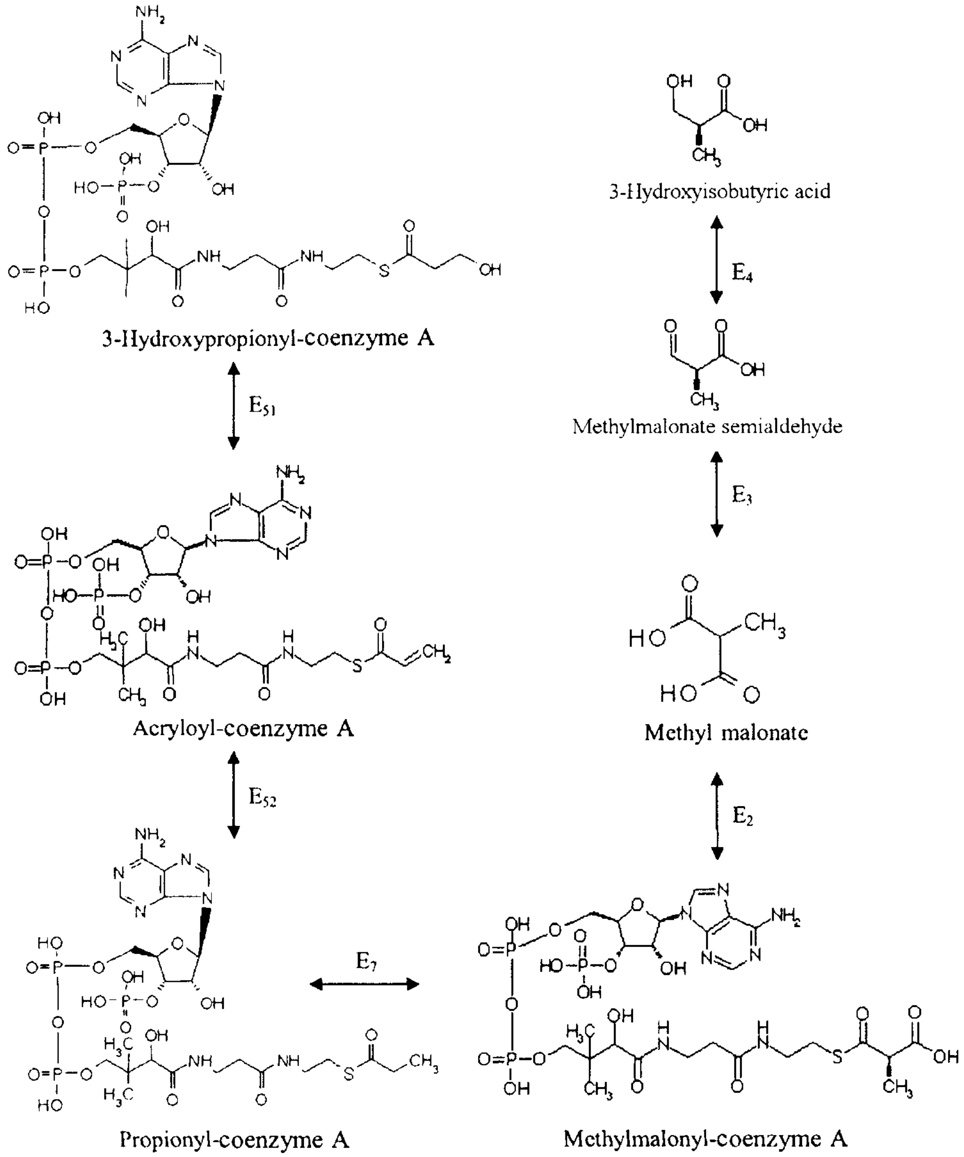
Figure 17:
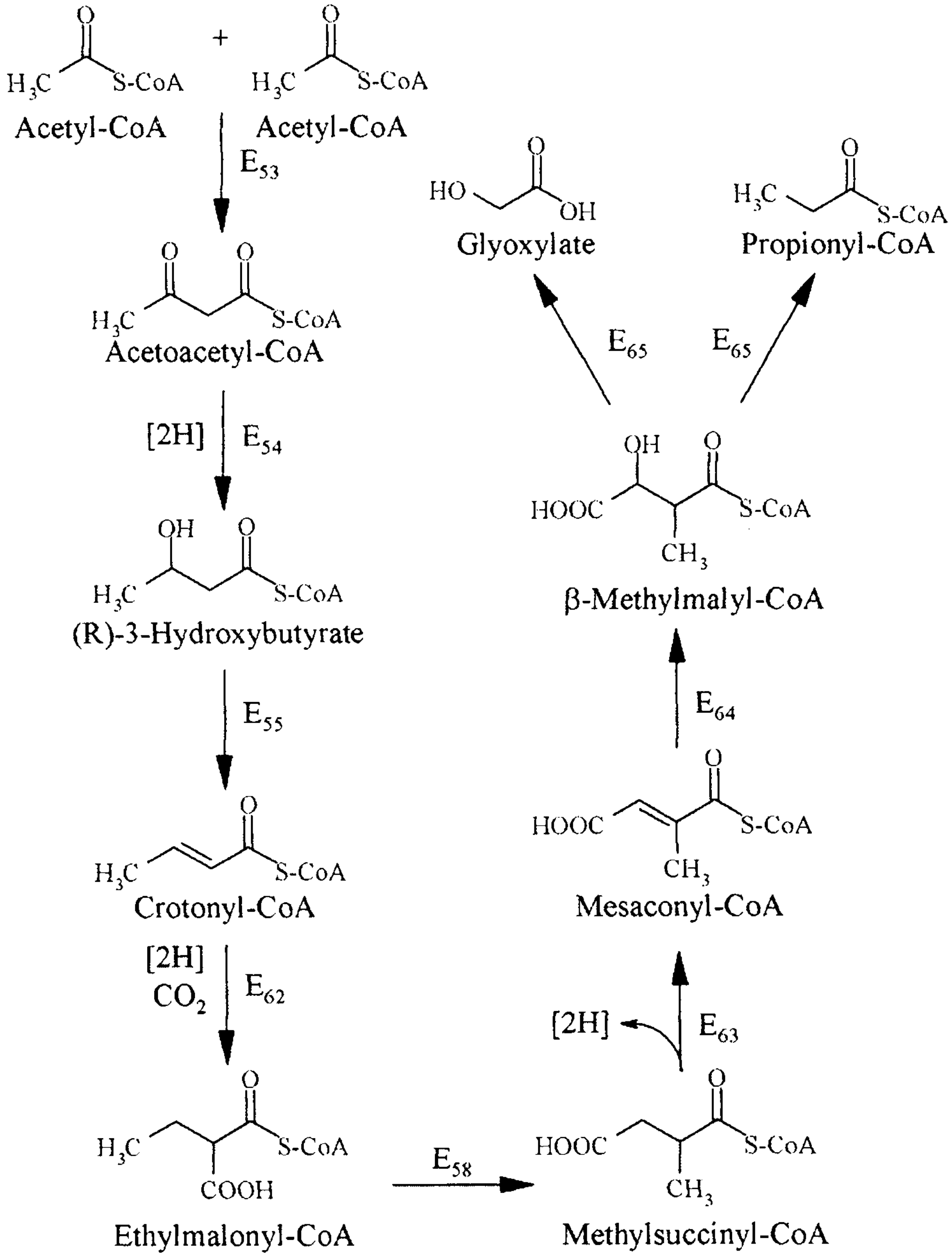
Figure 18:
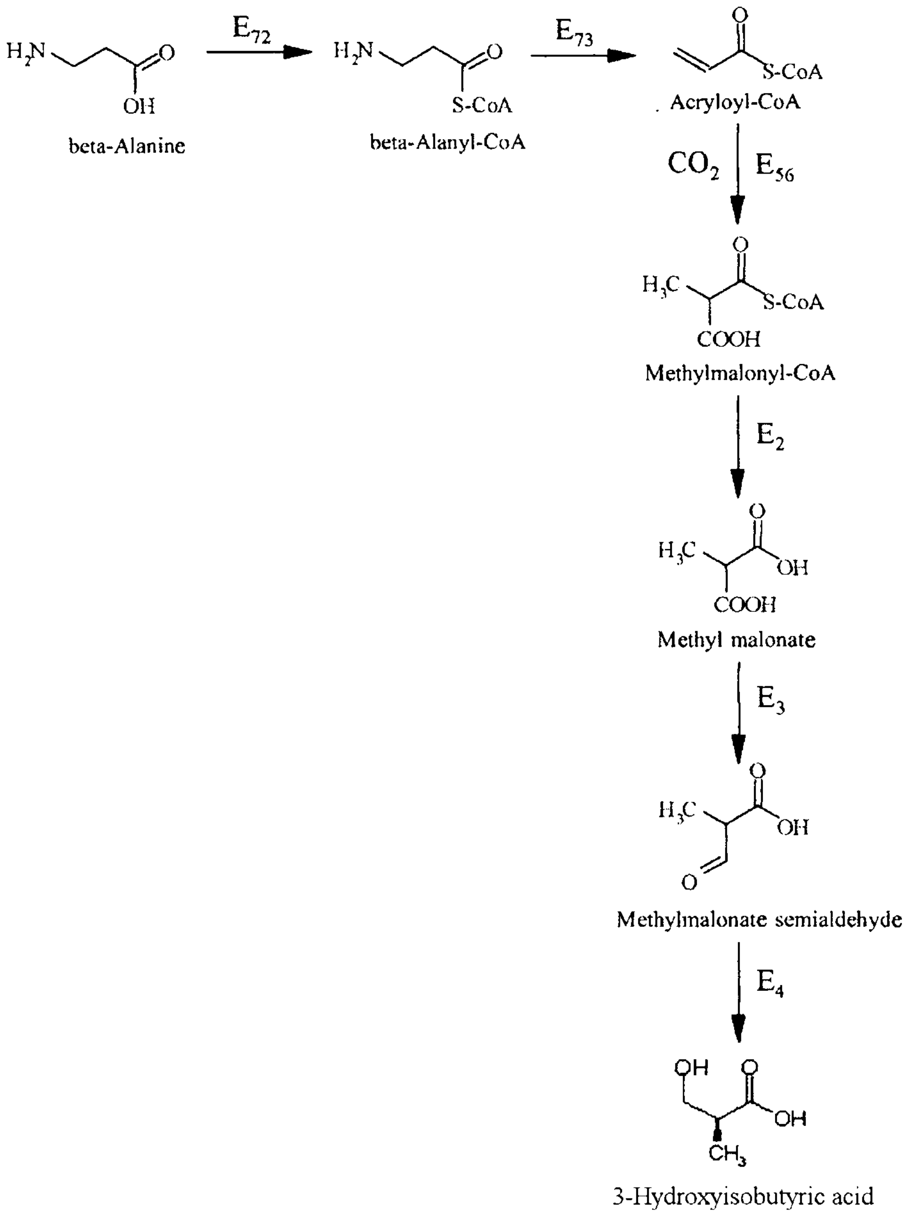
Figure 19:
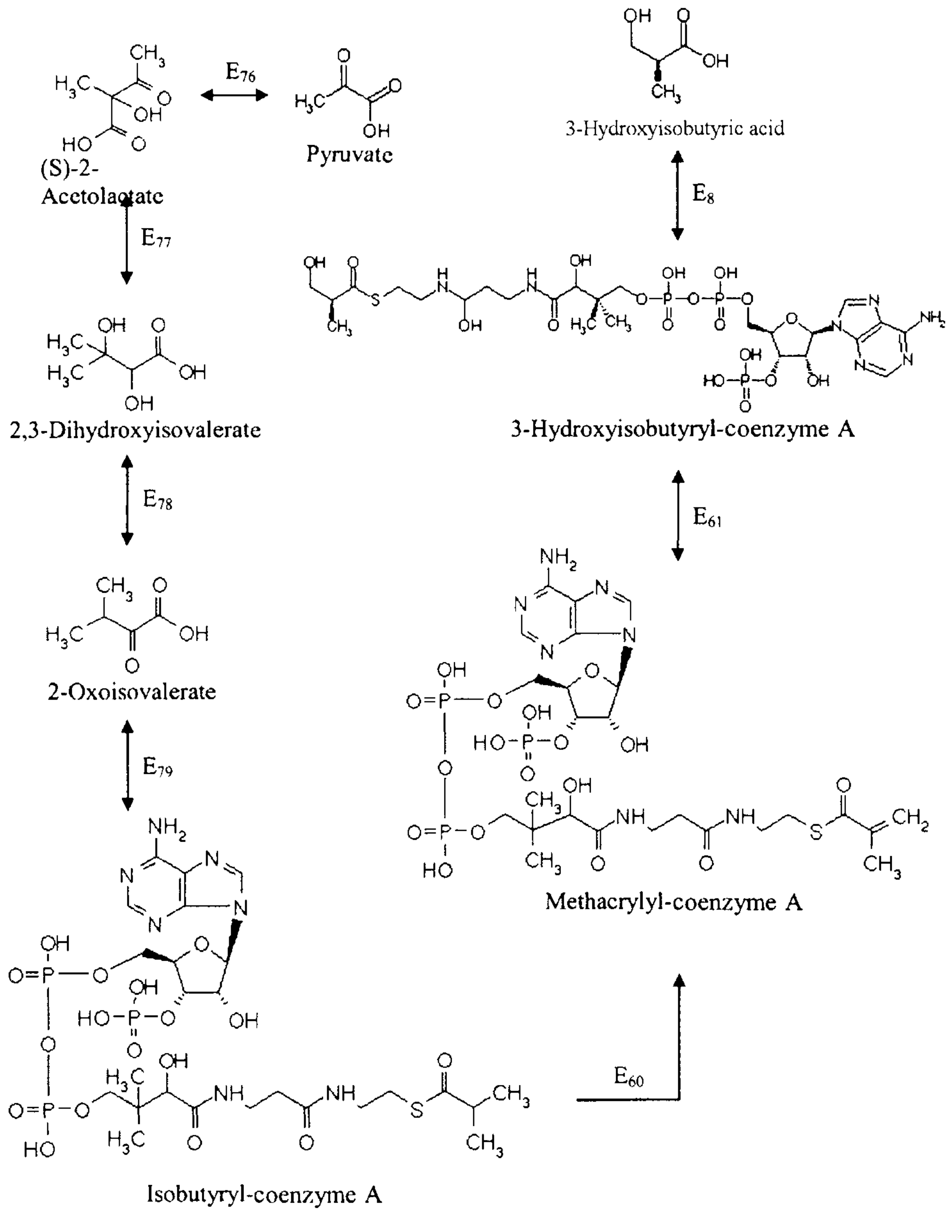
Figure 20:
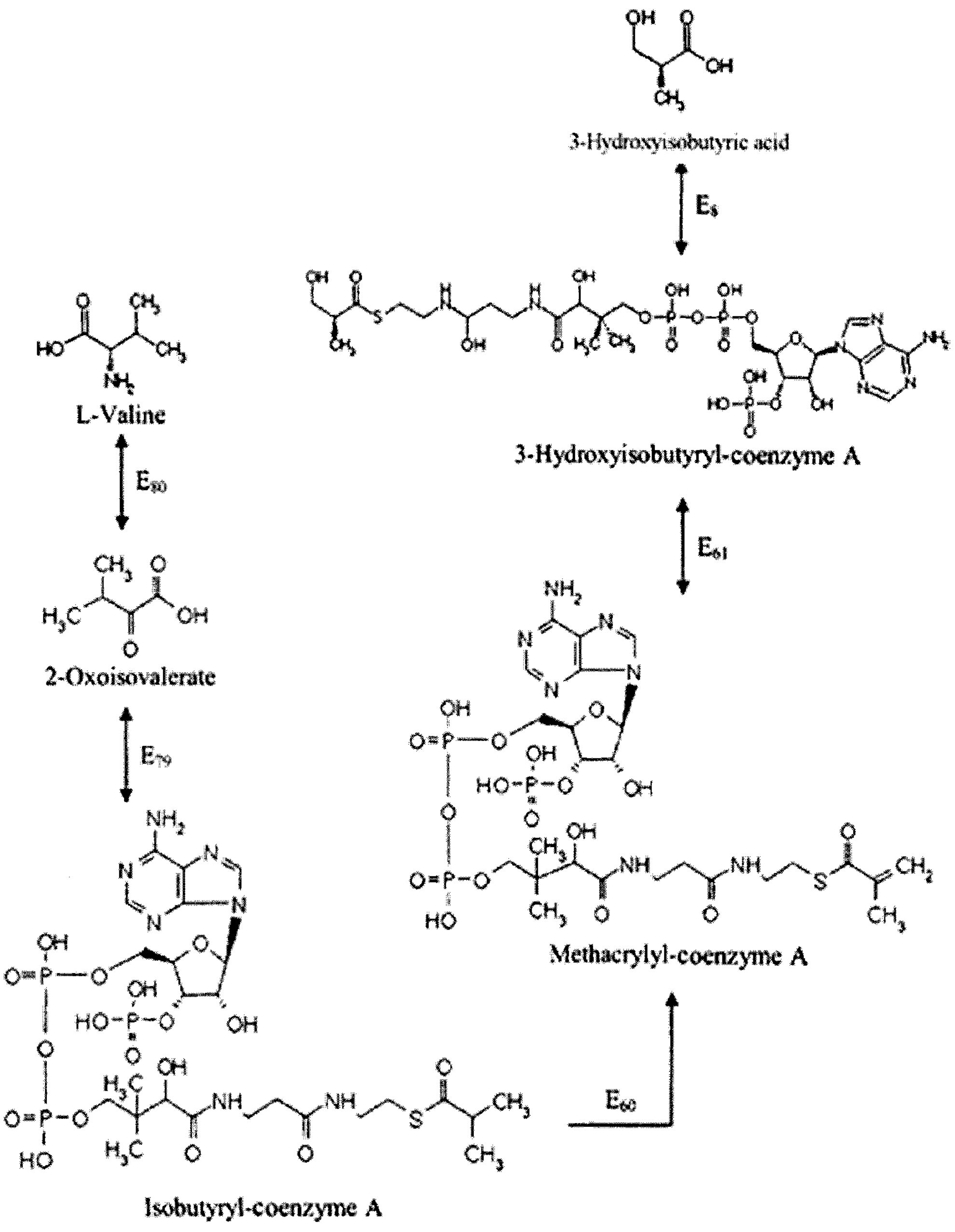

The present invention is now illustrated in Example 1 with reference to a recombinant cell which is capable of producing 3-hydroxyisobutyric acid via 3-hydroxyisobutyryl-coenzyme A as precursor and isobutyryl-coenzyme A as intermediate, starting from L-valine as carbon source. In accordance with the invention, this cell may be used for the production of methacrylic acid. To this end, the enzymes EC 2.6.1.42 and EC 1.2.4.4 (in each case from *Pseudomonas aeruginosa*) and a cluster comprising the three enzymes EC 1.3.99.12, EC 4.2.1.17 and EC 3.1.2.4 (from *Acinetobacter calcoaceticus*) were overexpressed in *E. coli* BL21 (DE3).

Here, the enzyme EC 1.2.4.4 is encoded by a gene with the DNA sequence as shown in SEQ ID No 07 and 08 (α and β subunit), while the enzyme EC 2.6.1.42 is encoded by a gene with the DNA sequence as shown in SEQ ID No 09. The enzyme EC 1.3.99.12 is encoded by a gene with the DNA sequence with the SEQ ID No 10, the enzyme EC 4.2.1.17 by a gene with the DNA sequence as shown in SEQ ID No 11, and the enzyme EC 3.1.2.4 by a gene with the DNA sequence as shown in SEQ ID No 12.

1. Organisms, Plasmids and Oligonucleotides

The following bacterial strains, vectors, genomic DNA and oligonucleotides were used for preparing this recombinant cell:

TABLE 1

| Bacterial strains used | |
|---|---|
| Strain | Reference (manufacturer) |
| *E. coli* DH5 | NEB |
| *E. coli* BL21 (DE3) | Invitrogen |

TABLE 2

| Vectors used | |
|---|---|
| Vector | Reference (manufacturer) |
| pCDFDuet-1 | Novagen |
| pET101/D-TOPO | Invitrogen |
| pCR2.1-TOPO | Invitrogen |

TABLE 3

| Genomic DNA used Strain |
|---|
| *Pseudomonas aeruginosa* PAO1 |
| *Acinetobacter calcoaceticus* ADP1 |

TABLE 4

| Oligonucleotides used | |
|---|---|
| Name | Sequence |
| Aca_VClus_fw | 5'-ATGCAATTTAATGAAGAACAGCTATTAATTC-3' (SEQ ID No. 13) |
| Aca_VClus_rev | 5'-CAGTCTGAAATGACTAACCTAATTGGC-3' (SEQ ID No. 14) |
| Pae_26142_fw | 5'-ACGGAATTCTGAAGGAGCTGGCAACTATG-3' (SEQ ID No. 15) |
| Pae_26142_rev | 5'-TTGTCGACTTACTTGACCAGGGTACGCC-3' (SEQ ID No. 16) |
| Pae_1244_fw | 5'-ACAGATCTGGAGGCCTGTCATGAGTGATTAC-3' (SEQ ID No. 17) |
| Pae_1244_rev | 5'-ATGGGTACCCATTCAGACCTCCATC-3' (SEQ ID No. 18) |

2. Amplification of the PCR Fragments 1.2.4.4 (2313 kb) and 2.6.1.42 (958 bp)

First, the fragments of 1.2.4.4 and 2.6.1.42 were amplified by means of PCR starting from the total DNA from *Pseudomonas aeroginosa*, using the primers as shown in SEQ ID No 15 to SEQ ID No 18, which are detailed in Table 4.

3. Digestion of the Vector pCDF-Duet-1 and of the PCR Fragment 2.6.1.42 (958 bp)

The vector pCDFDuet-1 (featuring a streptomycin-/spectinomycin resistance) is cleaved by means of EcoRI/SalI, as is the PCR fragment 2.6.1.42, and the restrictions thus obtained are ligated overnight with T4 ligase. This gives rise to the vector pCDFDuet::2.6.1.42.

4. Cloning of the PCR Fragments into the Vector pCR2.1-TOPO

The preparation of a cloning vector comprising the fragment 2.6.1.42 or the fragment 1.2.4.4, using the vector pCR2.1-TOPO, was performed as specified in the manufacturer's instructions. *E. coli* DH5a cells were transformed with the resulting cloning vectors pCR2.1-TOPO::1.2.4.4 and pCR2.1-TOPO::2.6.1.42. Since the pCR2.1-TOPO vectors feature a kanamycin resistance and an ampicillin resistance, the transformants were plated onto 2 AXI and KXI plates (20 and 40 μl). The plasmids of the resulting clones were isolated and digested:

| | |
|---|---|
| pCR2.1-TOPO::1.2.4.4 fragment size 2313 bp | BglII + KpnI |
| pCR2.1-TOPO::2.6.1.42 fragment size 958 bp | EcoRI + SalI |

Each of the fragments was eluted from the gel and purified with the QIAquick kit from Qiagen (following instructions).

5. Preparation of the Vector pCDFDuet:2.6.1.42-1.2.4.4

The vector pCDFDuet::2.6.1.42 and the vector pCR2.1-TOPO::1.2.4.4 are digested with BglII/KpnI.

This is followed by the ligation of pCDFDuet::2.6.1.42 (BglII/KpnI) with pCR2.1-TOPO::1.2.4.4, giving rise to the vector pCDFDuet::2.6.1.42-1.2.4.4. Again, *E. coli* DH5a cells were transformed by means of this cloning vector. The plasmids were isolated. The plasmid pCDFDuet::2.6.1.42-1.2.4.4 features the DNA sequence as shown in SEQ ID No 19.

6. Cloning the Valine Cluster from *Acinetobacter* Calcoaceticus (V-Clus$_{Aca}$)

Strain ATCC 33304 *Acinetobacter calcoaceticus* was cultured for the isolation of total DNA (HH agar or medium). Total DNA was isolated by means of the DNEasy kit from Qiagen (L1 and L2) and by a method comprising the method steps i) centrifugation of 1 ml of culture, ii) addition of 200 μl of $H_2O$ to the pellet, iii) heating for 10 min at 95° C., iv) centrifugation (10 min, 13 000 rpm), and v) removing the supernatant for a PCR.

To amplify the valine cluster from *A. calcoaceticus*, a PCR was carried out using the primers as shown in SEQ ID No 13 and SEQ ID No 14, which have been detailed in Table 4 (following the manufacturer's instructions using the polymerases Pfu and Taq, respectively).

The PCR products were purified and, following the instructions, ligated to the plasmid pET101/D-TOPO and transferred into *E. coli* DH5α. This gives rise to the plasmid pET101/D-TOPO::V-Cluster$_{Aca}$. Plasmid pET101/D-TOPO::V-Cluster$_{Aca}$ features the DNA sequence as shown in SEQ ID No 20.

7. Preparation of a Recombinant Cell which is Capable of Forming 3-Hydroxyisobutyric Acid from L-Valine

*E. coli* BL21 (DE3) was transformed with the plasmids pET101/D-TOPO::V-Cluster$_{Aca}$ and pCDF-Duet::2.6.1.42-1.2.4.4 (plated onto LB spec./amp medium). The resulting cells were capable of converting, in a nutrient medium comprising L-valine, the L-valine into 3-hydroxyisobutyric acid. In contrast, the wild type of the cells (*E. coli* BL21 (DE3)) was not capable of forming detectable amounts of 3-hydroxyisobutyric acid in such a nutrient medium.

Example 2

In this example, a DNA encoding a gene is isolated and the gene is overexpressed in *E. coli*. The DNA encodes an enzyme which has both the activity of the enzyme $E_2$ and that of the enzyme $E_3$.

1. Culturing and Harvesting *Sulfolobus tokodaii*

*Sulfolobus tokodaii* was grown in a small culture volume (40-200 ml) at 75° C. and a pH of 3.0, with shaking (150 rpm). The growth was monitored photometrically via measuring the optical density at 578 nm ($OD_{578\ nm}$). A modified *Sulfolobus* medium was used (modified as described by Brock et al., *Archives of Microbiology* 84, pages 54-68, 1972; Suzuki et al., *Extremophiles*, 6, pages 39-44, 2002). The energy and carbohydrate source used were yeast extract, casamino acids and glucose. The medium consisted of the following components: basal medium, glucose stock solution, iron stock solution and trace element stock solution. At an $OD_{578\ nm}$ of 0.3-0.5 (exponential phase), the cells were harvested. The centrifugation was carried out in a Sorvall centrifuge (SS34 rotor) for 15 min at 9000 rpm. The cell pellet was employed directly for the DNA extraction.

Basal medium. $KH_2PO_4$ (0.28 g/l), $(NH_4)_2SO_4$ (1.3 g/l), $MgSO_4 \times 7H_2O$ (0.25 g/l), $CaCl_2 \times 6H_2O$ (0.07 g/l), yeast extract (1 g/l) and casamino acids (1 g/l). Before autoclaving, the pH was brought to 3.0 using $H_2SO_4$.

Glucose stock solution (100×). Glucose (100 g/l).

The solution was filter-sterilized.

Iron stock solution (1000×). $FeCl_3 \times 6H_2O$ (20 g/l). The solution was filter-sterilized.

Trace element stock solution (1000×). $MnCl_2 \times 4H_2O$ (1.8 g/l), $Na_2B_4O_7 \times 10H_2O$ (4.5 g/l), $ZnSO_4 \times 7H_2O$ (220 mg/l), $CuCl_2 \times 2H_2O$ (50 mg/l), $Na_2MoO_4 \times 2H_2O$ (30 mg/l), $VOSO_4 \times 5H_2O$ (30 mg/l), $CoCl_2 \times 6H_2O$ (8.4 mg/l). The individual components were dissolved in succession in distilled $H_2O$, the pH was brought to 3.0 using HCl, and the solution was filter-sterilized.

2. Isolation of Genomic DNA from *S. tokodaii*

Genomic DNA was isolated by the method of Murray and Thompson (*Nucleic Acid Research*, 8, pages 4321-4325, 1980). To this end, 10-50 mg (fresh weight) of freshly harvested cells are weighed into a 1.5 ml Eppendorf reaction vessel and resuspended in 570 ml of TE buffer (10 mM Tris/HCl (pH 8.0), 1 mM NaEDTA). 30 μl of a 10% (w/v) SDS solution (sodium dodecyl sulfate solution) and 3 μl of Proteinase K (20 μg/μl) were added and the mixture was incubated for 1 h at 52° C. Thereafter, 100 μl of 5 M NaCl solution and 80 μl of pre-warmed 10% (w/v) cetyltrimethylammonium bromide (CTAB) solution (10% (w/v) CTAB in 0.7 M NaCl) were added. After incubation for 10 min at 65° C., the complexes of CTAB, cell wall fragments and proteins were extracted with 780 μl of chloroform/iso-amyl alcohol (24:1 (v/v)) and spun down for 15 min at 14 000 rpm. The aqueous top phase was transferred into a fresh Eppendorf reaction vessel and the extraction was repeated. After the aqueous phase was free from pigments, it was covered with a layer of 400 μl of 100% isopropanol. By carefully mixing the two phases, the chromosomal DNA precipitated at the interface. Then, it was possible to fish out the DNA with a drawn-out Pasteur pipette and washed in 200 μl of 70% ethanol. After recentrifugation (5 min, 14 000 rpm), the supernatant was pipetted off and the DNA was dried for 2 h at room temperature and finally dissolved in 100 μl of TE buffer.

3. Amplification of the Malonyl-Coenzyme A Reductase Gene

The polymer chain reaction (PCR) (Mullis et al., Cold Spring Harbor Symp. Quant. Biol., 51, pages 263-273, 1986) was employed to amplify the malonyl-CoA reductase gene in a targeted fashion, from the genomic *Sulfolobus tokodaii* DNA obtained in Example 2. It was carried out in a thermocycler (Biometra, Göttingen).

A preparative PCR in which Pfu polymerase (Pfunds, Genaxxon) was used, was employed. The Pfu polymerase contains a 3'-5' exonuclease ("proofreading") function.

The following primers were used:

```
5'-ATTATCCCATGGGGAGAACATTAAAAGC-3'
("forward primer"; NcoI cleavage site is
underlined; SEQ ID No 21)
and

5'-CGGGATCCTTACTTTTCAATATATCC-3'
("reverse primer"; BamHI cleavage site is
underlined; SEQ ID No 22)
```

The reaction mixture detailed in Table 1 hereinbelow was employed for the PCR reactions. The PCR was carried out as a hot start PCR, i.e. the reaction mixture was incubated for 2 min at 95° C. before adding the Pfu polymerase. This was followed by 30 cycles of in each case 1 minute at 95° C., 1 minute at 45° C. and 5 minutes at 72° C., followed by a last step of 30 seconds at 45° C., 15 minutes at 72° C. and, finally, a pause at 6° C.

TABLE 1

| Standard reaction mixtures (50 μl) for proofreading PCR with Pfu polymerase | |
|---|---|
| Composition | μl/50 μl batch |
| 10 × Pfu PCR reaction buffer | 5 |
| dNTP mix (2 mM per nucleotide) | 5 |
| Forward primer (2 μM) | 12.5 |
| Reverse primer (2 μM) | 12.5 |
| Chromosomal DNA | 1 (10-50 ng) |
| Pfu polymerase (2.5 U/μl) | 2 |
| dd-$H_2O$ | 12 |

A gene fragment with a length of 1.1 kb was obtained.

4. Cloning the Malonyl-Coenzyme A Reductase Gene

To clone the malonyl-coenzyme A reductase gene from *Sulfolobus tokodaii*, the gene amplified in Example 3 was cloned unspecifically with the vector pCR T7/CT-Topo (Invitrogen, Karlsruhe), using the "pCR T7 Topo TA Expression Kit" (Invitrogen, Karlsruhe). This was done following the manufacturer's instructions.

To isolate the plasmid DNA, the plasmid DNA was prepared using the "QIAprep Spin Plasmid Miniprep Kit" from Qiagen (Hilden) following the manufacturer's instructions, starting from 5 ml overnight cultures of transformed *E. coli* TOP10F' cells.

5. Generation of an Expression Vector

To generate an expression vector comprising the malonyl-coenzyme A reductase gene, the isolated cloning vector obtained in Example 4 is subjected to restriction digestion with the restriction enzymes NcoI and BamHI. To this end, 25-27 μl of plasmid DNA (expression vector pTrc99A and pCR T7/CT-Topo vector, respectively, with the incorporated malonyl-coenzyme A reductase gene) are mixed thoroughly with 5 μl of a reaction buffer (10×) and 2-3 μl of restriction enzyme (10 U/μl; Fermentas, St. Leon-Rot). The reaction mixture was made up to 50 μl with distilled $H_2O$ and incubated for 5 h at the temperature specified by the manufacturer. An ethanol precipitation was carried out before further use. To this end, the DNA was mixed with 3 volumes of 100% ethanol and 0.1 volumes of 3 M sodium acetate buffer (pH 5.3) and incubated for 2 h or overnight at −80° C. After a centrifugation step (20 min, 14 000 rpm, 4° C., Eppendorf table-top centrifuge), the supernatant is removed carefully, and the DNA was washed with 3 volumes of 70% (v/v) ethanol. After 10 min incubation at room temperature, the mixture was recentrifuged (10 min, 14 000 rpm, 4° C., Eppendorf table-top centrifuge) and the supernatant was discarded. The DNA was then dried for 1 hour at room temperature and subsequently taken up in the desired volume of $H_2O$ or TE buffer (10 mM Tris/HCl (pH 8.0), 1 mM NaEDTA).

Then, alkaline phosphatase is used for removing the 5'-phosphate groups of the linearized double-stranded vector. In this manner, the cloning efficiency is increased since religation of the vector is prevented. Calf intestinal alkaline phosphatase was used for dephosphorylating the digested vector.

The dephosphorylation was carried out in the same buffer as the restriction digestion. 50 μl of restriction mixture were mixed with 1.5 μl of CIAP (Calf Intestine Alkaline Phosphatase (1U/μl; Fermentas, St. Leon-Rot) and the mixture was incubated for 30 min at 37° C. Before further use of the cleaved and dephosphorylated vector, an ethanol precipitation was carried out as described above.

T4 DNA ligase was used the ligation of the insert DNA with the expression vector, plasmid DNA and insert DNA being employed in a molar ratio of from 1:3-1:6.

Stock solutions:

Ligation buffer (10×): 0.5 M Tris/HCl, pH 7.6 100 mM $MgCl_2$ 0.5 mg/ml BSA filter-sterilized, storage at room temperature 5 mM ATP (adenosine triphosphate) Always make up freshly in sterile distilled $H_2O$ 50 mM DTE (dithioerythritol) Always make up freshly in ligation buffer The ligation mixtures had a volume of 50 μl. Plasmid DNA (2-10 μl), insert DNA (2-20 μl), 5 μl of ligation buffer with DTE (50 mM) and the corresponding amount of sterile distilled $H_2O$ were pipetted together, vortexed, spun down briefly and subsequently incubated for 5 min at 45° C. The mixture was cooled on ice. 5 μl of 5 mM ATP and 1.5 μl of T4 DNA ligase (1 U/μl; Fermentas; St. Leon-Rot) were added, and everything was mixed. Ligation was performed overnight at 16° C.

The ligation mixture was employed directly for transforming chemically competent cells.

6. Transformation of *E. Coli* Cells with the Expression Vector

A 5 ml overnight culture was grown starting from a single colony of *E. coli* Rosetta 2 cells. On the next morning, 50 ml of LB medium (Sambrook et al., "*Molecular Cloning: A Laboratory Manual*", Cold Spring Harbor Laboratory Press, Cold Spring Harbor, N.Y., 1989) were inoculated with 0.5-1.0 ml of this culture. After incubation for 1.5-2 h (37° C., shaking (180 rpm)), an $OD_{578\ nm}$ of 0.6 was reached. The cells were cooled on ice for 10 min and subsequently spun down for 5 min at 5000 rpm and 4° C. (GSA rotor, Sorvall centrifuge). The supernatant was discarded and the cell pellet was resuspended in 2.7 ml of cold 0.1 M $CaCl_2$ solution. After addition of 2.3 ml of sterile 50% (v/v) glycerol, the cell suspension was divided into portions (in each case 300 μl) in 1.5-ml Eppendorf reaction vessels. The competent cells were immediately frozen in liquid nitrogen and subsequently stored at −80° C.

To transform the cells, an aliquot of the chemically competent cells (300 μl) was defrosted on ice and treated with 25 μl of a ligation mixture. Everything was mixed carefully and incubated for 30 min on ice. After a heat shock (42° C., 1 min) the mixture was reincubated on ice for 5 min. Thereafter, 800 μl of LB medium (Sambrook et al., 1989) were added, and the cells were shaken for 1 h at 37° C. (Thermomixer, Eppendorf 5436). The mixture was concentrated and finally streaked onto LB medium. To this end, the mixture was spun down for 1 min at 10 000 rpm, 750 μm of the supernatant were discarded, and the cell pellet was resuspended. 50 μl, 100 μl and 200 μl of this concentrated mixture were streaked onto LB plates (Sambrook et al., 1989) supplemented with 100 μg/ml ampicillin and incubated overnight in the incubator at 37° C. The plates were washed with 1 ml LB medium. This cell suspension was used for subsequently inoculating 150 ml LB medium (supplemented with 100 μg/ml ampicillin) in 500 ml Erlenmeyer flasks with baffles. The cultures grew at 37° C. and 180 rpm. Overexpression was performed by inducing the promoter in pTrc99A by adding 0.5 M IPTG (isopropyl-β-D-thiogalactopyranoside) at an $OD_{578\ nm}$ of 0.6. The induced cultures were incubated for 3 h under the abovementioned conditions and subsequently harvested at an $OD_{578\ nm}$=2.7.

7. Detection of the Enzymatic Activity

The *E. coli* strain obtained in Example 6 was disrupted by means of a cell mill. The disrupted cells were heated for 15 min at 85° C. During this heat precipitation, nonheat resistant enzymes coagulate and are precipitated. Since the target protein is heat resistant, it is retained in the supernatant. To measure the malonyl-coenzyme A reductase activity, the supernatant was diluted 1:50 in TM buffer (50 mM Tris/Cl, 1 mM $MgCl_2$, pH 8.1). 30 µl of the diluted or undiluted (for detecting the methylmalonyl-coenzyme A reductase activity) supernatant were pipetted to 500 µl of HIPS buffer (100 mM HEPES/NaOH, 5 mM $MgCl_2$, 1 mM dithioerythritol, containing 0.5 mM NADPH).

In a first batch, the reaction was started by adding malonyl-coenzyme A, the final concentration being 0.5 mM. The drop in the NADPH absorption at 365 nm was determined. The enzyme activity determined was 15.5 µmol/min/mg protein (15.5 U/mg).

In a second batch, the reaction was started by adding methylmalonyl-coenzyme A (from Fluka, Article No.: 67767), the final concentration being 2.0 mM. The drop in the NADPH absorption at 365 nm was determined. The enzyme activity determined was 0.24 µmol/min/mg protein (0.24 U/mg).

It can be seen from these results that the polypeptide which codes for the DNA sequence with the SEQ ID No 03 catalyzes both the conversion of malonyl-CoA and of methylmalonyl-coenzyme A.

1 mol of NADPH was oxidized per mole of malonyl-CoA or methylmalonyl-Coa employed. From this it can be concluded that the enzymatic reaction leads to the corresponding semialdehyde.

Example 3

The present invention is furthermore illustrated in Example 3 on the basis of the production of methacrylic acid by a recombinant cell capable of producing 3-hydroxyisobutyric acid via methylmalonate semialdehyde as precursor, starting from glucose as carbon source. To this end, the enzymes methylmalonyl-coenzyme A mutase ($E_1$) and 3-hydroxyisobutyrate dehydrogenase ($E_4$), inter alia, were overexpressed in *C. glutamicum* ATCC13032.

1. Cloning of the Genes NCgl1470, NCgl1471 and NCgl1472 (Arginine/Ornithine Transport System ATPase, Methylmalonyl-Coenzyme A Mutase and Methylmalonyl-Coenzyme A Mutase, N-Terminal Domain/Subunit) in pEKEx2, Construction of pEKEx2MCM cgl DNA manipulation using standard methods as described in Sambrook, J. et al. (1989), "*Molecular Cloning: a laboratory manual*", 2nd ed., Cold Spring Harbor Laboratory Press, Cold Spring Harbor, N.Y. DNA amplifications were carried out using SAWADY Pwo-DNA polymerase (Peqlab Biotechnologie, Erlangen, Germany) or Platinum Pfx-DNA polymerase (Invitrogen, Karlsruhe, Germany). Unless stated otherwise, the polymerases were used according to the manufacturer's information. Oligonucleotides for PCR amplifications and introduction of restriction cleavage sites were obtained from MWG-Biotech (Ebersberg, Germany). Engineered strains were identified by colony PCR using *Taq Polymerase READYMIX* (Sigma, Taufkirchen, Germany), and plasmid preparations. DNA fragments were purified and isolated using the MinElute Gel Extraction Kit (Quiagen, Hilden, Germany) according to the manufacturer's information. Plasmid DNA was isolated by means of the Qiaprep spin Miniprep Kit (Quiagen, Hilden, Germany). All of the plasmids constructed were verified by restriction analysis and subsequent sequencing.

pEKEx2MCM_cgl was constructed using the pEKEx2 vector (Kleinertz et al., 1991 *Gene* 102:93), which allows cloned genes to be transcribed under the control of the isopropyl β-D-thiogalactopyranoside (IPTG)-inducible tac promoter and the lac repressor system (lacIq). The 5.2 kb large DNA fragment coding for the genes NCgl1470, NCgl1471 and NCgl1472 was amplified by means of the following oligonucleotides and *Corynebacterium glutamicum* ATCC13032 DNA as template:

```
pcg1859-57_vorwärts (SEQ ID No. 23):
5'-cggtcgacaaggagatatagataTGACTGATCTCACAAAGACTGC-3
and

pcg1857-59_rückwärts (SEQ ID No.24):
5'-cTTAGGCTTTGTCGAACGCCTCC-3'.
```

(Sequences complementary to the genomic sequence are indicated in capital letters).

Figure 21:
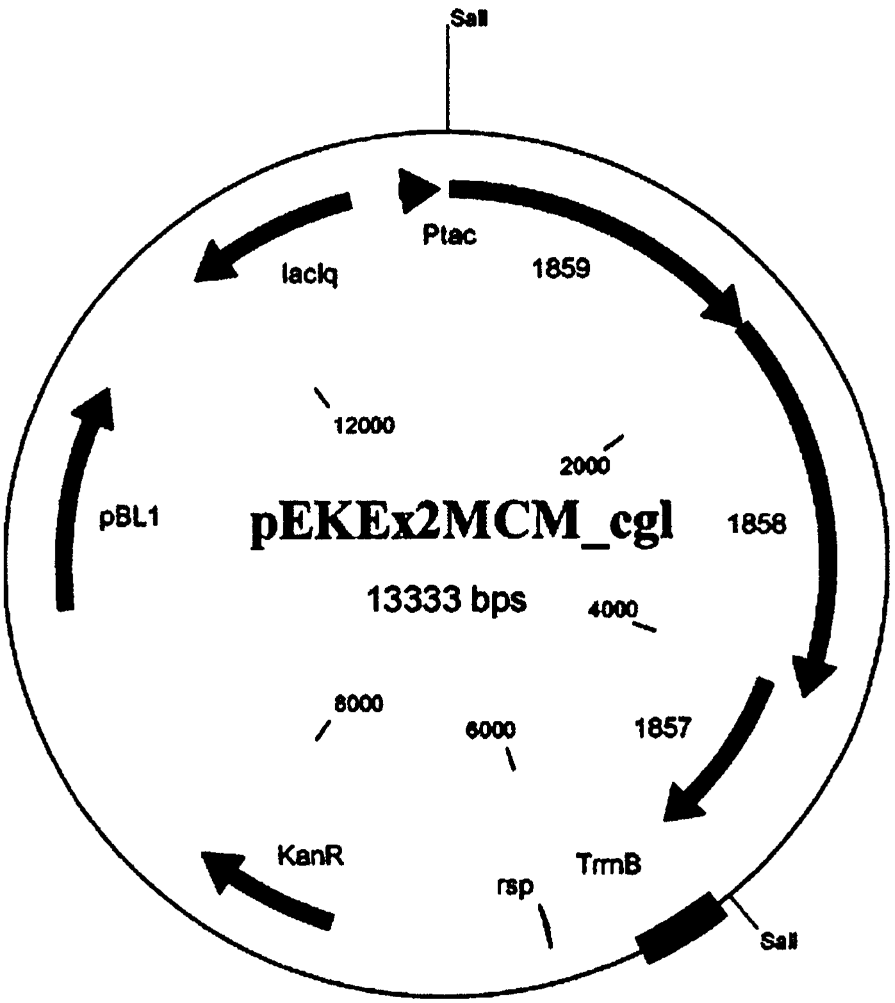
FIG. 21 shows the plasmid pEKEx2MCM of Example 3.

In addition, restriction cleavage sites (underlined) and a ribosome binding site (aaggag), 8 nucleotides upstream of the start codon, were introduced into the amplicons. In the process, the original start codon, TTG, was replaced with ATG). The PCR amplicon was phosphorylated using polynucleotide kinase (Roche, Basle, Switzerland) and cloned with blunt ends into the SmaI cleavage site of the pUC19 vector (Yanisch-Perron et al., 1985, Gene 33:103-19). The identity and correctness of the 5.2 kb insert were confirmed by sequencing. The 5.2 kb fragment was then isolated by way of a SalI fragment from the pUC19 derivative and ligated to the SalI cleavage site of the pEKEx2 vector. Plasmids having the correct orientation were selected on the basis of restriction digest, with one of these being referred to as pEKEx2MCM cgl. The plasmid obtained is shown in FIG. 21.

Figure 22:
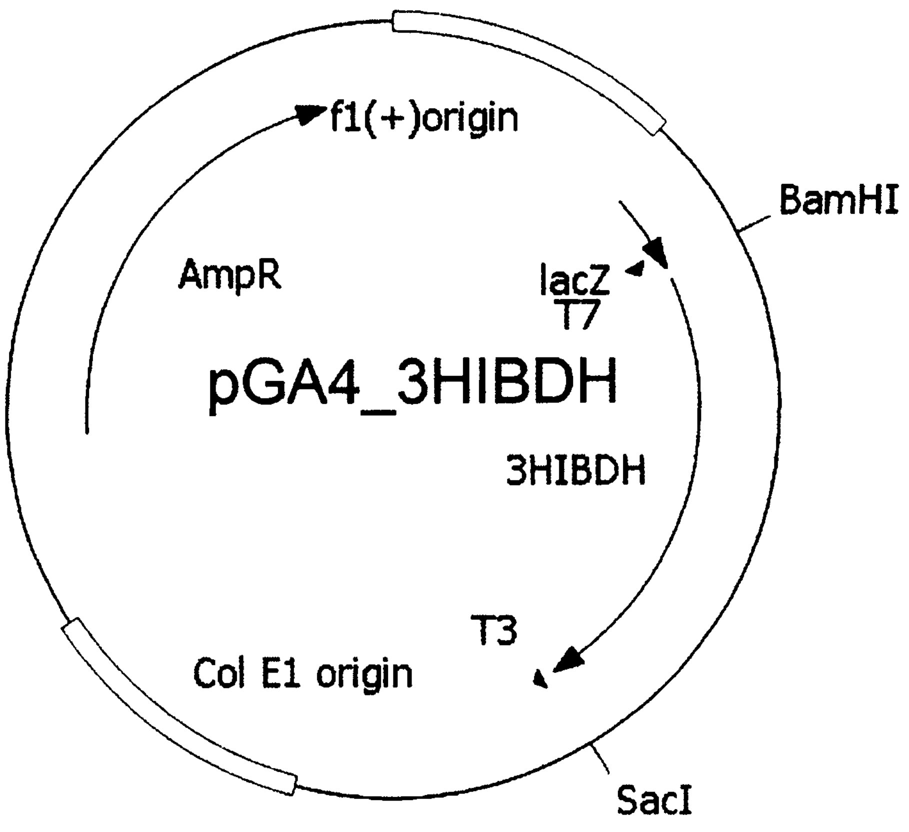
FIG. 22 shows the vector pGA4_3HIBDH of Example 3.
Figure 23:
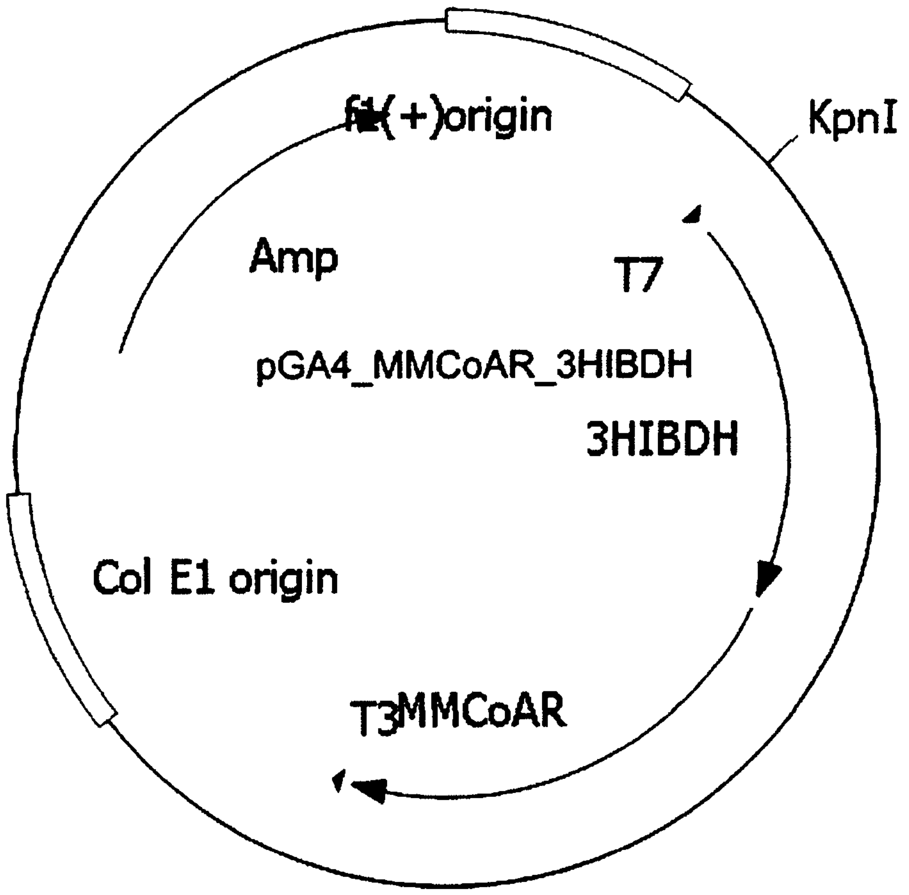
FIG. 23 shows the vector pGA5_MMCoAR_3HIBDH of Example 3.

2. Cloning of *Thermus thermophilus* 3-Hydroxyisobutyrate Dehydrogenase in pEKEx2, Construction of pEC-XT99A MMCoAR 3HIBDH The gene of *Thermus thermophilus* (TTHA0237) 3-hydroxyisobutyrate dehydrogenase (3HIBDH) was synthesized, taking into account the codon usage of *C. glutamicum*. The codon usage-optimized gene (SEQ ID No. 25) was synthesized into the vector pGA4 (pGA4_3HIBDH, FIG. 22). The pGA4_3HIBDH vector was digested by the endonucleases KpnI and Ecl136II and, as a result of this, the 3HIBDH gene was ligated into the vector pGA5_MMCoAR, a vector which already contains a sequence derived from *Sulfolobus tokodaii* methylmalonyl-coenzyme A mutase under the functional expression control of the T7 promoter and which had been linearized by the restriction enzymes BamHI (with subsequent filling-in reaction) and KpnI. The resulting vector, pGA5_MMCoAR_3HIBDH is depicted in FIG. 23.

Figure 24:
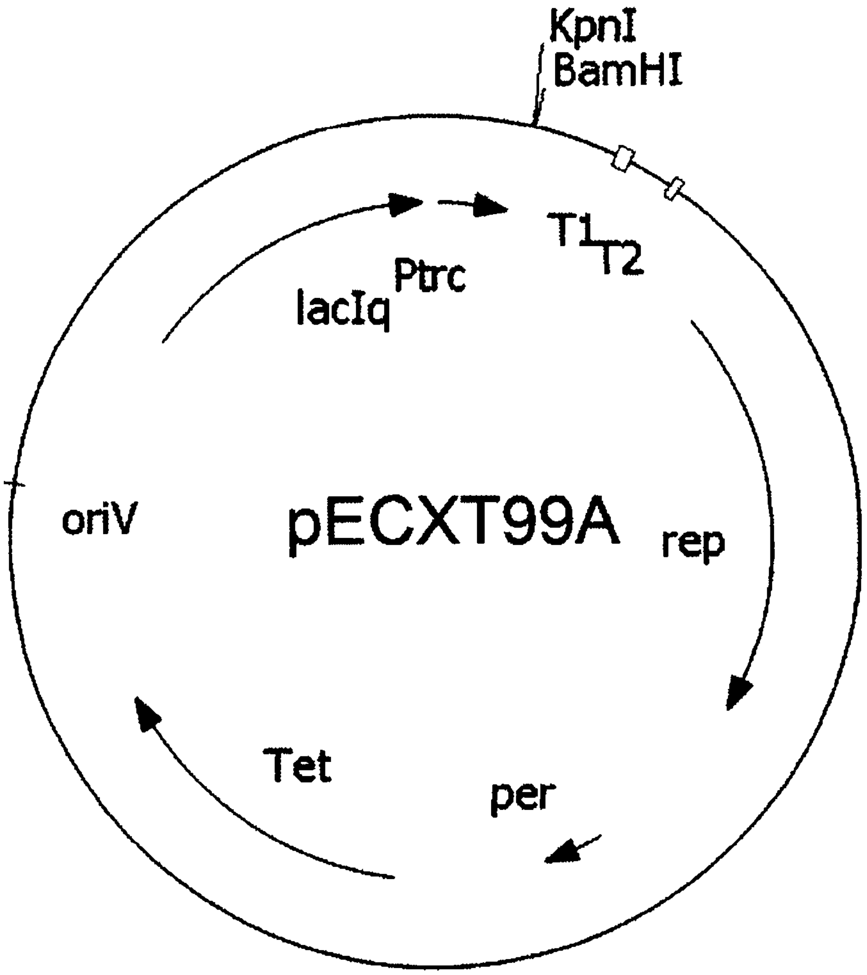
FIG. 24 shows the vector pECXT99A of Example 3.
Figure 25:
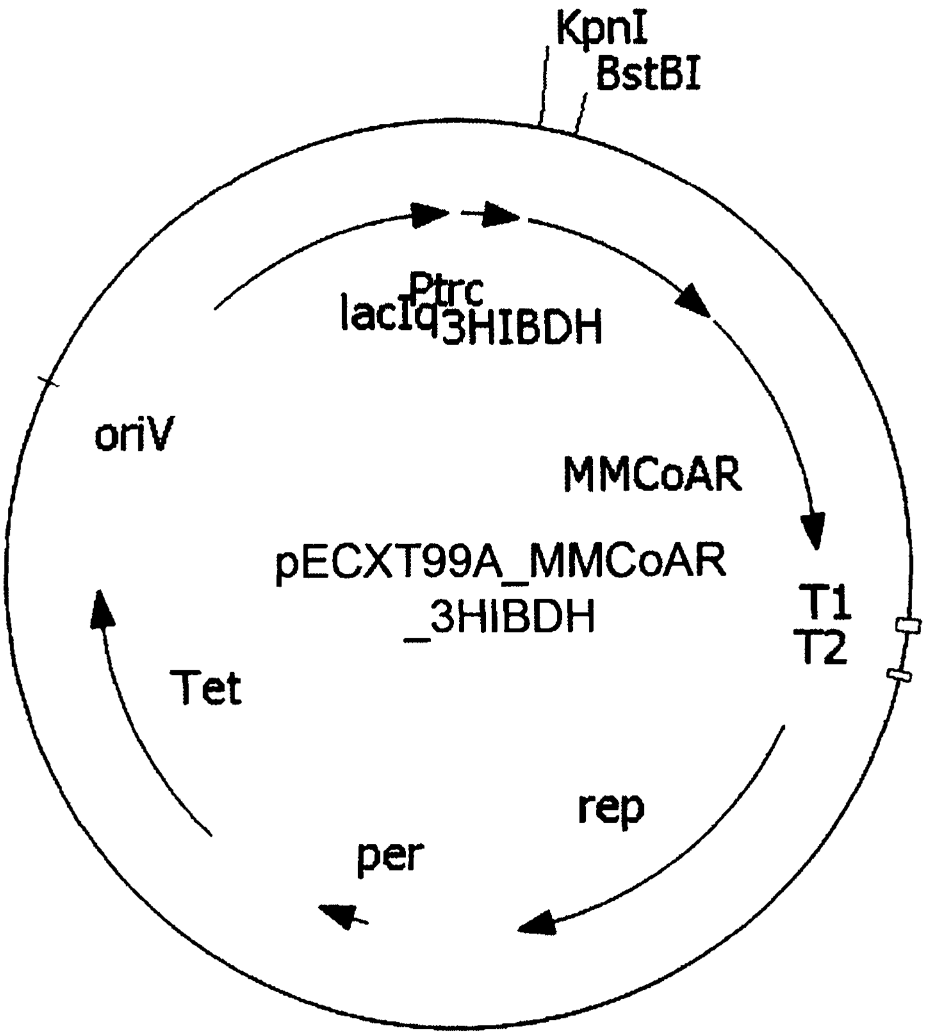
FIG. 25 shows the vector pECXT99A_MMCoAR__3HIBDH of Example 3.

The insert containing methylmalonyl-coenzyme A reductase and 3HIBDH was cloned into the target vector pECXT99A (accession number: AY219684, FIG. 24) which had been linearized by digestion with the restriction endonucleases BamHI (with subsequent filling-in reaction) and KpnI from the pGA5MMCoAR-_3HIBDH vector by digestion with KpnI and Ecl136II (resulting vector: pECXT99A_MMCoAR_3HIBDH, FIG. 25).

3. Preparation of *C. glutamicum* Cells Transformed with pEKEx3MCM cgl and pEC-XT99A 3HIBDH varIIMMCoAR Competent cells of *C. glutamicum* ATCC13032 were prepared as described in Tauch et al. (*Curr Microbiol.* 2002, 45:362-367). DNA of pEKEx2MCM_cgl and pEC-XT99A_3HIBDH_varIIMMCoAR was introduced by means of electroporation, and transformants were selected on brain heart agar from Merck (Darmstadt, Germany) which had been supplemented with 50 mg/l kanamycin and 5 mg/l tetracycline (Liebl et al. *FEMS Microbiol Lett.*, 1989, 53:299-303).

Plasmid DNA was isolated from transformants and characterized by means of restriction digest. In this manner *C. glutamicum* pEKEx2MCM_cgl/pEC-XT99A__3HIBDH_varIIMMCoAR was obtained.

4. Cultivation and Production of 3-Hydroxyisobutyric Acid

A single colony of *C. glutamicum* pEKEx2MCM_cgl/pEC-XT99A__3HIBDH_varIIMMCoAR was used for inoculation in 25 ml of complete medium (brain heart medium) containing 15 μg/l kanamycin and 5 μg/l tetracycline, and cultured at 30° C. and 200 rpm overnight. The wild type was grown without antibiotics as a control.

The cultures were removed by centrifugation (10 min, 4° C., 5292×g) and washed with saline (0.9% NaCl). The cells were resuspended in 25 ml (in 250 ml flasks) of GCXII medium containing antibiotics (15 μg/l kanamycin and 5 μg/l tetracycline). The plasmid-carrying strain was induced with 0.5 mM (12.5 μl of a 1 M stock solution) IPTG.

CGXII Minimal Medium (According to Keilhauer et al., J Bacteriol. 1993, 175:5595-5603):

20 g $NH_4)_2SO_4$
5 g urea
1 g $K_2HPO_4$
1 g $KH_2PO_4$
42 g MOPS
1 ml $MgSO_4 \times 7H_2O$ (25 g/100 ml, sterile-filtered)
1 ml $CaCl_2 \times 2H_2O$ (1.32 g/100 ml, sterile-filtered)

The salts were dissolved in approx. 800 ml of double-distilled water and the pH was adjusted to 7 with KOH. For this purpose, approx. 20-25 KOH pellets were added, followed by titration to pH 7 with 10 N KOH. Double-distilled water was then added to the media components to 900 ml, followed by autoclaving.

After autoclaving, 1 ml of trace salt solution was added.

Trace Salt Solution:

1 g $FeSO_4 \times 7H_2O$
1 g $MnSO_4 \times H_2O$
0.1 g $ZnSO_4 \times 7H_2O$
0.02 g $CuSO_4$
0.002 g $NiCl_2 \times 6H_2O$ The salts are dissolved in 100 ml of deionized $H_2O$ and acidified with HCl (pH paper, approx. pH 1). The solution is then sterile-filtered.

The medium was admixed with 100 ml of 50% strength glucose (final concentration 5%), with 80 ml of 50% strength glucose and 20 ml of sterile double-distilled water being added for a final concentration of 4%.

The medium was supplemented with 1 ml of biotin (20 mg/100 ml), 60 μg/l coenzyme B12 (after 7 h), 0.1 mM propionate (after 22 h) and trace salt solution.

Figure 26:
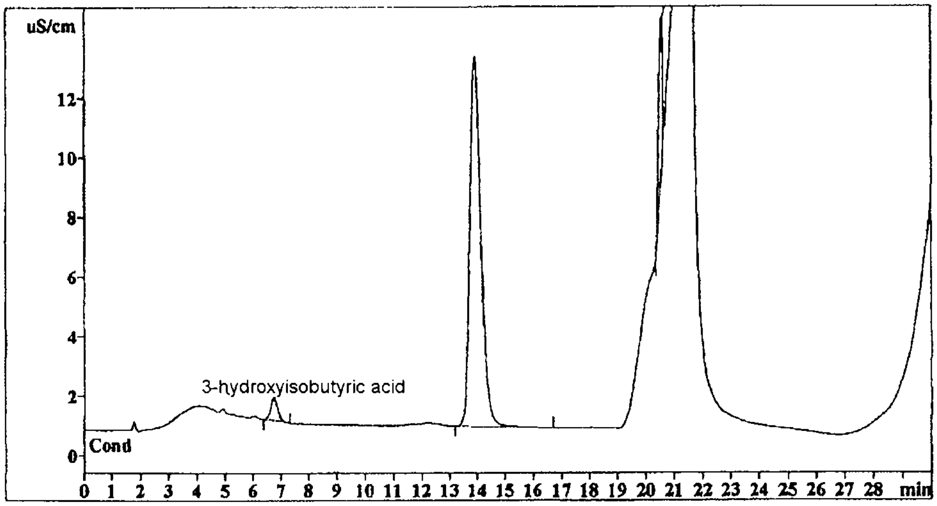
FIG. 26 shows detection by means of ion chromatography of production of 3-hydroxyisobutyric acid by the recombinant cells in Example 3.
Figure 27:
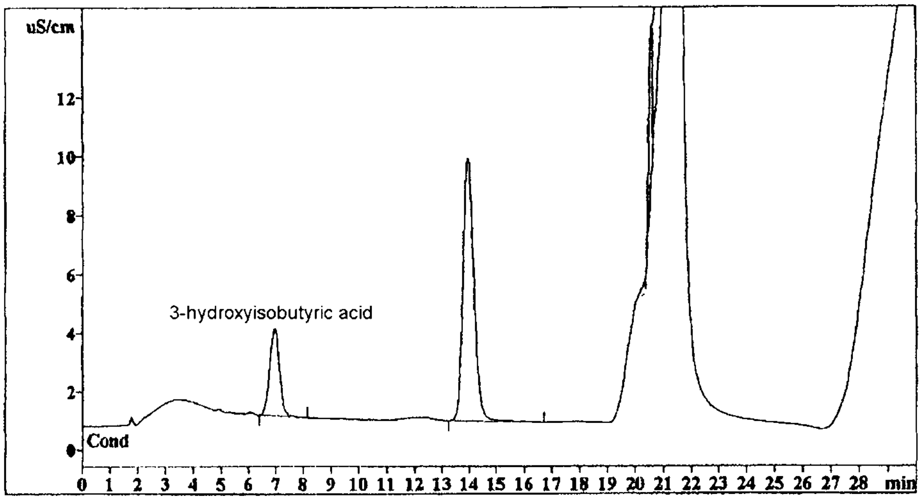
FIG. 27 shows the peak indicated in FIG. 26 being identified by means of ion chromatography as that of 3-hydroxyisobutyric acid.

After 27 h, 6 mg/l 3-hydroxyisobutyric acid were detected in the sample by ion chromatography (Metrohm Compact IC 761 with autosampler, mobile phase: 8 mM NaOH; column: Dionex AS15 4×250 mm+precolumn AG15 4×50 mm; column temperature: 25° C., flow: 1.4 ml/min, detector: conductivity; injection volume: 10 μl; run time: 30 min) (FIG. 26). The identity of 3-hydroxyisobutyric acid was confirmed by adding chemically pure 3-hydroxyisobutyric acid (30 mg/l) (FIG. 27).

5. Dehydration of 3-Hydroxyisobutyric Acid to Give Methacrylate 5 ml of a solution of 3-hydroxyisobutyric acid (0.2 g/l), produced according to Example 4 above, is admixed with NaOH (0.06 mg) with stirring. The solution is incubated with stirring and reflux condensation at 185-195° C. under vacuum (300 torr). A further 0.5 mg of 3-hydroxyisobutyric acid in 5 ml are added every hour over a period of 5 h. The solution contains 0.4 percent by weight p-methoxy-phenol in order to prevent methacrylate from polymerizing. The reaction is stopped after 24 h of incubation. Conversion of 3-hydroxyisobutyric acid to methacrylate is above 90%. Methacrylic acid is removed from the reaction mixture by distillation.

Example 4

The present invention is furthermore illustrated in Example 4 on the basis of the production of methacrylic acid by a recombinant *E. coli* cell which is capable of producing 3-hydroxyisobutyric acid via methylmalonate semialdehyde as precursor and via acryloyl-coenzyme A as intermediate.

To convert the carbon source glycerol to 3-hydroxy-isobutyric acid using recombinant *E. coli* cells, the genes of seven different enzymes were cloned into a number of expression plasmids. This involved the utilization of Duet vectors (Merck, Germany). These are a system of four expression vectors, all of which are compatible with one another and in addition have different antibiotic resistance markers.

1. In detail, the genes coding for the following enzymes were cloned into expression vectors for converting glycerol to 3-hydroxyisobutyric acid:
   a) *Klebsiella pneumoniae* glycerol dehydratase (EC 4.2.1.30) (GD). The enzyme catalyzed the adenosylcobalamine-dependent dehydration of glycerol to 3-HPA (3-hydroxypropionaldehyde). It consists of 3 subunits (GD-alpha, GD-beta and GD-gamma) which are encoded in *K. pneumoniae* by 3 genes (gldA, gldB and gldC) in a single operon.
   b) *K. pneumoniae* reactivating factor. Since adenosylcobalamine-dependent glycerol dehydratases are inactivated by glycerol, conversion of glycerol to 3-HPA additionally requires the activity of a reactivating factor. The reactivating factor for *K. pneumoniae* glycerol dehydratase is encoded by the genes gdrA and gdrB
   c) *E. coli* aldehyde dehydrogenase, AldH. To convert 3-HPA to 3-hydroxypropionic acid (3-HP), the *E. coli* aldH-gene was amplified.
   d) *Chloroflexus aurantiacus* propionyl-coenzyme A synthase (Pcs) (encoded by the pcs gene). Propionyl-coenzyme A synthase catalyzes the conversion of 3-HP to propionyl-coenzyme A. It is a tri-functional enzyme and includes three functional domains. The acyl-coenzyme A synthetase (ACS) domain catalyzes activation of 3-HP to 3-hydroxypropionyl-CoA. This is followed by dehydration to acrylyl-CoA, catalyzed by the enoyl-CoA hydratase (ECH) domain of Pcs. Finally, the enoyl-CoA reductase (ECR) domain of Pcs catalyzes the NADPH-dependent reduction of acrylyl-CoA to give propionyl-CoA. However, this reaction is irrelevant to the project described because the intermediate acrylyl-CoA is immediately further converted here by the next enzyme (crotonyl-CoA carboxylase/reductase, see below).
   e) Crotonyl-coenzyme A carboxylase/reductase (enzyme $E_{62}$) (Ccr) of *Rhodobacter sphaeroides* (encoded by the ccR gene). The main activity of Ccr is the reductive carboxylation of crotonyl-coenzyme A to give ethylmalonyl-CoA. However, the enzyme exhibits a broad substrate specificity and converts acrylyl-coenzyme A to methylmalonyl-coenzyme A very efficiently.
   f) *Sulfolobus tokodaii* malonyl-CoA reductase (Mcr, $E_2$ and $E_3$) (encoded by the mcr gene). Mcr preferentially catalyzes the NADPH-dependent reduction of malonyl-coenzyme A to malonate semialdehyde. However, it also exhibits a secondary activity with methylmalonyl-coenzyme A as substrate which is converted to methylmalonate semialdehyde.

g) *Thermus thermophilus* 3-hydroxyisobutyrate dehydrogenase ($E_4$) (3-HIB-DH) (encoded by the MmsB gene). This enzyme catalyzes the NADPH-dependent, reversible conversion of methyl-malonate semialdehyde to 3-hydroxyisobutyric acid (3-HIB).

2. The cloning strategy for heterologous overexpression of the above-described enzymes is described in detail below.

a) Construction of plasmid pACYCDuet-KpGDRF for overexpression of glycerol dehydratase reactivating factor (GDRF).

First, the genes gdrA (synonym: ORF4) and gdrB (synonym: ORF2b), which encode the two subunits of *K. pneumoniae* GDRF, were amplified by means of PCR. The template used was chromosomal DNA of the strain *K. pneumoniae* DSM2026.

gdrA was amplified using the following oligonucleotides:

```
orf4fw (SEQ ID No. 26):
5'-TGAAGATCCTAGGAGGTTTAAACATATGCCGTTAATAGCCGGGA
TTG-3')

orf4Salrv (SEQ ID No. 27):
5'-TATATAGTCGACTTAATTCGCCTGACCGGCCAG-3';
(SalI recognition sequence is underlined).
```

gdrB was amplified using the following oligonucleotides

```
orf2bPcifw (SEQ ID No. 28):
5'-TATATAACATGTCGCTTTCACCGCCAGGC-3'
(PciI recognition sequence is underlined)

orf2brv (SEQ ID No. 29):
5'-CATATGTTTAAACCTCCTAGGATCTTCAGTTTCTCTCACTTAACGG
GCAGG-3')
```

The PCR products obtained were then fused to one another by crossover PCR.

To this end, the following oligonucleotides were used:

```
orf2bNcofw (SEQ ID No. 30):
(5'-TATATACCATGGCGCTTTCACCGCCAGGC-3'
(NcoI recognition sequence is underlined)

orf4Salrv (SEQ ID No. 31):
5'-TATATAGTCGACTTAATTCGCCTGACCGGCCAG-3'
(SalI recognition sequence is underlined).
```

The PCR product (2,220 bp) was purified by means of the QIAquick PCR purification kit from Qiagen, Hilden, Germany, according to the manufacturer's information and ligated into the per-BluntII-TOPO vector, yielding the pCR-BluntII-Topo-KpGDRF vector. Ligation and subsequent transformation into *E. coli* cells are carried out according to the information by the manufacturer, Invitrogen Corporation, Carlsbad (Zero Blunt TOPO PCR Cloning Kit).

The GDRF sequence was then excised from the vector by digesting pCR-BluntII-Topo-KpGDRF with PciI and SalI and ligated into the NcoI and SalI-cut pACYC-Duet expression vector, resulting in pACYCDuet-KpGDRF (6142 bp).

b) Construction of plasmid pAS50_Ec_aldH for over-expression of *K. pneumoniae* glycerol dehydratase (GD) and *E. coli* aldehyde dehydrogenase, aldH.

The three subunits of *K. pneumoniae* GD are naturally organized in a single operon (genes gldA, gldB and gldC). They were amplified by means of PCR, again using chromosomal DNA of *K. pneumoniae* DSM2026 as template.

The following oligonucleotides were used for the amplification:

```
KpGDNdefw (SEQ ID No. 32)
5'-TATATACATATGAAAAGATCAAAACGATTTGCAGTACTGG-3'
(NdeI recognition sequence is underlined)

KpGDSalrv (SEQ ID No. 33):
5'-TATATAGTCGACTTAGCTTCCTTTACGCAGCTTATGC-3'
(SalI recognition sequence is underlined)
```

The amplicon was ligated into the pCR-BluntII-TOPO vector, yielding the vector pCR-BluntII-Topo-KpGD vector. Ligation and subsequent transformation into *E. coli* cells were carried out according to the information by the manufacturer, Invitrogen Corporation, Carlsbad (Zero Blunt TOPO PCR Cloning Kit).

The GD-encoding fragment was excised from the pCR-BluntII-Topo-KpGD vector by XbaI (blunted by Klenow fill in) and NdeI and ligated into a pET-Duet expression vector cut with NdeI and EcoRV, resulting in the plasmid pAS50(8161 bp).

The *E. coli* aldH gene was then amplified. For this, chromosomal DNA of *E. coli* K12 was used as template, with the PCR primers used being the oligonucleotides

```
1228_ald_fp (SEQ ID No. 34):
5'-AAAACATATGAATTTTCATCATCTGGCTTACTGG-3'
(NdeI recognition sequence is underlined)
and

1228_ald_rp (SEQ ID No. 35):
5'-AAAACATATGTATATTTCCTTCTTTCAGGCCTCCAGGCTTATCCAG
ATG-3')
(NdeI recognition sequence is underlined).
```

The PCR amplicon was gel-purified and then ligated by means of digestion of NdeI into the NdeI site of plasmid pAS50, producing the plasmid pAS50_Ec_aldH (9666 bp).

c) Construction of plasmid pCDFDuet-1_Rs-ccR_Cau_pcs for overexpression of *Chloroflexus aurantiacus* propionyl-coenzyme A synthase (Pcs) and of *Rhodobacter sphaeroides* crotonyl-coenzyme A carboxylase/reductase (CCR).

For heterologous expression in *E. coli* and purification of CCR, the gene was cloned into the pET3d expression vector, yielding plasmid pTE13: the *R. sphaeroides* ccr gene was amplified by PCR using the oligonucleotides

```
ccr-fw (SEQ ID No. 36):
5'-GGAGGCAACCATGGCCCTCGACGTGCAGAG-3'
(NcoI recognition sequence is underlined)
and

ccr-rev (SEQ ID No. 37):
5'-GAGACTTGCGGATCCCTCCGATCAGGCCTTGC-3'
(BamHI recognition sequence is underlined),
```

using chromosomal DNA of the strain *T. sphaeroides* 2.4.1. (DSMZ 158) as template. The PCR product was ligated by way of an NcoI/BamHI fragment into the NcoI/BamHI-cut vector pET3d (Merck, Germany), producing the plasmid pTE13.

The ccr gene was subcloned by way of an NcoI/BamHI fragment from pTE13 into the NcoI/BamHI cleavage sites of the pCDFDuet-1 plasmid (Merck, Germany), producing the plasmid pCDFDuet-1_Rs_ccr.

The *C. aurantiacus* pcs gene was then amplified by PCR using the oligonucleotides

```
1228_Cau_pcs_fp(71) (SEQ ID No. 38):
5'-AAAACATATGATCGACACTGCGCCCCTTGC-3'
(NdeI recognition sequence is underlined)
and

1228_Cau_pcs_rp(74) (SEQ ID No. 39):
5'-AAGACGTCCTACCGCTCGCCGGCCGTCC-3'
(AatII recognition sequence is underlined),
```

using chromosomal DNA of the strain *C. aurantiacus* OK-70-fl (DSM 636) as template. The amplicon was purified by gel extraction and then ligated, via digestion with NdeI/AatII, into the correspondingly cut vector pCDFDuet-1_Rs_ccr, producing the plasmid pCDFDuet-1_Rs_ccr_Cau_pcs (10 472 bp).

d) Construction of plasmid pCOLADuet_St_mcr_oCg_Tth_HIBDH_oCg for over-expression of *Sulfolobus tokodaii* malonyl-CoA reductase (Mcr) and of *Thermus thermophilus* 3-hydroxyisobutyrate dehydrogenase (3-HIB-DH)

First, a variant of the *S. tokodaii* mcr gene was synthesized in line with the codon usage of *Corynebacterium glutamicum* (St_mcr_oCg). The synthesis was carried out at GeneArt, Germany, and the artificial gene, St_mcr_oCg, was provided in the form of the plasmid pGA4_MMCoAR_ST (SEQ ID No. 40). pGA4_MMCoAR_ST DNA was used as PCR template in order to amplify the artificial gene, St_mcr_oCg, using the oligonucleotides

```
1228_MMCoAR_fp (SEQ ID No. 41):
5'-AACCATGGGCCGCACCCTGAAGG-3'
(NcoI recognition sequence is underlined)
and

1228_MMCoAR_rp (SEQ ID No. 42)
5'-AAGGATCCTTACTTTTCGATGTAGCCCTTTTCC-3'
(BamHI recognition sequence is underlined).
```

The amplicon was purified by gel extraction and then digested with NcoI/BamHI and ligated into the corresponding cleavage sites of the pCOLADuet_1 plasmid (Merck, Germany), producing the plasmid pCOLADuet_St_mcr_oCg.

A variant of the *T. thermophilus* MmsB gene (encoding a 3-HIB-DH), which is in line with the codon usage of *Corynebacterium glutamicum*, was likewise provided by gene synthesis (GeneArt, Germany), to be precise in the form of the plasmid pGA4_3HIBDH_TT (SEQ ID No. 43).

pGA4_3HIBDH_TT was used as PCR template in order to amplify the artificial gene, Tth_HIBDH_oCg, using the oligonucleotides

```
1228_Tth_HIBDH_fp (SEQ ID No. 44):
5'-AAAACATATGGAAAAGGTGGCATTCATCG-3'
```

-continued

```
(NdeI recognition sequence is underlined)
and

1228_Tth_HIBDH_rp (SEQ ID No. 45):
5'-AAAAGATCTTTAGCGGATTTCCACACCGCC-3'
(BglII recognition sequence is underlined).
```

The amplicon was gel-extracted and then cut with NdeI/BglII and ligated into the NdeI/BglII cleavage sites of the plasmid pCOLADuet_St_mcr_oCg, producing the plasmid pCOLADuet_St_mcr_oCg_Tth_HIBDH_oCg (5,620 bp).

e) The 4 plasmids, pACYCDuet-KpGDRF, pAS50_Ec-aldH, pCDFDuet-1_Rs_ccR_Cau_pcs and pCOLADuet_St_mcr_oCg_Tth_HIBDH_oCg, were then co-transformed into commercially available, chemically competent *E. coli* BL21 (DE3) cells (Merck, Germany), according to the manufacturer's protocol. Selection was carried out on LB agar supplemented with ampicillin (25 µg/ml), chloramphenicol (17 µg/ml), kanamycin (15 µg/ml) and streptomycin (25 µg/ml).

f) Induction of expression plasmids in *E. coli*

The plasmid-carrying *E. coli* strains described in e) above were cultured in modified M9 medium (6.8 g/l $Na_2HPO_4 \times 2H_2O$; 3 g/l $KH_2PO_4$; 0.5 g/l NaCl; 1 g/l $NH_4Cl$; 1.25 g/l yeast extract; 1% v/v glycerol; 15 mg/l $CaCl_2 \times 2H_2O$; 250 mg/l $MgSO_4 \times 7H_2O$; 1% v/v Gibco MEM Vitamin solution; 41.9 g/l MOPS). The medium was supplemented with ampicillin (25 µg/ml), chloramphenicol (17 µg/ml), kanamycin (15 µg/ml) and streptomycin (25 µg/ml). The entire cultivation (pre- and main cultures) was carried out on a shaker with temperature control at 37° C. The strains were first cultured in 5 ml of medium overnight. Subsequently, 20 ml of medium in a 100 ml flask with baffles were then inoculated from the overnight culture at a ratio of 1:20 and cultured further. At $OD_{600}$ of approx. 0.8, 6 µM cobalamine and 1 µM IPTG were added, and the culture was incubated for another 4 hours. At this time, 2.5 ml of cell suspension were removed and stored at −20° C. until analysis.

g) Detection and quantification of 3-HIB were carried out by means of ion chromatography (IC) and conductivity detection. For this, 2.5 ml of samples are thawed at room temperature and centrifuged (10 min, 13 200 rpm). The supernatant is purified using a syringe filter (pore size 0.44 µm). The measurement is carried out using a Metrohm Compact IC 761 with autosampler. Mobile phase: 8 mM NaOH. Column: Dionex AS15 4×250 mm, precolumn AG15 4×50 mm. Column temperature: 25° C. Flow rate: 1.4 ml/min. Injection volume: 10 µl.

h) Dehydration of 3-hydroxyisobutyric acid to methacrylate 5 ml of a concentrated solution of 3-hydroxy-isobutyric acid (0.2 g/l), produced by the process described in f) above, are admixed with NaOH (0.06 mg) with stirring. The solution is incubated with stirring and reflux condensation at 185-195° C. under vacuum (300 torr). A further 0.5 mg of 3-hydroxyisobutyric acid in 5 ml are added every hour over a period of 5 h. The solution contains 0.4 percent by weight p-methoxyphenol in order to prevent methacrylate from polymerizing. The reaction is stopped after 24 h of incubation. Conversion of 3-hydroxy-isobutyric acid to methacrylate is above 90%. Methacrylic acid is removed from the reaction mixture by distillation.

We claim:

1. A process for preparing a methacrylic acid or a methacrylic ester, comprising preparing a 3-hydroxyisobutyric acid by a process comprising:

culturing a genetically modified cell which forms 3-hydroxyisobutyric acid, or polyhydroxy-alkanoate comprising 3-hydroxyisobutyric acid via a pathway employing succinyl-coenzyme A as an intermediate and methylmalonate semialdehyde as precursor in a nutrient medium comprising a carbon source under a condition wherein at least a portion of the carbon source is enzymatically converted to 3-hydroxyisobutyric acid or a polyhydroxy-alkanoate comprising 3-hydroxyisobutyric acid, wherein the carbon source is at least one source selected from the group consisting of a carbohydrate, glycerol, L-valine, and L-glutamate;

wherein the genetically modified cell comprises:

(1) NCg11470, NCg11471, and NCg11472 genes encoding an enzyme $E_1$ which catalyses conversion of succinyl-coenzyme A to methylmalonyl coenzyme A;

(2) a gene of *S. tokodaii* encoding malonyl-coenzyme A reductase that provides enzyme activities of enzymes $E_2$ and $E_3$, wherein the enzyme $E_2$ catalyses conversion of methylmalonyl-coenzyme A to methylmalonate, and the enzyme $E_3$ catalyses conversion of methylmalonate to methylmalonate semialdehyde; and (3) a gene of *Thermus thermophilus* encoding an enzyme $E_4$ which catalyses conversion of methylmalonate semialdehyde to 3-hydroxyisobutyrate;

wherein the genes (1), (2), and (3) express respective enzymes which catalyze the formation of 3-hydroxyisobutyric acid by the genetically modified cells when the cells are cultured in a medium comprising a carbohydrate source;

optionally isolating the 3-hydroxyisobutyric acid from the nutrient medium;

optionally neutralizing the 3-hydroxyisobutyric acid; and dehydrating the 3-hydroxyisobutyric acid, to obtain methacrylic acid and optionally, esterifying the methacrylic acid;

wherein the genetically modified cell is *Corynebacterium glutamicum,* wherein the enzyme $E_1$ is a methylmalonyl-coenzyme A mutase of EC 5.4.99.2, the enzyme $E_2$ is a methylmalonyl-coenzyme A hydrolase (EC 3.1.2.17) which catalyzes the conversion of methylmalonyl-coenzyme A into methyl malonate;

the enzyme $E_3$ is an aldehyde dehydrogenase (EC 1.2.1.3) or an aldehyde oxidase (EC 1.2.3.1); and the enzyme $E_4$ is a 3-hydroxyisobutyrate dehydrogenase (EC 1.1.1.31).

2. A process of preparing polymethacrylic acid or polymethacrylic ester, comprising IIIA) preparing a methacrylic acid by the process according to claim 1, IIIB) carrying out free-radical polymerization of the methacrylic acid, and optionally esterifying at least in part the carboxyl groups of the methacrylic acid or the carboxylate group of the methacrylate before or after the free-radical polymerization reaction.

3. The process of claim 1, wherein an activity of said enzyme $E_1$ is increased in comparison with its activity in a wild type cell.

4. The process of claim 1, wherein an activity of the enzymes $E_2$ and $E_3$ is increased in comparison with an enzyme activity in a wild type cell.

5. The process of claim 1, wherein the gene encoding said enzyme $E_1$ is from *Corynebacterium glutamicum* (ATCC13032) and comprises the nucleotide sequence of SEQ ID NO:1, the gene encoding said enzyme malonyl-coenzyme A reductase from *S. tokodaii* that provides enzyme activities of enzymes $E_2$ and $E_3$ comprises the nucleotide sequence of SEQ ID NO 3 and the gene encoding said enzyme $E_4$ is mmsB from *Thermus thermophilus*.

6. The process of claim 1, wherein said enzyme $E_1$ comprises the amino acid sequence of SEQ ID NO:2 and said enzyme malonyl-coenzyme A reductase comprises the amino acid sequence of SEQ ID NO:4.

* * * * *

SEQUENCE LISTING

<160> NUMBER OF SEQ ID NOS: 45

<210> SEQ ID NO 1
<211> LENGTH: 2214
<212> TYPE: DNA
<213> ORGANISM: Corynebacterium glutamicum

<400> SEQUENCE: 1
atgacgtcga tccctaattt ttcagacatc ccattgactg ctgagacacg tgcatcggag 60
tcacacaacg ttgacgccgg caaggtgtgg aacactcccg aaggcattga tgtcaagcgc 120
gtattcacgc aggctgaccg cgacgaggcg caagcggcgg gacatccggt ggattctttg 180
ccaggtcaaa agccatttat gcgcgggccg tacccaacta tgtacaccaa tcagccgtgg 240
acgattcgcc agtacgcagg cttttcaacc gccgcggaat ccaatgcgtt ttatcggagg 300
aaccttgctg cgggtcaaaa aggtttgtcg gttgcgttcg atctagcgac ccaccgcggt 360
tatgactcgg ataatgagcg cgtggtcggc gatgtgggta tggccggcgt ggcgattgat 420
tcgattttgg atatgcgtca gctgtttgat ggcattgatt tgtccagcgt gtcggtgtcg 480
atgaccatga atggcgctgt gctgccgatt cttgcgttct atatcgtggc ggctgaggaa 540
caaggtgtgg gtccggagca gcttgcgggc acgatccaga atgacatctt gaaagaattt 600
atggtgcgca acacctatat ttatccgccg aagccgtcga tgcgcatcat ttccaacatc 660
tttgagtaca cctccttgaa gatgccacgt tttaactcca tttcgatttc tggctatcac 720
atccaggaag cgggagcgac tgccgatttg gagctggcct acactctggc ggatggtatt 780
gaatacatcc gtgcaggtaa agaggtaggc cttgacgtgg ataagttcgc gcctcgtctg 840
tccttcttct ggggtatttc tatgtacacc ttcatggaga tcgcaaagct gcgtgcggga 900
cgactgctgt ggagcgagtt ggtggcaaaa ttcgatccga aaaacgccaa gtcccagtcg 960
ctgcgcacgc actcgcagac ctctggttgg tcgttgaccg cgcaggatgt gtacaacaac 1020
gtcgcccgca ccgcgattga ggcgatggct gcaacccagg gccacaccca gtcgctgcac 1080
accaatgcac ttgatgaggc gttggcgctg cccaccgatt tctctgctcg tatcgcccga 1140
aacacccagc tgttgctgca gcaggaatct ggcacggtgc gtccagttga tccatgggcg 1200
ggctcctatt acgtggagtg gttgaccaat gagctggcta accgcgcgcg caagcacatc 1260
gatgaggtgg aggaagccgg cggaatggcg caggccaccg cgcagggaat tcctaagctg 1320
cgcattgagg aatcagcggc acgcacccag gctcgcattg attccggccg ccaggcgctg 1380
atcggcgtga atcgctacgt ggcggaagaa gatgaggaaa ttgaagtcct caaggttgac 1440
aacaccaagg ttcgcgcaga acagttggct aaactcgcgc aactgaaagc agagcgcaac 1500
gatgcggaag tcaaggctgc gctggatgcg ttgacagctg ctgcccgcaa cgagcataaa 1560
gagccagggg atttggatca gaacctgctc aaacttgccg tcgatgctgc gcgcgcaaaa 1620
gctaccattg gagagatctc cgatgctttg gaagttgtct ttggccgcca cgaagcagaa 1680
atcaggacgc tgtctggcgt gtacaaggat gaggttggaa aggaaggcac agtgagcaac 1740
gtcgaacgcg cgatcgccct ggctgacgcc tttgaggctg aggaaggccg ccgcccacgt 1800
atctttattg ccaagatggg ccaggatgga catgaccgtg gacagaaggt tgtcgcgtct 1860
gcctatgctg acctgggcat ggacgtggat gttggaccgc tgtttcaaac tccagccgaa 1920
gctgcccgcg ccgccgtgga cgccgatgtt cacgtggtgg gtatgtcttc gctggcagca 1980
ggccacctca ccttgctgcc cgagctgaag aaagaacttg cagctcttgg ccgcgatgac 2040
attctggtca ccgtgggcgg cgtcattccg ccgggcgatt tccaggatct ctacgatatg 2100
ggtgccgccg cgatttaccc tccaggaacc gtcatcgcgg agtcggcgat cgatctgatc 2160
acccgactcg ccgcacacct gggctttgac ctggatgtgg atgtgaatga gtga 2214

<210> SEQ ID NO 2
<211> LENGTH: 737
<212> TYPE: PRT
<213> ORGANISM: Corynebacterium glutamicum

<400> SEQUENCE: 2

Met Thr Ser Ile Pro Asn Phe Ser Asp Ile Pro Leu Thr Ala Glu Thr
1 5 10 15

Arg Ala Ser Glu Ser His Asn Val Asp Ala Gly Lys Val Trp Asn Thr
20 25 30

Pro Glu Gly Ile Asp Val Lys Arg Val Phe Thr Gln Ala Asp Arg Asp
35 40 45

Glu Ala Gln Ala Ala Gly His Pro Val Asp Ser Leu Pro Gly Gln Lys
50 55 60

Pro Phe Met Arg Gly Pro Tyr Pro Thr Met Tyr Thr Asn Gln Pro Trp
65 70 75 80

Thr Ile Arg Gln Tyr Ala Gly Phe Ser Thr Ala Ala Glu Ser Asn Ala
85 90 95

Phe Tyr Arg Arg Asn Leu Ala Ala Gly Gln Lys Gly Leu Ser Val Ala
100 105 110

Phe Asp Leu Ala Thr His Arg Gly Tyr Asp Ser Asp Asn Glu Arg Val
115 120 125

Val Gly Asp Val Gly Met Ala Gly Val Ala Ile Asp Ser Ile Leu Asp
130 135 140

Met Arg Gln Leu Phe Asp Gly Ile Asp Leu Ser Ser Val Ser Val Ser
145 150 155 160

Met Thr Met Asn Gly Ala Val Leu Pro Ile Leu Ala Phe Tyr Ile Val
165 170 175

Ala Ala Glu Glu Gln Gly Val Gly Pro Glu Gln Leu Ala Gly Thr Ile
180 185 190

Gln Asn Asp Ile Leu Lys Glu Phe Met Val Arg Asn Thr Tyr Ile Tyr
195 200 205

Pro Pro Lys Pro Ser Met Arg Ile Ile Ser Asn Ile Phe Glu Tyr Thr
210 215 220

Ser Leu Lys Met Pro Arg Phe Asn Ser Ile Ser Ile Ser Gly Tyr His
225 230 235 240

Ile Gln Glu Ala Gly Ala Thr Ala Asp Leu Glu Leu Ala Tyr Thr Leu
245 250 255

Ala Asp Gly Ile Glu Tyr Ile Arg Ala Gly Lys Glu Val Gly Leu Asp
260 265 270

Val Asp Lys Phe Ala Pro Arg Leu Ser Phe Phe Trp Gly Ile Ser Met
275 280 285

Tyr Thr Phe Met Glu Ile Ala Lys Leu Arg Ala Gly Arg Leu Leu Trp
290 295 300

Ser Glu Leu Val Ala Lys Phe Asp Pro Lys Asn Ala Lys Ser Gln Ser
305 310 315 320

Leu Arg Thr His Ser Gln Thr Ser Gly Trp Ser Leu Thr Ala Gln Asp
325 330 335

Val Tyr Asn Asn Val Ala Arg Thr Ala Ile Glu Ala Met Ala Ala Thr
340 345 350

-continued

```
Gln Gly His Thr Gln Ser Leu His Thr Asn Ala Leu Asp Glu Ala Leu
        355                 360                 365

Ala Leu Pro Thr Asp Phe Ser Ala Arg Ile Ala Arg Asn Thr Gln Leu
    370                 375                 380

Leu Leu Gln Gln Glu Ser Gly Thr Val Arg Pro Val Asp Pro Trp Ala
385                 390                 395                 400

Gly Ser Tyr Tyr Val Glu Trp Leu Thr Asn Glu Leu Ala Asn Arg Ala
                405                 410                 415

Arg Lys His Ile Asp Glu Val Glu Glu Ala Gly Gly Met Ala Gln Ala
            420                 425                 430

Thr Ala Gln Gly Ile Pro Lys Leu Arg Ile Glu Glu Ser Ala Ala Arg
        435                 440                 445

Thr Gln Ala Arg Ile Asp Ser Gly Arg Gln Ala Leu Ile Gly Val Asn
    450                 455                 460

Arg Tyr Val Ala Glu Glu Asp Glu Glu Ile Glu Val Leu Lys Val Asp
465                 470                 475                 480

Asn Thr Lys Val Arg Ala Glu Gln Leu Ala Lys Leu Ala Gln Leu Lys
                485                 490                 495

Ala Glu Arg Asn Asp Ala Glu Val Lys Ala Ala Leu Asp Ala Leu Thr
            500                 505                 510

Ala Ala Ala Arg Asn Glu His Lys Glu Pro Gly Asp Leu Asp Gln Asn
        515                 520                 525

Leu Leu Lys Leu Ala Val Asp Ala Ala Arg Ala Lys Ala Thr Ile Gly
    530                 535                 540

Glu Ile Ser Asp Ala Leu Glu Val Val Phe Gly Arg His Glu Ala Glu
545                 550                 555                 560

Ile Arg Thr Leu Ser Gly Val Tyr Lys Asp Glu Val Gly Lys Glu Gly
                565                 570                 575

Thr Val Ser Asn Val Glu Arg Ala Ile Ala Leu Ala Asp Ala Phe Glu
            580                 585                 590

Ala Glu Glu Gly Arg Arg Pro Arg Ile Phe Ile Ala Lys Met Gly Gln
        595                 600                 605

Asp Gly His Asp Arg Gly Gln Lys Val Val Ala Ser Ala Tyr Ala Asp
    610                 615                 620

Leu Gly Met Asp Val Asp Val Gly Pro Leu Phe Gln Thr Pro Ala Glu
625                 630                 635                 640

Ala Ala Arg Ala Ala Val Asp Ala Asp Val His Val Val Gly Met Ser
                645                 650                 655

Ser Leu Ala Ala Gly His Leu Thr Leu Leu Pro Glu Leu Lys Lys Glu
            660                 665                 670

Leu Ala Ala Leu Gly Arg Asp Asp Ile Leu Val Thr Val Gly Gly Val
        675                 680                 685

Ile Pro Pro Gly Asp Phe Gln Asp Leu Tyr Asp Met Gly Ala Ala Ala
    690                 695                 700

Ile Tyr Pro Pro Gly Thr Val Ile Ala Glu Ser Ala Ile Asp Leu Ile
705                 710                 715                 720

Thr Arg Leu Ala Ala His Leu Gly Phe Asp Leu Asp Val Asp Val Asn
                725                 730                 735

Glu
```

<210> SEQ ID NO 3
<211> LENGTH: 1071
<212> TYPE: DNA
<213> ORGANISM: Sulfolobus tokodaii

<400> SEQUENCE: 3

```
atgaggagaa cattaaaagc cgcaatatta ggtgctactg gtttagtagg aatcgaatac     60
gtaagaatgc tatcaaatca tccttatatt aaaccagcat atttagctgg aaaaggttca    120
gtgggtaaac cgtatggtga ggtagtaaga tggcaaacag taggacaagt tcctaaggaa    180
atagctgata tggaaataaa accaactgat cctaagttaa tggatgatgt agacataata    240
ttttctccat tacctcaagg tgctgctggc ccagtagaag aacaatttgc aaaagaagga    300
ttccctgtga ttagtaattc accagatcat agatttgatc ctgatgttcc cttattggtt    360
cctgaactaa atcctcatac tattagctta attgatgagc aaagaaaaag aagagaatgg    420
aaaggattta tagtaactac accactatgc acagcccagg gtgcagcaat accattaggt    480
gctatattta aagattataa gatggatgga gcatttataa ctactattca atcgctatct    540
ggtgccggtt atccaggaat accatcatta gatgtagtag ataatatctt gcctttaggt    600
gatggatacg atgccaagac gataaaagag atcttcagaa ttttaagcga agttaagaga    660
aatgtagatg aacctaaatt agaagatgta agcttagcag caacaactca tagaatagct    720
actatacatg gtcattatga agtactatat gtatcgttca aagaggaaac tgctgctgaa    780
aaagttaagg agactttaga aaactttaga ggggaaccac aagatctaaa attaccaact    840
gcaccttcaa agccaattat cgttatgaat gaggatacaa gacctcaagt ctattttgat    900
agatgggctg ggatattcc aggaatgagt gtagttgtag gtagattaaa gcaagtgaat    960
aagagaatga taaggttagt atcattaatt cataacacgg tcagaggagc cgcaggagga   1020
ggtatattag cagctgaatt acttgtcgaa aaaggatata ttgaaaagta a            1071
```

<210> SEQ ID NO 4
<211> LENGTH: 356
<212> TYPE: PRT
<213> ORGANISM: Sulfolobus tokodaii

<400> SEQUENCE: 4

```
Met Arg Arg Thr Leu Lys Ala Ala Ile Leu Gly Ala Thr Gly Leu Val
1               5                   10                  15

Gly Ile Glu Tyr Val Arg Met Leu Ser Asn His Pro Tyr Ile Lys Pro
            20                  25                  30

Ala Tyr Leu Ala Gly Lys Gly Ser Val Gly Lys Pro Tyr Gly Glu Val
        35                  40                  45

Val Arg Trp Gln Thr Val Gly Gln Val Pro Lys Glu Ile Ala Asp Met
    50                  55                  60

Glu Ile Lys Pro Thr Asp Pro Lys Leu Met Asp Asp Val Asp Ile Ile
65                  70                  75                  80

Phe Ser Pro Leu Pro Gln Gly Ala Ala Gly Pro Val Glu Glu Gln Phe
                85                  90                  95

Ala Lys Glu Gly Phe Pro Val Ile Ser Asn Ser Pro Asp His Arg Phe
            100                 105                 110

Asp Pro Asp Val Pro Leu Leu Val Pro Glu Leu Asn Pro His Thr Ile
        115                 120                 125

Ser Leu Ile Asp Glu Gln Arg Lys Arg Arg Glu Trp Lys Gly Phe Ile
    130                 135                 140

Val Thr Thr Pro Leu Cys Thr Ala Gln Gly Ala Ala Ile Pro Leu Gly
145                 150                 155                 160

Ala Ile Phe Lys Asp Tyr Lys Met Asp Gly Ala Phe Ile Thr Thr Ile
                165                 170                 175
```

-continued

Gln Ser Leu Ser Gly Ala Gly Tyr Pro Gly Ile Pro Ser Leu Asp Val
            180                 185                 190

Val Asp Asn Ile Leu Pro Leu Gly Asp Gly Tyr Asp Ala Lys Thr Ile
        195                 200                 205

Lys Glu Ile Phe Arg Ile Leu Ser Glu Val Lys Arg Asn Val Asp Glu
    210                 215                 220

Pro Lys Leu Glu Asp Val Ser Leu Ala Ala Thr Thr His Arg Ile Ala
225                 230                 235                 240

Thr Ile His Gly His Tyr Glu Val Leu Tyr Val Ser Phe Lys Glu Glu
                245                 250                 255

Thr Ala Ala Glu Lys Val Lys Glu Thr Leu Glu Asn Phe Arg Gly Glu
            260                 265                 270

Pro Gln Asp Leu Lys Leu Pro Thr Ala Pro Ser Lys Pro Ile Ile Val
        275                 280                 285

Met Asn Glu Asp Thr Arg Pro Gln Val Tyr Phe Asp Arg Trp Ala Gly
    290                 295                 300

Asp Ile Pro Gly Met Ser Val Val Val Gly Arg Leu Lys Gln Val Asn
305                 310                 315                 320

Lys Arg Met Ile Arg Leu Val Ser Leu Ile His Asn Thr Val Arg Gly
                325                 330                 335

Ala Ala Gly Gly Gly Ile Leu Ala Ala Glu Leu Leu Val Glu Lys Gly
            340                 345                 350

Tyr Ile Glu Lys
        355

<210> SEQ ID NO 5
<211> LENGTH: 1293
<212> TYPE: DNA
<213> ORGANISM: Rhodobacter sphaeroides

<400> SEQUENCE: 5
atggccctcg acgtgcagag cgatatcgtc gcctacgacg cgcccaagaa ggacctctac 60
gagatcggcg agatgccgcc tctcggccat gtgccgaagg agatgtatgc ttgggccatc 120
cggcgcgagc gtcatggcga gccggatcag gccatgcaga tcgaggtggt cgagacgccc 180
tcgatcgaca gccacgaggt gctcgttctc gtgatggcgg cgggcgtgaa ctacaacggc 240
atctgggccg gcctcggcgt gcccgtctcg ccgttcgacg gtcacaagca gccctatcac 300
atcgcgggct ccgacgcgtc gggcatcgtc tgggcggtgg gcgacaaggt caagcgctgg 360
aaggtgggcg acgaggtcgt gatccactgc aaccaggacg acggcgacga cgaggaatgc 420
aacggcggcg acccgatgtt ctcgcccacc cagcggatct ggggctacga gacgccggac 480
ggctccttcg cccagttcac ccgcgtgcag gcgcagcagc tgatgaagcg tccgaagcac 540
ctgacctggg aagaggcggc ctgctacacg ctgaccctcg ccaccgccta ccggatgctc 600
ttcggccaca agccgcacga cctgaagccg gggcagaacg tgctggtctg gggcgcctcg 660
ggcggcctcg gctcctacgc gatccagctc atcaacacgg cgggcgccaa tgccatcggc 720
gtcatctcag aggaagacaa gcgcgacttc gtcatggggc tgggcgccaa gggcgtcatc 780
aaccgcaagg acttcaagtg ctggggccag ctgcccaagg tgaactcgcc cgaatataac 840
gagtggctga aggaggcgcg caagttcggc aaggccatct gggacatcac cggcaagggc 900
atcaacgtcg acatggtgtt cgaacatccg ggcgaggcga ccttcccggt ctcgtcgctg 960
gtggtgaaga agggcggcat ggtcgtgatc tgcgcgggca ccaccggctt caactgcacc 1020

-continued

```
ttcgacgtcc gctacatgtg gatgcaccag aagcgcctgc agggcagcca tttcgccaac   1080

ctcaagcagg cctccgcggc caaccagctg atgatcgagc gccgcctcga tccctgcatg   1140

tccgaggtct tcccctgggc cgagatcccg gctgcccata cgaagatgta taagaaccag   1200

cacaagcccg gcaacatggc ggtgctggtg caggccccgc gcacggggtt gcgcaccttc   1260

gccgacgtgc tcgaggccgg ccgcaaggcc tga                                 1293


<210> SEQ ID NO 6
<211> LENGTH: 430
<212> TYPE: PRT
<213> ORGANISM: Rhodobacter sphaeroides

<400> SEQUENCE: 6

Met Ala Leu Asp Val Gln Ser Asp Ile Val Ala Tyr Asp Ala Pro Lys
1               5                   10                  15

Lys Asp Leu Tyr Glu Ile Gly Glu Met Pro Pro Leu Gly His Val Pro
            20                  25                  30

Lys Glu Met Tyr Ala Trp Ala Ile Arg Arg Glu Arg His Gly Glu Pro
        35                  40                  45

Asp Gln Ala Met Gln Ile Glu Val Val Glu Thr Pro Ser Ile Asp Ser
    50                  55                  60

His Glu Val Leu Val Leu Val Met Ala Ala Gly Val Asn Tyr Asn Gly
65                  70                  75                  80

Ile Trp Ala Gly Leu Gly Val Pro Val Ser Pro Phe Asp Gly His Lys
                85                  90                  95

Gln Pro Tyr His Ile Ala Gly Ser Asp Ala Ser Gly Ile Val Trp Ala
            100                 105                 110

Val Gly Asp Lys Val Lys Arg Trp Lys Val Gly Asp Glu Val Val Ile
        115                 120                 125

His Cys Asn Gln Asp Asp Gly Asp Asp Glu Glu Cys Asn Gly Gly Asp
    130                 135                 140

Pro Met Phe Ser Pro Thr Gln Arg Ile Trp Gly Tyr Glu Thr Pro Asp
145                 150                 155                 160

Gly Ser Phe Ala Gln Phe Thr Arg Val Gln Ala Gln Gln Leu Met Lys
                165                 170                 175

Arg Pro Lys His Leu Thr Trp Glu Glu Ala Ala Cys Tyr Thr Leu Thr
            180                 185                 190

Leu Ala Thr Ala Tyr Arg Met Leu Phe Gly His Lys Pro His Asp Leu
        195                 200                 205

Lys Pro Gly Gln Asn Val Leu Val Trp Gly Ala Ser Gly Gly Leu Gly
    210                 215                 220

Ser Tyr Ala Ile Gln Leu Ile Asn Thr Ala Gly Ala Asn Ala Ile Gly
225                 230                 235                 240

Val Ile Ser Glu Glu Asp Lys Arg Asp Phe Val Met Gly Leu Gly Ala
                245                 250                 255

Lys Gly Val Ile Asn Arg Lys Asp Phe Lys Cys Trp Gly Gln Leu Pro
            260                 265                 270

Lys Val Asn Ser Pro Glu Tyr Asn Glu Trp Leu Lys Glu Ala Arg Lys
        275                 280                 285

Phe Gly Lys Ala Ile Trp Asp Ile Thr Gly Lys Gly Ile Asn Val Asp
    290                 295                 300

Met Val Phe Glu His Pro Gly Glu Ala Thr Phe Pro Val Ser Ser Leu
305                 310                 315                 320

Val Val Lys Lys Gly Gly Met Val Val Ile Cys Ala Gly Thr Thr Gly
```

-continued

```
                325                 330                 335

Phe Asn Cys Thr Phe Asp Val Arg Tyr Met Trp Met His Gln Lys Arg
            340                 345                 350

Leu Gln Gly Ser His Phe Ala Asn Leu Lys Gln Ala Ser Ala Ala Asn
        355                 360                 365

Gln Leu Met Ile Glu Arg Arg Leu Asp Pro Cys Met Ser Glu Val Phe
    370                 375                 380

Pro Trp Ala Glu Ile Pro Ala Ala His Thr Lys Met Tyr Lys Asn Gln
385                 390                 395                 400

His Lys Pro Gly Asn Met Ala Val Leu Val Gln Ala Pro Arg Thr Gly
                405                 410                 415

Leu Arg Thr Phe Ala Asp Val Leu Glu Ala Gly Arg Lys Ala
            420                 425                 430


<210> SEQ ID NO 7
<211> LENGTH: 1233
<212> TYPE: DNA
<213> ORGANISM: Pseudomonas aeruginosa

<400> SEQUENCE: 7

atgagtgatt acgagccgtt gcgtctgcat gtcccggagc ccaccgggcg tcctggctgc     60

aagaccgact tttcctatct gcacctgtcc cccgccggcg aggtacgcaa gccgccggtg    120

gatgtcgagc ccgccgagac cagcgacctg gcctacagcc tggtacgtgt gctcgacgac    180

gacggccacg ccgtcggtcc ctggaatccg cagctcagca acgaacaact gctgcgcggc    240

atgcgggcga tgctcaagac ccgcctgttc gacgcgcgca tgctcaccgc gcaacggcag    300

aaaaagcttt ccttctatat gcaatgcctc ggcgaggaag ccatcgccac cgcccacacc    360

ctggccctgc gcgacggcga catgtgcttt ccgacctatc gccagcaagg catcctgatc    420

acccgcgaat acccgctggt ggacatgatc tgccagcttc tctccaacga ggccgacccg    480

ctcaagggcc gccagctgcc gatcatgtac tcgagcaagg aggcaggttt cttctccatc    540

tccggcaacc tcgccaccca gttcatccag gcggtcggct ggggcatggc ctcggcgatc    600

aagggcgaca cgcgcatcgc ctcggcctgg atcggcgacg gcgccaccgc cgagtcggac    660

ttccacaccg ccctcacctt cgcccatgtc taccgcgcgc cggtaatcct caacgtggtc    720

aacaaccagt gggcgatctc caccttccag gccatcgccg gcggcgaagg caccaccttc    780

gccaaccgtg gcgtgggctg cgggatcgcc tcgctgcggg tcgacggcaa tgacttcctg    840

gcggtctacg ccgcctccga gtgggccgcc gagcgcgccc ggcgcaacct cgggccgagc    900

ctgatcgaat gggtcaccta ccgcgccggc ccgcactcga cttcggacga cccgtccaag    960

taccgccccg ccgacgactg gaccaacttc ccgctgggcg acccgatcgc ccgcctgaag   1020

cggcacatga tcggcctcgg catctggtcg gaggaacagc acgaagccac ccacaaggcc   1080

ctcgaagccg aagtactggc cgcgcagaaa caggcggaga gccatggcac cctgatcgac   1140

ggccgggtgc cgagcgccgc cagcatgttc gaggacgtct atgcagaact gccggagcac   1200

ctgcgccggc aacgccagga gctcggggta tga                                1233


<210> SEQ ID NO 8
<211> LENGTH: 1049
<212> TYPE: DNA
<213> ORGANISM: Pseudomonas aeruginosa

<400> SEQUENCE: 8

atgccatgaa cccgcaacac gagaacgccc agacggtcac cagcatgacc atgatccagg     60
```

-continued

```
cgctgcgctc ggcgatggac atcatgctcg agcgcgacga cgacgtggtg gtattcggcc    120

aggacgtcgg ctacttcggc ggcgtgttcc gctgcaccga aggcctgcag aagaaatacg    180

gcacctcgcg ggtgttcgat gcgccgatct ccgagagcgg catcatcggc gccgcggtcg    240

gcatgggtgc ctacggcctg cgcccggtgg tggagatcca gttcgccgac tacgtctacc    300

cggcctccga ccagttgatc tccgaggcgg cgcgcctgcg ctatcgctcg gccggcgact    360

tcatcgtgcc gatgaccgta cgcatgccct gtggcggcgg catctacggc gggcaaacgc    420

acagccagag cccggaggcg atgttcaccc aggtctgcgg cctgcgcacg gtgatgccgt    480

ccaaccccta cgacgccaag ggcctgctga tcgcctgcat cgagaacgac gacccggtga    540

tcttcctcga gcccaagcgc ctctacaacg gcccgttcga tggccaccac gaccgcccgg    600

tgacgccctg gtccaagcat ccggccagcc aggtgccgga cggctactac aaggtgccgc    660

tggacaaggc ggcgatcgtc cgccccggcg cggcgctgac cgtgctgacc tacggcacca    720

tggtctacgt ggcccaggcc gcggccgacg agaccggcct ggacgccgag atcatcgacc    780

tgcgcagcct ctggccgctg gacctggaaa ccatcgtcgc ctcggtgaag aagaccggcc    840

gctgcgtcat cgcccacgag gcgacccgca cctgcgggtt cggcgccgag ctgatgtcgc    900

tggtgcagga gcactgcttc caccacctgg aggcgccgat cgagcgcgtc accggttggg    960

acaccccta cccgcatgcc caggagtggg cgtatttccc cggccccgcg cgcgtcggcg    1020

cggcattcaa gcgtgtgatg gaggtctga                                      1049

<210> SEQ ID NO 9
<211> LENGTH: 924
<212> TYPE: DNA
<213> ORGANISM: Pseudomonas aeruginosa

<400> SEQUENCE: 9

atgtcgatgg ccgatcgtga tggcgtgatc tggtatgacg gtgaactggt gcagtggcgc     60

gacgcgacca cgcacgtgct gacccatacc ctgcactatg gaatgggcgt gttcgagggc    120

gtgcgcgcct acgacacccc gcagggcacg gcgatcttcc gcctgcaggc gcataccgac    180

cggctgttcg actccgcgca catcatgaac atgcagatcc cgtacagccg cgacgagatc    240

aacgaggcga cccgcgccgc cgtgcgcgag aacaacctgg aaagcgccta tatccgcccg    300

atggtgttct acggaagcga aggcatgggc ctgcgcgcca gcggcctgaa ggtccatgtg    360

atcatcgccg cctggagctg ggcgcctac atgggcgagg aagccctgca gcaaggcatc    420

aaggtgcgca ccagttcctt cacccgccac cacgtcaaca tctcgatgac ccgcgccaag    480

tccaacggcg cctacatcaa ctcgatgctg gccctccagg aagcgatctc cggcggcgcc    540

gacgaggcca tgatgctcga tccggaaggc tacgtggccg aaggctccgg cgagaacatc    600

ttcatcatca aggatggcgt gatctacacc ccggaagtca ccgcctgcct gaacggcatc    660

actcgtaaca ctatcctgac cctggccgcc gaacacggtt ttaaactggt cgagaagcgc    720

atcacccgcg acgaggtgta catcgccgac gaggccttct tcactggcac tgccgcggaa    780

gtcacgccga tccgcgaagt ggacggtcgc aagatcggcg ccggccgccg tggcccggtc    840

accgaaaagc tgcagaaagc ctatttcgac ctggtcagcg gcaagaccga ggcccacgcc    900

gagtggcgta ccctggtcaa gtaa                                           924

<210> SEQ ID NO 10
<211> LENGTH: 1128
<212> TYPE: DNA
```

-continued

<213> ORGANISM: Acinetobacter calcoaceticus

<400> SEQUENCE: 10
atgcaattta atgaagaaca gctattaatt caggatatgg cgaaaagttt tgccaatgaa 60
cagattaaat ctaatgcagc agaatgggat aagcatagca tttttccaaa agacgttttg 120
tcccaaatgg ggcaattggg ttttatggga atgctggtga gtgagaaatg ggcggatca 180 aatacaggaa atttagctta tgtgctggca cttgaagaaa tcgctgccgc agatggtgcg 240
acttcaacca ttatgagtgt acataattct gttggctgtg tacccattgc taaatttggt 300
acagaggagc aaaagcagaa atatctagtg cctttagcac aaggtgaaat gatcggtgca 360
tttgctttaa cggaaccaca tacaggttcc gatgccgcag ccattaaaac ccgagcaatt 420
aaacaaggtg atgaatggat tattaatggc gctaaacaat ttataacatc aggtcataat 480
gcgggcgtga ttattgtatt tgctgtgaca gatccgaatg cagggaaaaa agggctgagt 540
gcatttattg tgccgcgtga aaccttgggt tatgaggtga ttcgcaccga agaaaaattg 600
ggtttacatg cgtcagatac gtgccaaatt gctttaacgg atgttcgagt acatcacagc 660
ttaatgcttg gtcaggaagg tgagggacta aaaatagcat tgtctaatct ggaaggtggc 720
cgtattggga ttgcagcgca agccgttggt ttggcacgtg ctgcactaga agaagcgaca 780
aaatatgcca aagagcgtgt gacctttgga aagcctattt ttgagcatca ggcgttagcc 840
tttcgtttag ccagtatggc cacagaaatt gaagcagcac gacaattggt tcattacgca 900
gcgcggctta aagaagctgg aaaaccttgt ttaaatgaag catcaatggc gaaattattt 960
tcatctgaaa tggtcgaacg cgtatgttct gctgctttgc aaatctttgg tggctatggc 1020
tatttaaaag actttcccat cgagcgaatt tatcgtgatg cacgtatttg ccagatttat 1080
gaaggtacaa gtgatattca gcgtttagtg atagcaagaa gcctataa 1128

<210> SEQ ID NO 11
<211> LENGTH: 774
<212> TYPE: DNA
<213> ORGANISM: Acinetobacter calcoaceticus

<400> SEQUENCE: 11
atgacattcg caacaatttt attggaaaaa cgtaagggtg tgggcttgat tacacttaac 60
cgtccaaaag cattaaatgc tttaaactca gaattaattt atgaaataaa tttagcctta 120
gacgatttag aaaatgatca aacgattggt tgtatcgtcc ttacaggttc agaaaaagcc 180
tttgccgcag gtgcggatat caaagaaatg gcagaattaa cttttccaaa tatttatttt 240
gatgattttt ttagtcttgc agatcgtatt gcacagcgtc gtaagccttt aattgccgca 300
gtgagtggtt atgctttagg tggtggctgt gagttagcac tcatgtgtga ctttatttat 360
tgtgccgaca atgccaagtt tgcactacca gaagtaactt taggtgtcat tcctggtatt 420
ggtggaacac agcgtctaac gcttgcaata ggcaaagcca aagccatgga aatgtgtttg 480
actgcacggc aaatgcaggc tgctgaggca gaacaaagtg gtttggtggc acgcgttttt 540
agtaaagaag aacttttaga acaaacctta caggctgccg aaaaaatagc ggaaaaatca 600
cgggtatcta ccataatgat taaagagtca attaatcgag cttttgaagt gagtttagca 660
gagggtttac gttttgagcg ccgaatgttc cattcagttt ttgcgacctt agatcagaaa 720
gaaggcatgc aagcatttat tgataaacgt ccagcccaat ttaaacatca ataa 774

<210> SEQ ID NO 12
<211> LENGTH: 1029

<212> TYPE: DNA
<213> ORGANISM: Acinetobacter calcoaceticus

<400> SEQUENCE: 12
atgactacta ctgacaatca tttactcatt gaacataaaa acgctttagg aacaattatt 60
ttaaatcgtc cagcgagtct gaacgcgcta tctctagaaa tgattaatgc gattcgtcaa 120
caagttgagg attggcaagg tgatgtaaat gttcaggcca tattaattaa atcaaatagt 180
cctaaagcat tttgtgcagg tggtgatatt cgctatcttt atgaaagtta taaaagtgga 240
tcagaagagt ataaagatta tttcattgct gaatatgaga tgctcaatag cattcgaacg 300
tctaaaaaaa cagtgattgt tttattggat ggatatgtat tgggtggtgg ttttggttta 360
gcacaggctt gtcatatctt ggtgagtagt gaaaaatcac gattttcaat gccagaaaca 420
gcaataggtt ttttcccaga tgttgcagcg acttatttct tatctcgttt agatgatgtt 480
ggggtatatt tggcactgac tggtgatcaa atcagtagta gtgatgcatt gtatttagat 540
ctgattgatt atcatgttcc gagtcagaat tttgagcgac tagaaaatgc attcagccaa 600
tcacagaact tagataaatt tcatattcag aagattattt ctgcttatat ctccagccct 660
gttcagagtg aactcagtct atggcttgaa gccattcgtc agcattttgg tcttaaaaat 720
gtgcaagata tcgaagaaag tttgaaaaat gaacaagatc ccaactatca agtatggaca 780
agtaaagtgt taaatacttt gcaacaacgt tcctctattg caaaaaaaac cagtttaaag 840
ttacagctgc tagggcgtgg atggtcatta cagcaatgta tgcgtatcga gcgaaaatta 900
caggatatct ggtttgaaca tggtgatatg attgagggtg ttcgagcgtt gattattgat 960
aaagataaac aaccgcaatg gcagcagcat aatgcgactt tagataatat attaggccaa 1020
ttaggttag 1029

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
atgcaattta atgaagaaca gctattaatt c 31

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
cagtctgaaa tgactaacct aattggc 27

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
acggaattct gaaggagctg gcaactatg 29

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
ttgtcgactt acttgaccag ggtacgcc 28

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
acagatctgg aggcctgtca tgagtgatta c 31

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
atgggtaccc attcagacct ccatc 25

<210> SEQ ID NO 19
<211> LENGTH: 6960
<212> TYPE: DNA
<213> ORGANISM: Artificial Sequence
<220> FEATURE:
<223> OTHER INFORMATION: Description of Artificial Sequence: New plasmid polynucleotide

<400> SEQUENCE: 19
ggggaattgt gagcggataa caattcccct gtagaaataa ttttgtttaa ctttaataag 60
gagatatacc atgggcagca gccatcacca tcatcaccac agccaggatc cgaattctga 120
aggagctggc aactatgtcg atggccgatc gtgatggcgt gatctggtat gacggtgaac 180
tggtgcagtg gcgcgacgcg accacgcacg tgctgaccca taccctgcac tatggaatgg 240
gcgtgttcga gggcgtgcgc gcctacgaca ccccgcaggg cacggcgatc ttccgcctgc 300
aggcgcatac cgaccggctg ttcgactccg cgcacatcat gaacatgcag atcccgtaca 360
gccgcgacga gatcaacgag gcgacccgcg ccgccgtgcg cgagaacaac ctggaaagcg 420
cctatatccg cccgatggtg ttctacggaa gcgaaggcat gggcctgcgc gccagcggcc 480
tgaaggtcca tgtgatcatc gccgcctgga gctggggcgc ctacatgggc gaggaagccc 540
tgcagcaagg catcaaggtg cgcaccagtt ccttcacccg ccaccacgtc aacatctcga 600
tgacccgcgc caagtccaac ggcgcctaca tcaactcgat gctggccctc caggaagcga 660
tctccggcgg cgccgacgag gccatgatgc tcgatccgga aggctacgtg gccgaaggct 720
ccggcgagaa catcttcatc atcaaggatg gcgtgatcta caccccggaa gtcaccgcct 780
gcctgaacgg catcactcgt aacactatcc tgaccctggc cgccgaacac ggttttaaac 840

-continued

```
tggtcgagaa gcgcatcacc cgcgacgagg tgtacatcgc cgacgaggcc ttcttcactg    900
gcactgccgc ggaagtcacg ccgatccgcg aagtggacgg tcgcaagatc ggcgccggcc    960
gccgtggccc ggtcaccgaa aagctgcaga aagcctattt cgacctggtc agcggcaaga   1020
ccgaggccca cgccgagtgg cgtaccctgg tcaagtaagt cgacaagctt gcggccgcat   1080
aatgcttaag tcgaacagaa agtaatcgta ttgtacacgg ccgcataatc gaaattaata   1140
cgactcacta taggggaatt gtgagcggat aacaattccc catcttagta tattagttaa   1200
gtataagaag gagatataca tatggcagat ctggaggcct gtcatgagtg attacgagcc   1260
gttgcgtctg catgtcccgg agcccaccgg gcgtcctggc tgcaagaccg acttttccta   1320
tctgcacctg tcccccgccg gcgaggtacg caagccgccg gtggatgtcg agcccgccga   1380
gaccagcgac ctggcctaca gcctggtacg tgtgctcgac gacgacggcc acgccgtcgg   1440
tccctggaat ccgcagctca gcaacgaaca actgctgcgc ggcatgcggg cgatgctcaa   1500
gacccgcctg ttcgacgcgc gcatgctcac cgcgcaacgg cagaaaaagc tttccttcta   1560
tatgcaatgc ctcggcgagg aagccatcgc caccgcccac accctggccc tgcgcgacgg   1620
cgacatgtgc tttccgacct atcgccagca aggcatcctg atcacccgcg aatacccgct   1680
ggtggacatg atctgccagc ttctctccaa cgaggccgac ccgctcaagg gccgccagct   1740
gccgatcatg tactcgagca aggaggcagg tttcttctcc atctccggca acctcgccac   1800
ccagttcatc caggcggtcg gctggggcat ggcctcggcg atcaagggcg acacgcgcat   1860
cgcctcggcc tggatcggcg acggcgccac cgccgagtcg gacttccaca ccgccctcac   1920
cttcgcccat gtctaccgcg cgccggtaat cctcaacgtg gtcaacaacc agtgggcgat   1980
ctccaccttc caggccatcg ccggcggcga aggcaccacc ttcgccaacc gtggcgtggg   2040
ctgcgggatc gcctcgctgc gggtcgacgg caatgacttc ctggcggtct acgccgcctc   2100
cgagtgggcc gccgagcgcg cccggcgcaa cctcgggccg agcctgatcg aatgggtcac   2160
ctaccgcgcc ggcccgcact cgacttcgga cgacccgtcc aagtaccgcc ccgccgacga   2220
ctggaccaac ttcccgctgg gcgacccgat cgcccgcctg aagcggcaca tgatcggcct   2280
cggcatctgg tcggaggaac agcacgaagc cacccacaag gccctcgaag ccgaagtact   2340
ggccgcgcag aaacaggcgg agagccatgg caccctgatc gacggccggg tgccgagcgc   2400
cgccagcatg ttcgaggacg tctatgcaga actgccggag cacctgcgcc ggcaacgcca   2460
ggagctcggg gtatgaatgc catgaacccg caacacgaga acgcccagac ggtcaccagc   2520
atgaccatga tccaggcgct gcgctcggcg atggacatca tgctcgagcg cgacgacgac   2580
gtggtggtat tcggccagga cgtcggctac ttcggcggcg tgttccgctg caccgaaggc   2640
ctgcagaaga aatacggcac ctcgcgggtg ttcgatgcgc cgatctccga gagcggcatc   2700
atcggcgccg cggtcggcat gggtgcctac ggcctgcgcc cggtggtgga gatccagttc   2760
gccgactacg tctacccggc ctccgaccag ttgatctccg aggcggcgcg cctgcgctat   2820
cgctcggccg gcgacttcat cgtgccgatg accgtacgca tgccctgtgg cggcggcatc   2880
tacggcgggc aaacgcacag ccagagcccg gaggcgatgt tcacccaggt ctgcggcctg   2940
cgcacggtga tgccgtccaa cccctacgac gccaagggcc tgctgatcgc ctgcatcgag   3000
aacgacgacc cggtgatctt cctcgagccc aagcgcctct acaacggccc gttcgatggc   3060
caccacgacc gcccggtgac gccctggtcc aagcatccgg ccagccaggt gccggacggc   3120
tactacaagg tgccgctgga caaggcggcg atcgtccgcc ccggcgcggc gctgaccgtg   3180
ctgacctacg gcaccatggt ctacgtggcc caggccgcgg ccgacgagac cggcctggac   3240
```

-continued

```
gccgagatca tcgacctgcg cagcctctgg ccgctggacc tggaaaccat cgtcgcctcg   3300
gtgaagaaga ccggccgctg cgtcatcgcc cacgaggcga cccgcacctg cgggttcggc   3360
gccgagctga tgtcgctggt gcaggagcac tgcttccacc acctggaggc gccgatcgag   3420
cgcgtcaccg gttgggacac cccctacccg catgcccagg agtgggcgta tttccccggc   3480
cccgcgcgcg tcggcgcggc attcaagcgt gtgatggagg tctgaatggg taccctcgag   3540
tctggtaaag aaaccgctgc tgcgaaattt gaacgccagc acatggactc gtctactagc   3600
gcagcttaat taacctaggc tgctgccacc gctgagcaat aactagcata accccttggg   3660
gcctctaaac gggtcttgag gggttttttg ctgaaacctc aggcatttga gaagcacacg   3720
gtcacactgc ttccggtagt caataaaccg gtaaaccagc aatagacata agcggctatt   3780
taacgaccct gccctgaacc gacgaccggg tcatcgtggc cggatcttgc ggcccctcgg   3840
cttgaacgaa ttgttagaca ttatttgccg actaccttgg tgatctcgcc tttcacgtag   3900
tggacaaatt cttccaactg atctgcgcgc gaggccaagc gatcttcttc ttgtccaaga   3960
taagcctgtc tagcttcaag tatgacgggc tgatactggg ccggcaggcg ctccattgcc   4020
cagtcggcag cgacatcctt cggcgcgatt ttgccggtta ctgcgctgta ccaaatgcgg   4080
gacaacgtaa gcactacatt tcgctcatcg ccagcccagt cgggcggcga gttccatagc   4140
gttaaggttt catttagcgc ctcaaataga tcctgttcag gaaccggatc aaagagttcc   4200
tccgccgctg gacctaccaa ggcaacgcta tgttctcttg cttttgtcag caagatagcc   4260
agatcaatgt cgatcgtggc tggctcgaag atacctgcaa gaatgtcatt gcgctgccat   4320
tctccaaatt gcagttcgcg cttagctgga taacgccacg gaatgatgtc gtcgtgcaca   4380
acaatggtga cttctacagc gcggagaatc tcgctctctc caggggaagc cgaagtttcc   4440
aaaaggtcgt tgatcaaagc tcgccgcgtt gtttcatcaa gccttacggt caccgtaacc   4500
agcaaatcaa tatcactgtg tggcttcagg ccgccatcca ctgcggagcc gtacaaatgt   4560
acggccagca acgtcggttc gagatggcgc tcgatgacgc caactacctc tgatagttga   4620
gtcgatactt cggcgatcac cgcttccctc atactcttcc tttttcaata ttattgaagc   4680
atttatcagg gttattgtct catgagcgga tacatatttg aatgtattta gaaaaataaa   4740
caaatagcta gctcactcgg tcgctacgct ccgggcgtga gactgcggcg ggcgctgcgg   4800
acacatacaa agttacccac agattccgtg gataagcagg ggactaacat gtgaggcaaa   4860
acagcagggc cgcgccggtg gcgtttttcc ataggctccg ccctcctgcc agagttcaca   4920
taaacagacg cttttccggt gcatctgtgg gagccgtgag gctcaaccat gaatctgaca   4980
gtacgggcga aacccgacag gacttaaaga tccccaccgt ttccggcggg tcgctccctc   5040
ttgcgctctc ctgttccgac cctgccgttt accggatacc tgttccgcct ttctccctta   5100
cgggaagtgt ggcgctttct catagctcac acactggtat ctcggctcgg tgtaggtcgt   5160
tcgctccaag ctgggctgta agcaagaact ccccgttcag cccgactgct gcgccttatc   5220
cggtaactgt tcacttgagt ccaacccgga aaagcacggt aaaacgccac tggcagcagc   5280
cattggtaac tgggagttcg cagaggattt gtttagctaa acacgcggtt gctcttgaag   5340
tgtgcgccaa agtccggcta cactggaagg acagatttgg ttgctgtgct ctgcgaaagc   5400
cagttaccac ggttaagcag ttccccaact gacttaacct tcgatcaaac cacctcccca   5460
ggtggttttt tcgtttacag ggcaaaagat tacgcgcaga aaaaaaggat ctcaagaaga   5520
tcctttgatc ttttctactg aaccgctcta gatttcagtg caatttatct cttcaaatgt   5580
```

```
agcacctgaa gtcagcccca tacgatataa gttgtaattc tcatgttagt catgccccgc   5640

gcccaccgga aggagctgac tgggttgaag gctctcaagg gcatcggtcg agatcccggt   5700

gcctaatgag tgagctaact tacattaatt gcgttgcgct cactgcccgc tttccagtcg   5760

ggaaacctgt cgtgccagct gcattaatga atcggccaac gcgcggggag aggcggtttg   5820

cgtattgggc gccagggtgg tttttctttt caccagtgag acgggcaaca gctgattgcc   5880

cttcaccgcc tggccctgag agagttgcag caagcggtcc acgctggttt gccccagcag   5940

gcgaaaatcc tgtttgatgg tggttaacgg cgggatataa catgagctgt cttcggtatc   6000

gtcgtatccc actaccgaga tgtccgcacc aacgcgcagc ccggactcgg taatggcgcg   6060

cattgcgccc agcgccatct gatcgttggc aaccagcatc gcagtgggaa cgatgccctc   6120

attcagcatt tgcatggttt gttgaaaacc ggacatggca ctccagtcgc cttcccgttc   6180

cgctatcggc tgaatttgat tgcgagtgag atatttatgc cagccagcca gacgcagacg   6240

cgccgagaca gaacttaatg ggcccgctaa cagcgcgatt tgctggtgac ccaatgcgac   6300

cagatgctcc acgcccagtc gcgtaccgtc ttcatgggag aaaataatac tgttgatggg   6360

tgtctggtca gagacatcaa gaaataacgc cggaacatta gtgcaggcag cttccacagc   6420

aatggcatcc tggtcatcca gcggatagtt aatgatcagc ccactgacgc gttgcgcgag   6480

aagattgtgc accgccgctt tacaggcttc gacgccgctt cgttctacca tcgacaccac   6540

cacgctggca cccagttgat cggcgcgaga tttaatcgcc gcgacaattt gcgacggcgc   6600

gtgcagggcc agactggagg tggcaacgcc aatcagcaac gactgtttgc ccgccagttg   6660

ttgtgccacg cggttgggaa tgtaattcag ctccgccatc gccgcttcca ctttttcccg   6720

cgttttcgca gaaacgtggc tggcctggtt caccacgcgg gaaacggtct gataagagac   6780

accggcatac tctgcgacat cgtataacgt tactggtttc acattcacca ccctgaattg   6840

actctcttcc gggcgctatc atgccatacc gcgaaaggtt ttgcgccatt cgatggtgtc   6900

cgggatctcg acgctctccc ttatgcgact cctgcattag gaaattaata cgactcacta   6960
```

<210> SEQ ID NO 20
<211> LENGTH: 8757
<212> TYPE: DNA
<213> ORGANISM: Artificial Sequence
<220> FEATURE:
<223> OTHER INFORMATION: Description of Artificial Sequence: New plasmid polynucleotide

<400> SEQUENCE: 20

```
caaggagatg gcgcccaaca gtcccccggc cacggggcct gccaccatac ccacgccgaa     60

acaagcgctc atgagcccga agtggcgagc ccgatcttcc ccatcggtga tgtcggcgat    120

ataggcgcca gcaaccgcac ctgtggcgcc ggtgatgccg gccacgatgc gtccggcgta    180

gaggatcgag atctcgatcc cgcgaaatta atacgactca ctatagggga attgtgagcg    240

gataacaatt cccctctaga aataattttg tttaacttta agaaggaatt caggagccct    300

tatgcaattt aatgaagaac agctattaat tcaggatatg gcgaaaagtt ttgccaatga    360

acagattaaa tctaatgcag cagaatggga taagcatagc atttttccaa aagacgtttt    420

gtcccaaatg gggcaattgg gttttatggg aatgctggtg agtgagaaat ggggcggatc    480

aaatacagga aatttagctt atgtgctggc acttgaagaa atcgctgccg cagatggtgc    540

gacttcaacc attatgagtg tacataattc tgttggctgt gtacccattg ctaaatttgg    600

tacagaggag caaaaagcaga aatatctagt gcctttagca caaggtgaaa tgatcggtgc    660
```

-continued

```
atttgcttta acggaaccac atacaggttc cgatgccgca gccattaaaa cccgagcaat    720
taaacaaggt gatgaatgga ttattaatgg cgctaaacaa tttataacat caggtcataa    780
tgcgggcgtg attattgtat ttgctgtgac agatccgaat gcagggaaaa aagggctgag    840
tgcatttatt gtgccgcgtg aaaccttggg ttatgaggtg attcgcaccg aagaaaaatt    900
gggtttacat gcgtcagata cgtgccaaat tgctttaacg gatgttcgag tacatcacag    960
cttaatgctt ggtcaggaag gtgagggact aaaaatagca ttgtctaatc tggaaggtgg   1020
ccgtattggg attgcagcgc aagccgttgg tttggcacgt gctgcactag aagaagcgac   1080
aaaatatgcc aaagagcgtg tgacctttgg aaagcctatt tttgagcatc aggcgttagc   1140
ctttcgttta gccagtatgg ccacagaaat tgaagcagca cgacaattgg ttcattacgc   1200
agcgcggctt aaagaagctg gaaaaccttg tttaaatgaa gcatcaatgg cgaaattatt   1260
ttcatctgaa atggtcgaac gcgtatgttc tgctgctttg caaatctttg gtggctatgg   1320
ctatttaaaa gactttccca tcgagcgaat ttatcgtgat gcacgtattt gccagattta   1380
tgaaggtaca agtgatattc agcgtttagt gatagcaaga agcctataac tgacctttgc   1440
tgctgtattt ttatcataaa attaagataa ggattctaaa aatgacattc gcaacaattt   1500
tattggaaaa acgtaagggt gtgggcttga ttacacttaa ccgtccaaaa gcattaaatg   1560
ctttaaactc agaattaatt tatgaaataa atttagcctt agacgattta gaaaatgatc   1620
aaacgattgg ttgtatcgtc cttacaggtt cagaaaaagc ctttgccgca ggtgcggata   1680
tcaaagaaat ggcagaatta acttttccaa atatttattt tgatgatttt tttagtcttg   1740
cagatcgtat tgcacagcgt cgtaagcctt taattgccgc agtgagtggt tatgctttag   1800
gtggtggctg tgagttagca ctcatgtgtg actttattta ttgtgccgac aatgccaagt   1860
ttgcactacc agaagtaact ttaggtgtca ttcctggtat tggtggaaca cagcgtctaa   1920
cgcttgcaat aggcaaagcc aaagccatgg aaatgtgttt gactgcacgg caaatgcagg   1980
ctgctgaggc agaacaaagt ggtttggtgg cacgcgtttt tagtaaagaa gaacttttag   2040
aacaaacctt acaggctgcc gaaaaaatag cggaaaaatc acgggtatct accataatga   2100
ttaaagagtc aattaatcga gcttttgaag tgagtttagc agagggttta cgttttgagc   2160
gccgaatgtt ccattcagtt tttgcgacct tagatcagaa agaaggcatg caagcattta   2220
ttgataaacg tccagcccaa tttaaacatc aataatagga tgaagcgatg actactactg   2280
acaatcattt actcattgaa cataaaaacg ctttaggaac aattatttta aatcgtccag   2340
cgagtctgaa cgcgctatct ctagaaatga ttaatgcgat tcgtcaacaa gttgaggatt   2400
ggcaaggtga tgtaaatgtt caggccatat taattaaatc aaatagtcct aaagcatttt   2460
gtgcaggtgg tgatattcgc tatctttatg aaagttataa aagtggatca gaagagtata   2520
aagattattt cattgctgaa tatgagatgc tcaatagcat tcgaacgtct aaaaaaacag   2580
tgattgtttt attggatgga tatgtattgg gtggtggttt tggtttagca caggcttgtc   2640
atatcttggt gagtagtgaa aaatcacgat tttcaatgcc agaaacagca ataggttttt   2700
tcccagatgt tgcagcgact tatttcttat ctcgtttaga tgatgttggg gtatatttgg   2760
cactgactgg tgatcaaatc agtagtagtg atgcattgta tttagatctg attgattatc   2820
atgttccgag tcagaatttt gagcgactag aaaatgcatt cagccaatca cagaacttag   2880
ataaatttca tattcagaag attatttctg cttatatctc cagccctgtt cagagtgaac   2940
tcagtctatg gcttgaagcc attcgtcagc attttggtct taaaaatgtg caagatatcg   3000
aagaaagttt gaaaaatgaa caagatccca actatcaagt atggacaagt aaagtgttaa   3060
```

atactttgca acaacgttcc tctattgcaa aaaaaaccag tttaaagtta cagctgctag 3120
ggcgtggatg gtcattacag caatgtatgc gtatcgagcg aaaattacag gatatctggt 3180
ttgaacatgg tgatatgatt gagggtgttc gagcgttgat tattgataaa gataaacaac 3240
cgcaatggca gcagcataat gcgactttag ataatatatt aggccaatta ggttagtcat 3300
ttcagactga agggcgagct caattcgaag cttgaaggta agcctatccc taaccctctc 3360
ctcggtctcg attctacgcg taccggtcat catcaccatc accattgagt ttgatccggc 3420
tgctaacaaa gcccgaaagg aagctgagtt ggctgctgcc accgctgagc aataactagc 3480
ataacccctt ggggcctcta aacgggtctt gaggggtttt ttgctgaaag gaggaactat 3540
atccggatat cccgcaagag gcccggcagt accggcataa ccaagcctat gcctacagca 3600
tccagggtga cggtgccgag gatgacgatg agcgcattgt tagatttcat acacggtgcc 3660
tgactgcgtt agcaatttaa ctgtgataaa ctaccgcatt aaagcttatc gatgataagc 3720
tgtcaaacat gagaattaat tcttgaagac gaaagggcct cgtgatacgc ctatttttat 3780
aggttaatgt catgataata atggtttctt agacgtcagg tggcactttt cggggaaatg 3840
tgcgcggaac ccctatttgt ttatttttct aaatacattc aaatatgtat ccgctcatga 3900
gacaataacc ctgataaatg cttcaataat attgaaaaag gaagagtatg agtattcaac 3960
atttccgtgt cgcccttatt cccttttttg cggcattttg ccttcctgtt tttgctcacc 4020
cagaaacgct ggtgaaagta aaagatgctg aagatcagtt gggtgcacga gtgggttaca 4080
tcgaactgga tctcaacagc ggtaagatcc ttgagagttt tcgccccgaa gaacgttttc 4140
caatgatgag cacttttaaa gttctgctat gtggcgcggt attatcccgt gttgacgccg 4200
ggcaagagca actcggtcgc cgcatacact attctcagaa tgacttggtt gagtactcac 4260
cagtcacaga aaagcatctt acggatggca tgacagtaag agaattatgc agtgctgcca 4320
taaccatgag tgataacact gcggccaact tacttctgac aacgatcgga ggaccgaagg 4380
agctaaccgc ttttttgcac aacatggggg atcatgtaac tcgccttgat cgttgggaac 4440
cggagctgaa tgaagccata ccaaacgacg agcgtgacac cacgatgcct gcagcaatgg 4500
caacaacgtt gcgcaaacta ttaactggcg aactacttac tctagcttcc cggcaacaat 4560
taatagactg gatggaggcg gataaagttg caggaccact tctgcgctcg gcccttccgg 4620
ctggctggtt tattgctgat aaatctggag ccggtgagcg tgggtctcgc ggtatcattg 4680
cagcactggg gccagatggt aagccctccc gtatcgtagt tatctacacg acggggagtc 4740
aggcaactat ggatgaacga aatagacaga tcgctgagat aggtgcctca ctgattaagc 4800
attggtaact gtcagaccaa gtttactcat atatacttta gattgattta aaacttcatt 4860
tttaatttaa aaggatctag gtgaagatcc tttttgataa tctcatgacc aaaatccctt 4920
aacgtgagtt ttcgttccac tgagcgtcag accccgtaga aaagatcaaa ggatcttctt 4980
gagatccttt ttttctgcgc gtaatctgct gcttgcaaac aaaaaaacca ccgctaccag 5040
cggtggtttg tttgccggat caagagctac caactctttt tccgaaggta actggcttca 5100
gcagagcgca gataccaaat actgtccttc tagtgtagcc gtagttaggc caccacttca 5160
agaactctgt agcaccgcct acatacctcg ctctgctaat cctgttacca gtggctgctg 5220
ccagtggcga taagtcgtgt cttaccgggt tggactcaag acgatagtta ccggataagg 5280
cgcagcggtc gggctgaacg gggggttcgt gcacacagcc cagcttggag cgaacgacct 5340
acaccgaact gagataccta cagcgtgagc tatgagaaag cgccacgctt cccgaaggga 5400

-continued

```
gaaaggcgga caggtatccg gtaagcggca gggtcggaac aggagagcgc acgagggagc   5460
ttccaggggg aaacgcctgg tatctttata gtcctgtcgg gtttcgccac ctctgacttg   5520
agcgtcgatt tttgtgatgc tcgtcagggg ggcggagcct atggaaaaac gccagcaacg   5580
cggccttttt acggttcctg gccttttgct ggccttttgc tcacatgttc tttcctgcgt   5640
tatcccctga ttctgtggat aaccgtatta ccgcctttga gtgagctgat accgctcgcc   5700
gcagccgaac gaccgagcgc agcgagtcag tgagcgagga agcggaagag cgcctgatgc   5760
ggtattttct ccttacgcat ctgtgcggta tttcacaccg caatggtgca ctctcagtac   5820
aatctgctct gatgccgcat agttaagcca gtatacactc cgctatcgct acgtgactgg   5880
gtcatggctg cgccccgaca cccgccaaca cccgctgacg cgccctgacg ggcttgtctg   5940
ctcccggcat ccgcttacag acaagctgtg accgtctccg ggagctgcat gtgtcagagg   6000
ttttcaccgt catcaccgaa acgcgcgagg cagctgcggt aaagctcatc agcgtggtcg   6060
tgaagcgatt cacagatgtc tgcctgttca tccgcgtcca gctcgttgag tttctccaga   6120
agcgttaatg tctggcttct gataaagcgg gccatgttaa gggcggtttt ttcctgtttg   6180
gtcactgatg cctccgtgta agggggattt ctgttcatgg gggtaatgat accgatgaaa   6240
cgagagagga tgctcacgat acgggttact gatgatgaac atgcccggtt actggaacgt   6300
tgtgagggta aacaactggc ggtatggatg cggcgggacc agagaaaaat cactcagggt   6360
caatgccagc gcttcgttaa tacagatgta ggtgttccac agggtagcca gcagcatcct   6420
gcgatgcaga tccggaacat aatggtgcag ggcgctgact tccgcgtttc cagactttac   6480
gaaacacgga aaccgaagac cattcatgtt gttgctcagg tcgcagacgt tttgcagcag   6540
cagtcgcttc acgttcgctc gcgtatcggt gattcattct gctaaccagt aaggcaaccc   6600
cgccagccta gccgggtcct caacgacagg agcacgatca tgcgcacccg tggccaggac   6660
ccaacgctgc ccgagatgcg ccgcgtgcgg ctgctggaga tggcggacgc gatggatatg   6720
ttctgccaag ggttggtttg cgcattcaca gttctccgca agaattgatt ggctccaatt   6780
cttggagtgg tgaatccgtt agcgaggtgc cgccggcttc cattcaggtc gaggtggccc   6840
ggctccatgc accgcgacgc aacgcgggga ggcagacaag gtatagggcg gcgcctacaa   6900
tccatgccaa cccgttccat gtgctcgccg aggcggcata aatcgccgtg acgatcagcg   6960
gtccaatgat cgaagttagg ctggtaagag ccgcgagcga tccttgaagc tgtccctgat   7020
ggtcgtcatc tacctgcctg gacagcatgg cctgcaacgc gggcatcccg atgccgccgg   7080
aagcgagaag aatcataatg gggaaggcca tccagcctcg cgtcgcgaac gccagcaaga   7140
cgtagcccag cgcgtcggcc gccatgccgg cgataatggc ctgcttctcg ccgaaacgtt   7200
tggtggcggg accagtgacg aaggcttgag cgagggcgtg caagattccg aataccgcaa   7260
gcgacaggcc gatcatcgtc gcgctccagc gaaagcggtc ctcgccgaaa atgacccaga   7320
gcgctgccgg cacctgtcct acgagttgca tgataaagaa gacagtcata agtgcggcga   7380
cgatagtcat gccccgcgcc caccggaagg agctgactgg gttgaaggct ctcaagggca   7440
tcggtcgaga tcccggtgcc taatgagtga gctaacttac attaattgcg ttgcgctcac   7500
tgcccgcttt ccagtcggga aacctgtcgt gccagctgca ttaatgaatc ggccaacgcg   7560
cggggagagg cggtttgcgt attgggcgcc agggtggttt ttcttttcac cagtgagacg   7620
ggcaacagct gattgccctt caccgcctgg ccctgagaga gttgcagcaa gcggtccacg   7680
ctggtttgcc ccagcaggcg aaaatcctgt ttgatggtgg ttaacggcgg gatataacat   7740
gagctgtctt cggtatcgtc gtatcccact accgagatat ccgcaccaac gcgcagcccg   7800
```

gactcggtaa tggcgcgcat tgcgcccagc gccatctgat cgttggcaac cagcatcgca 7860
gtgggaacga tgccctcatt cagcatttgc atggtttgtt gaaaaccgga catggcactc 7920
cagtcgcctt cccgttccgc tatcggctga atttgattgc gagtgagata tttatgccag 7980
ccagccagac gcagacgcgc cgagacagaa cttaatgggc ccgctaacag cgcgatttgc 8040
tggtgaccca atgcgaccag atgctccacg cccagtcgcg taccgtcttc atgggagaaa 8100
ataatactgt tgatgggtgt ctggtcagag acatcaagaa ataacgccgg aacattagtg 8160
caggcagctt ccacagcaat ggcatcctgg tcatccagcg gatagttaat gatcagccca 8220
ctgacgcgtt gcgcgagaag attgtgcacc gccgctttac aggcttcgac gccgcttcgt 8280
tctaccatcg acaccaccac gctggcaccc agttgatcgg cgcgagattt aatcgccgcg 8340
acaatttgcg acggcgcgtg cagggccaga ctggaggtgg caacgccaat cagcaacgac 8400
tgtttgcccg ccagttgttg tgccacgcgg ttgggaatgt aattcagctc cgccatcgcc 8460
gcttccactt tttcccgcgt tttcgcagaa acgtggctgg cctggttcac cacgcgggaa 8520
acggtctgat aagagacacc ggcatactct gcgacatcgt ataacgttac tggtttcaca 8580
ttcaccaccc tgaattgact ctcttccggg cgctatcatg ccataccgcg aaaggttttg 8640
cgccattcga tggtgtccgg gatctcgacg ctctccctta tgcgactcct gcattaggaa 8700
gcagcccagt agtaggttga ggccgttgag caccgccgcc gcaaggaatg gtgcatg 8757

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
attatcccat ggggagaaca ttaaaagc 28

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
cgggatcctt acttttcaat atatcc 26

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
cggtcgacaa ggagatatag atatgactga tctcacaaag actgc 45

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 24
cttaggcttt gtcgaacgcc tcc 23

<210> SEQ ID NO 25
<211> LENGTH: 870
<212> TYPE: DNA
<213> ORGANISM: Artificial Sequence
<220> FEATURE:
<223> OTHER INFORMATION: Description of Artificial Sequence: New vector polynucleotide

<400> SEQUENCE: 25
atggaaaagg tggcattcat cggcctgggc gcaatgggct acccaatggc aggtcacctg 60
gctcgccgct tcccaaccct ggtgtggaac cgcaccttcg aaaaggcact gcgccaccag 120
gaagagttcg gctccgaagc agtgccactg gaacgcgtgg ctgaagcacg cgtgatcttc 180
acctgcctgc caaccacccg cgaagtgtac gaagtggcag aagcactgta cccatacctg 240
cgcgaaggca cctactgggt ggatgcaacc tccggcgaac cagaagcatc ccgccgcctg 300
gctgaacgcc tgcgcgaaaa gggcgtgacc tacctggatg caccagtgtc cggtggcacc 360
tccggtgcag aagcaggcac cctgaccgtt atgctgggcg gtccagaaga agcagtcgaa 420
cgcgtccgcc cattcctggc ctacgcaaag aaggtggtcc acgtcggccc agttggtgca 480
ggccacgcag tgaaggcaat caacaacgca ctgctggccg tgaacctgtg ggcagcaggc 540
gaaggtctgc tggccctggt gaagcagggc gtgtccgcag aaaaggccct ggaagtgatc 600
aacgcatcct ccggccgctc caacgcaacc gaaaacctga tcccacagcg cgttctgacc 660
cgcgcattcc caaagacctt cgcactgggc ctgctggtga aggatctggg catcgcaatg 720
ggcgtgctgg atggcgaaaa ggcaccatcc ccactgctgc gcctggctcg cgaagtctac 780
gagatggcaa agcgcgaact cggcccagat gcagatcacg tggaagcact gcgcctgctc 840
gaacgctggg gcggtgtgga aatccgctaa 870

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
tgaagatcct aggaggttta aacatatgcc gttaatagcc gggattg 47

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tatatagtcg acttaattcg cctgaccggc cag 33

<210> SEQ ID NO 28
<211> LENGTH: 29
<212> TYPE: DNA
<213> ORGANISM: Artificial Sequence
<220> FEATURE:

<223> OTHER INFORMATION: Description of Artificial Sequence: Synthetic
primer

<400> SEQUENCE: 28
tatataacat gtcgctttca ccgccaggc 29

<210> SEQ ID NO 29
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
catatgttta aacctcctag gatcttcagt ttctctcact taacggcagg 50

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30
tatataccat ggcgctttca ccgccaggc 29

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31
tatatagtcg acttaattcg cctgaccggc cag 33

<210> SEQ ID NO 32
<211> LENGTH: 40
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32
tatatacata tgaaaagatc aaaacgattt gcagtactgg 40

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 33
tatatagtcg acttagcttc ctttacgcag cttatgc 37

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
aaaacatatg aattttcatc atctggctta ctgg 34

<210> SEQ ID NO 35
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
aaaacatatg tatatttcct tctttcaggc ctccaggctt atccagatg 49

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ggaggcaacc atggccctcg acgtgcagag 30

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
gagacttgcg gatccctccg atcaggcctt gc 32

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
aaaacatatg atcgacactg cgccccttgc 30

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
aagacgtcct accgctcgcc ggccgtcc 28

<210> SEQ ID NO 40
<211> LENGTH: 3967
<212> TYPE: DNA
<213> ORGANISM: Artificial Sequence
<220> FEATURE:
<223> OTHER INFORMATION: Description of Artificial Sequence: New plasmid polynucleotide

<400> SEQUENCE: 40
atgcgccgca ccctgaaggc agcaatcctg ggcgccaccg gcctggtggg catcgaatac 60
gtgcgcatgc tgtccaacca cccatacatc aagccagcat acctggccgg caagggctcc 120
gttggcaagc catacggcga agtggtgcgc tggcagaccg tgggccaggt gccaaaggaa 180
atcgcagata tggaaatcaa gccaaccgat ccaaagctga tggatgatgt ggatatcatc 240
ttctccccac tgccacaggg tgcagcaggc ccagtggaag aacagttcgc aaaggaaggc 300
ttcccagtga tctccaactc cccagatcac cgcttcgatc cagatgtgcc actgctggtg 360
ccagaactca acccacacac catctccctg atcgatgaac agcgcaagcg ccgcgaatgg 420
aagggcttca tcgtgaccac cccactgtgc accgcacagg gcgcagcaat cccactgggc 480
gcaatcttca aggattacaa gatggatggc gcattcatca ccaccatcca gtccctgtcc 540
ggcgcaggct acccaggtat cccatccctg gatgtggtgg ataacatcct gccactgggc 600
gatggctacg atgcaaagac catcaaggaa atcttccgca tcctgtccga agtgaagcgc 660
aacgtggatg aaccaaagct ggaagatgtg tccctggccg caaccaccca ccgcatcgca 720
accatccacg gccactacga agtgctgtac gtgtccttca aggaagaaac cgcagcagaa 780
aaggtgaagg aaaccctgga aaacttccgc ggcgaaccac aggatctgaa gctgccaacc 840
gcaccatcca agccaatcat cgtgatgaac gaagataccc gcccacaggt gtacttcgat 900
cgctgggcag gcgatatccc aggcatgtcc gtggtggtgg gccgcctgaa gcaggtgaac 960
aagcgcatga tccgcctggt gtccctgatc cacaacaccg ttcgcggcgc agcaggtggt 1020
ggtatcctgg ccgcagaact cctggtggaa aagggctaca tcgaaaagta agaattccgc 1080
gagctccagc ttttgttccc tttagtgagg gttaattgcg cgcttggcgt aatcatggtc 1140
atagctgttt cctgtgtgaa attgttatcc gctcacaatt ccacacaaca tacgagccgg 1200
aagcataaag tgtaaagcct ggggtgccta atgagtgagc taactcacat taattgcgtt 1260
gcgctcactg cccgctttcc agtcgggaaa cctgtcgtgc cagctgcatt aatgaatcgg 1320
ccaacgcgcg gggagaggcg gtttgcgtat tgggcgctct tccgcttcct cgctcactga 1380
ctcgctgcgc tcggtcgttc ggctgcggcg agcggtatca gctcactcaa aggcggtaat 1440
acggttatcc acagaatcag gggataacgc aggaaagaac atgtgagcaa aaggccagca 1500
aaaggccagg aaccgtaaaa aggccgcgtt gctggcgttt ttccataggc tccgcccccc 1560
tgacgagcat cacaaaaatc gacgctcaag tcagaggtgg cgaaacccga caggactata 1620
aagataccag gcgtttcccc ctggaagctc cctcgtgcgc tctcctgttc cgaccctgcc 1680
gcttaccgga tacctgtccg cctttctccc ttcgggaagc gtggcgcttt ctcatagctc 1740
acgctgtagg tatctcagtt cggtgtaggt cgttcgctcc aagctgggct gtgtgcacga 1800
accccccgtt cagcccgacc gctgcgcctt atccggtaac tatcgtcttg agtccaaccc 1860
ggtaagacac gacttatcgc cactggcagc agccactggt aacaggatta gcagagcgag 1920
gtatgtaggc ggtgctacag agttcttgaa gtggtggcct aactacggct acactagaag 1980
aacagtattt ggtatctgcg ctctgctgaa gccagttacc ttcggaaaaa gagttggtag 2040
ctcttgatcc ggcaaacaaa ccaccgctgg tagcggtggt ttttttgttt gcaagcagca 2100
gattacgcgc agaaaaaaag gatctcaaga agatcctttg atcttttcta cggggtctga 2160
cgctcagtgg aacgaaaact cacgttaagg gattttggtc atgagattat caaaaaggat 2220
cttcacctag atccttttaa attaaaaatg aagttttaaa tcaatctaaa gtatatatga 2280

-continued

```
gtaaacttgg tctgacagtt accaatgctt aatcagtgag gcacctatct cagcgatctg   2340

tctatttcgt tcatccatag ttgcctgact ccccgtcgtg tagataacta cgatacggga   2400

gggcttacca tctggcccca gtgctgcaat gataccgcga gaacccacgct caccggctcc  2460

agatttatca gcaataaacc agccagccgg aagggccgag cgcagaagtg gtcctgcaac   2520

tttatccgcc tccatccagt ctattaattg ttgccgggaa gctagagtaa gtagttcgcc   2580

agttaatagt ttgcgcaacg ttgttgccat tgctacaggc atcgtggtgt cacgctcgtc   2640

gtttggtatg gcttcattca gctccggttc ccaacgatca aggcgagtta catgatcccc   2700

catgttgtgc aaaaaagcgg ttagctcctt cggtcctccg atcgttgtca gaagtaagtt   2760

ggccgcagtg ttatcactca tggttatggc agcactgcat aattctctta ctgtcatgcc   2820

atccgtaaga tgcttttctg tgactggtga gtactcaacc aagtcattct gagaatagtg   2880

tatgcggcga ccgagttgct cttgcccggc gtcaatacgg gataataccg cgccacatag   2940

cagaacttta aaagtgctca tcattggaaa acgttcttcg gggcgaaaac tctcaaggat   3000

cttaccgctg ttgagatcca gttcgatgta acccactcgt gcacccaact gatcttcagc   3060

atcttttact ttcaccagcg tttctgggtg agcaaaaaca ggaaggcaaa atgccgcaaa   3120

aaagggaata agggcgacac ggaaatgttg aatactcata ctcttccttt ttcaatatta   3180

ttgaagcatt tatcagggtt attgtctcat gagcggatac atatttgaat gtatttagaa   3240

aaataaacaa ataggggttc cgcgcacatt tccccgaaaa gtgccaccta aattgtaagc   3300

gttaatattt tgttaaaatt cgcgttaaat ttttgttaaa tcagctcatt ttttaaccaa   3360

taggccgaaa tcggcaaaat cccttataaa tcaaaagaat agaccgagat agggttgagt   3420

gttgttccag tttggaacaa gagtccacta ttaaagaacg tggactccaa cgtcaaaggg   3480

cgaaaaaccg tctatcaggg ctatggccca ctacgtgaac catcacccta atcaagtttt   3540

ttggggtcga ggtgccgtaa agcactaaat cggaacccta aagggagccc ccgatttaga   3600

gcttgacggg gaaagccggc gaacgtggcg agaaaggaag ggaagaaagc gaaaggagcg   3660

ggcgctaggg cgctggcaag tgtagcggtc acgctgcgcg taaccaccac acccgccgcg   3720

cttaatgcgc cgctacaggg cgcgtcccat tcgccattca ggctgcgcaa ctgttgggaa   3780

gggcgatcgg tgcgggcctc ttcgctatta cgccagctgg cgaaaggggg atgtgctgca   3840

aggcgattaa gttgggtaac gccagggttt tcccagtcac gacgttgtaa aacgacggcc   3900

agtgagcgcg cgtaatacga ctcactatag ggcgaattgg gtaccgcgga tccaaggaga   3960

tatagat                                                             3967


<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

aaccatgggc cgcaccctga agg                                           23


<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 42
aaggatcctt acttttcgat gtagcccttt tcc 33

<210> SEQ ID NO 43
<211> LENGTH: 3766
<212> TYPE: DNA
<213> ORGANISM: Artificial Sequence
<220> FEATURE:
<223> OTHER INFORMATION: Description of Artificial Sequence: New plasmid polynucleotide

<400> SEQUENCE: 43
atggaaaagg tggcattcat cggcctgggc gcaatgggct acccaatggc aggtcacctg 60
gctcgccgct tcccaaccct ggtgtggaac cgcaccttcg aaaaggcact gcgccaccag 120
gaagagttcg gctccgaagc agtgccactg gaacgcgtgg ctgaagcacg cgtgatcttc 180
acctgcctgc caaccacccg cgaagtgtac gaagtggcag aagcactgta cccatacctg 240
cgcgaaggca cctactgggt ggatgcaacc tccggcgaac cagaagcatc ccgccgcctg 300
gctgaacgcc tgcgcgaaaa gggcgtgacc tacctggatg caccagtgtc cggtggcacc 360
tccggtgcag aagcaggcac cctgaccgtt atgctgggcg gtccagaaga agcagtcgaa 420
cgcgtccgcc cattcctggc ctacgcaaag aaggtggtcc acgtcggccc agttggtgca 480
ggccacgcag tgaaggcaat caacaacgca ctgctggccg tgaacctgtg ggcagcaggc 540
gaaggtctgc tggccctggt gaagcagggc gtgtccgcag aaaaggccct ggaagtgatc 600
aacgcatcct ccggccgctc caacgcaacc gaaaacctga tcccacagcg cgttctgacc 660
cgcgcattcc caaagacctt cgcactgggc ctgctggtga aggatctggg catcgcaatg 720
ggcgtgctgg atggcgaaaa ggcaccatcc ccactgctgc gcctggctcg cgaagtctac 780
gagatggcaa agcgcgaact cggcccagat gcagatcacg tggaagcact gcgcctgctc 840
gaacgctggg gcggtgtgga aatccgctaa gaattccgcg agctccagct tttgttccct 900
ttagtgaggg ttaattgcgc gcttggcgta atcatggtca tagctgtttc ctgtgtgaaa 960
ttgttatccg ctcacaattc cacacaacat acgagccgga agcataaagt gtaaagcctg 1020
gggtgcctaa tgagtgagct aactcacatt aattgcgttg cgctcactgc ccgctttcca 1080
gtcgggaaac ctgtcgtgcc agctgcatta atgaatcggc caacgcgcgg ggagaggcgg 1140
tttgcgtatt gggcgctctt ccgcttcctc gctcactgac tcgctgcgct cggtcgttcg 1200
gctgcggcga gcggtatcag ctcactcaaa ggcggtaata cggttatcca cagaatcagg 1260
ggataacgca ggaaagaaca tgtgagcaaa aggccagcaa aaggccagga accgtaaaaa 1320
ggccgcgttg ctggcgtttt tccataggct ccgcccccct gacgagcatc acaaaaatcg 1380
acgctcaagt cagaggtggc gaaacccgac aggactataa agataccagg cgtttccccc 1440
tggaagctcc ctcgtgcgct ctcctgttcc gaccctgccg cttaccggat acctgtccgc 1500
ctttctccct tcgggaagcg tggcgctttc tcatagctca cgctgtaggt atctcagttc 1560
ggtgtaggtc gttcgctcca agctgggctg tgtgcacgaa ccccccgttc agcccgaccg 1620
ctgcgcctta tccggtaact atcgtcttga gtccaacccg gtaagacacg acttatcgcc 1680
actggcagca gccactggta acaggattag cagagcgagg tatgtaggcg gtgctacaga 1740
gttcttgaag tggtggccta actacggcta cactagaaga acagtatttg gtatctgcgc 1800
tctgctgaag ccagttacct tcggaaaaag agttggtagc tcttgatccg gcaaacaaac 1860
caccgctggt agcggtggtt tttttgtttg caagcagcag attacgcgca gaaaaaaagg 1920

-continued

```
atctcaagaa gatcctttga tcttttctac ggggtctgac gctcagtgga acgaaaactc   1980
acgttaaggg attttggtca tgagattatc aaaaaggatc ttcacctaga tccttttaaa   2040
ttaaaaatga agttttaaat caatctaaag tatatatgag taaacttggt ctgacagtta   2100
ccaatgctta atcagtgagg cacctatctc agcgatctgt ctatttcgtt catccatagt   2160
tgcctgactc cccgtcgtgt agataactac gatacgggag ggcttaccat ctggccccag   2220
tgctgcaatg ataccgcgag aaccacgctc accggctcca gatttatcag caataaacca   2280
gccagccgga agggccgagc gcagaagtgg tcctgcaact ttatccgcct ccatccagtc   2340
tattaattgt tgccgggaag ctagagtaag tagttcgcca gttaatagtt tgcgcaacgt   2400
tgttgccatt gctacaggca tcgtggtgtc acgctcgtcg tttggtatgg cttcattcag   2460
ctccggttcc caacgatcaa ggcgagttac atgatccccc atgttgtgca aaaaagcggt   2520
tagctccttc ggtcctccga tcgttgtcag aagtaagttg gccgcagtgt tatcactcat   2580
ggttatggca gcactgcata attctcttac tgtcatgcca tccgtaagat gcttttctgt   2640
gactggtgag tactcaacca agtcattctg agaatagtgt atgcggcgac cgagttgctc   2700
ttgcccggcg tcaatacggg ataataccgc gccacatagc agaactttaa aagtgctcat   2760
cattggaaaa cgttcttcgg ggcgaaaact ctcaaggatc ttaccgctgt tgagatccag   2820
ttcgatgtaa cccactcgtg cacccaactg atcttcagca tcttttactt tcaccagcgt   2880
ttctgggtga gcaaaaacag gaaggcaaaa tgccgcaaaa aagggaataa gggcgacacg   2940
gaaatgttga atactcatac tcttcctttt tcaatattat tgaagcattt atcagggtta   3000
ttgtctcatg agcggataca tatttgaatg tatttagaaa aataaacaaa taggggttcc   3060
gcgcacattt ccccgaaaag tgccacctaa attgtaagcg ttaatatttt gttaaaattc   3120
gcgttaaatt tttgttaaat cagctcattt tttaaccaat aggccgaaat cggcaaaatc   3180
ccttataaat caaaagaata gaccgagata gggttgagtg ttgttccagt ttggaacaag   3240
agtccactat taaagaacgt ggactccaac gtcaaagggc gaaaaaccgt ctatcagggc   3300
tatggcccac tacgtgaacc atcaccctaa tcaagttttt tggggtcgag gtgccgtaaa   3360
gcactaaatc ggaaccctaa agggagcccc cgatttagag cttgacgggg aaagccggcg   3420
aacgtggcga gaaaggaagg gaagaaagcg aaaggagcgg gcgctagggc gctggcaagt   3480
gtagcggtca cgctgcgcgt aaccaccaca cccgccgcgc ttaatgcgcc gctacagggc   3540
gcgtcccatt cgccattcag gctgcgcaac tgttgggaag ggcgatcggt gcgggcctct   3600
tcgctattac gccagctggc gaaaggggga tgtgctgcaa ggcgattaag ttgggtaacg   3660
ccagggtttt cccagtcacg acgttgtaaa acgacggcca gtgagcgcgc gtaatacgac   3720
tcactatagg gcgaattggg taccgcggat ccaaggagat atagat                  3766
```

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 44

```
aaaacatatg gaaaaggtgg cattcatcg                                       29
```

<210> SEQ ID NO 45
<211> LENGTH: 30

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

aaaagatctt tagcggattt ccacaccgcc                                     30
```